United States Patent [19]

Kit et al.

[11] Patent Number: 4,711,850

[45] Date of Patent: Dec. 8, 1987

[54] PSEUDORABIES VIRUS MUTANTS, VACCINES CONTAINING SAME, METHODS FOR THE PRODUCTION OF SAME AND METHODS FOR THE USE OF SAME

[75] Inventors: Malon Kit; Saul Kit, both of Houston, Tex.

[73] Assignees: NovaGene, Inc.; Baylor College of Medicine, both of Houston, Tex.

[21] Appl. No.: 823,439

[22] Filed: Jan. 28, 1986

[51] Int. Cl.$^4$ ...................... C12N 7/00; A61K 39/205

[52] U.S. Cl. .................................... 435/235; 435/236; 435/68; 435/172.1; 435/172.3; 424/89

[58] Field of Search ................ 435/68, 70, 172.3, 317, 435/91, 240, 255, 253, 235, 243; 935/15, 29, 32, 56, 57, 63, 65, 69, 72; 536/27

[56] References Cited

U.S. PATENT DOCUMENTS 4,514,497 4/1985 Kit et al. ............................ 435/235

OTHER PUBLICATIONS

Robbins et al., (1984), *J. Molecular and Applied Genetics,* vol. 2, pp. 485–496.

Methenleiter et al., (1985), *J. of Virology,* vol. 56, pp. 307–311.

Lomniczi et al., (1984), *J. Of Virology,* vol. 52, pp. 198–205.

Lee et al., (1982), *Proc. Nat'l. Acad. Sci. U.S.A.,* vol. 79, pp. 6612–6616.

Macs et al., (1983), *J. of Vetinary Rev.,* vol. 44, pp. 123–125.

Reed, (1982), 48th Annual Mtg., Ill. Vet. Med. Assoc.

*Primary Examiner*—Thomas G. Wiseman

*Assistant Examiner*—S. Seidman

*Attorney, Agent, or Firm*—Sughrue, Mion, Zinn, Macpeak, and Seas

[57] ABSTRACT

The present invention relates to pseudorabies virus mutants containing deletion and/or insertion mutations in a major viral glycoprotein gene, such that no antigenic polypeptides encoded by the viral gene are produced. As a result, animals vaccinated with such do not develop antibodies to the viral glycoprotein and can be distinguished from animals infected with pseudorabies virus field strains and known pseudorabies virus vaccine strains. The present invention also relates to vaccines for pseudorabies disease containing the same, methods for production of the same and methods for use of the same.

63 Claims, 10 Drawing Figures

PSEUDORABIES VIRUS MUTANTS, VACCINES CONTAINING SAME, METHODS FOR THE PRODUCTION OF SAME AND METHODS FOR THE USE OF SAME

FIELD OF INVENTION

The present invention relates to pseudorabies virus mutants containing deletion and/or insertion mutations in a major viral glycoprotein gene, such that no antigenic polypeptides encoded by the viral gene are produced. As a result, animals vaccinated with such do not develop antibodies to the viral glycoprotein and can be distinguished from animals infected with pseudorabies virus field strains and known pseudorabies virus vaccine strains. The present invention also relates to vaccines for pseudorabies disease containing the same, methods for production of the same and methods for use of the same.

BACKGROUND OF INVENTION

I. Pseudorabies Disease

Pseudorabies, a highly contagious disease of swine and other livestock, such as cattle, sheep, and goats, is caused by *Herpesvirus suis* (hereinafter "pseudorabies virus" or "PRV"). In swine, the disease causes respiratory illness and encephalitis which may progress to death. Other common consequences of infection in swine are abortions, neonatal demise, reduced litter size, and slower growth rates. In other livestock, most notably cattle, PRV infection almost invariably proceeds to a lethal encephalitis.

Pseudorabies has become a major threat and cause of economic loss to the swine industry throughout the world. There is also considerable alarm over the spread of pseudorabies to cattle and other farm animals. Within the last ten years, economic losses have escalated because of the emergence of more virulent strains of PRV and the widespread dissemination of the disease. Today, it is estimated that 8.0% of the 80 million hogs on farms in the United States are infected, in comparison to less than 0.8% a decade ago.

The clinical symptoms and consequences of PRV infection may be moderated or prevented by the use of vaccines comprising either killed or modified live, i.e., attenuated strains of PRV. However, most existing vaccines have failed to control the spread of pseudorabies disease because of a unique biological property of PRV and the other alpha herpesviruses, such as herpes simplex virus types 1 and 2 (hereinafter "HSV-1" and "HSV-2", respectively), vericella-zoster, infectious bovine rhinotracheitis virus, marmoset herpesvirus, and equine herpesvirus type 1.

More specifically, alpha herpesviruses have the special ability to enter into a dormant state in neural tissues. That is, as an animal recovers from the initial generalized infection, alpha herpesviruses retreat to portions of the nervous system where they become quiescent and impervious to the body's immune defenses. This dormant infection, i.e., latency, may be unexpectedly reactivated, resulting in recrudescence of disease or in a contagious condition known as the carrier state, wherein the infected animal shows no outward symptoms of the disease but can transmit or "shed" infectious alpha herpesviruses intermittently, so as to cause the spread of infection and epidemic outbreaks.

II. Known Modified Live Virus PRV Vaccines

Previously, modified live virus PRV vaccines have been produced by multiple passages of the virus in chick and/or monkey tissue culture cells (see: Skoda, R., Brauner, I., Sadecky, E., and Mayer V., *Acta Virol.* 8: 1-9 (1964) and Bartha, A., *Magy. Allatorv. Lapja* 16: 42-45 (1961)). During tissue culture passages, mutations accumulate as the virus adapts to its new environment. These undefined mutations adversely affect virus reproduction in the natural host, resulting in virus attenuation.

A problem with the above-described modified live virus PRV vaccines is that the animal ofter becomes a carrier of the dormant vaccine virus. As a result, usage of these vaccines can result in two undesirable situations which impede their safety and effectiveness. First, abortions, stillbirth, and fatal infections in newborns can be caused by some vaccine viruses as they are shed by vaccinated carriers. Second, the repeated circulation of vaccine virus within a herd can result in a reversal of the process of attenuation such that the vaccine virus reverts to the pathogenic parent stain. Under such circumstances, widespread vaccination will undesirably promote the dissemination of the disease.

In addition to the above-described disadvantages, the previously known PRV vaccines, while substantially minimizing symptoms of illness, do not prevent the animal from acquiring a dormant infection with pathogenic field strains. Thus, despite vaccination, an animal may become a carrier of the disease and transmit it to susceptible animals. These carriers of the disease, when moved between farms and market, will shed not only the dormant vaccine virus as discussed above, but also the disease virus. This results in the undesirable transmission of the disease across geographic barriers and state boundaries.

In order to overcome the above-described disadvantages, temperature-resistant pseudorabies viruses which fail to produce a functional thymidine kinase (hereinafter "TK") enzyme as a result of either a mutagen-induced mutation or a deletion in the thymidine kinase gene (hereinafter "tk gene") were developed (see: U.S. Pat. No. 4,514,497, which U.S. patent is incorporated by reference herein in its entirety).

Nonetheless, the dormancy feature of PRV makes it difficult to effect eradication of the disease through the application of quarantine measures which are intended to prevent the spread of the disease by the isolation of infected herbs and the slaughter of infected animals. That is, with existing vaccines it is difficult to determine whether a specific animal, which does not show symptoms of illness, is a carrier of a dormant PRV since usage of most current vaccines mask infections. Hence, since animals which appear healthy may actually be carriers and thus spreaders of PRV, it is important to be able, even after vaccination, to identify infected animals and herds so as to be able to apply quarantine measures. Embodiments of the present invention were developed in order to meet this need.

Moreover, Federal regulations require that swine intended for interstate movement for market or resale must be tested and shown not to be carriers of PRV (i.e., sero-positive for PRV). With all current killed and modified live pseudorabies virus vaccines, a producer who is forced by the circumstances of PRV infection within his herd to vaccinate the susceptible animals finds himself in a position of severe economic disadvantage since the vaccination of the entire stock will result in a positive serological test for PRV. In addition, revaccination to enhance protection will further increase PRV antibody titers. As a result, the farmer's ability to sell his stock is severely restricted.

A vaccine that can safely be administered, protects livestock from disease and dormant infections caused by field strains of PRV, and yet, does not produce a positive test for PRV would allow vaccination programs to be pursued unhindered by the fear of quarantine. The producer could then minimize losses within his own herd, while the animal health authorities could continue with effective, and no longer excessive, control measures. Embodiments of the present invention were also developed in order to meet these needs.

III. The Genomes of PRV Strains

The genomes of PRV strains consist of linear, double-stranded, noncircularly permutated DNA molecules, approximately 146 kilobase pairs (hereinafter "Kbp") in size. Analyses of the genomes of virulent strains of PRV by electron microscopy as well as by restriction nuclease enzymes has shown that they all contain a sequence of DNA, designated as the short unique (hereinafter "$U_S$") sequence, about 10 Kbp in size. The $U_S$ sequence is bracketed by inverted repeat and terminal repeat sequences (hereinafter "$IR_S$" and "$TR_S$", respectively), each about 15 Kbp in size (see: FIG. 1). Another unique sequence, i.e., the long unique (hereinafter "$U_L$") sequence, which is about 111 Kbp in size, comprises the remainder of the molecule.

The genomes of virulent PRV strains are classified as Class D DNA molecules. This is because the $U_S$ region of the genome, which is bracketed by the $IR_S$ and $TR_S$ regions, is found in two orientations relative to the $U_L$ region. The PRV DNA molecules isolated from such virions contain equimolar amounts of these two isomeric forms. Digestion of the DNA with restriction nucleases that do not cut within the $IR_S$ and $TR_S$ regions (e.g., with BglII; see: FIG. 1) produce, in addition to the molar fragments originating entirely from the unique regions of the genome, the two half-molar terminal fragments, BglII-D and BglII-E, and, also, two half-molar fragments which span the repeats and the unique sequences (i.e., BglII-A). In FIG. 1, only one BglII-A fragment is shown, but, in fact, there are two fragments of almost the same size which comigrate.

Restriction enzyme cleavage maps of virulent laboratory strains of PRV have been described (see: Ben-Porat, T. and Kaplan, A. S., In: *The Herpesviruses,* Ed. Roizman, B. (Plenum Press, New York), Vol 3. pp. 105–173 (1985)).

The restriction maps for the KpnI, BamHI, and BglII fragments for the typical PRV(Kaplan) strain are shown in FIG. 1 (see: Lomniczi, B., Blankenship, M. L., and Ben-Porat, T., *J. Virol.* 49: 970–979 (1984)). The KpnI and BamHI restriction patterns for the virulent Aujeszky strain of PRV (ATCC No. VR-135), which closely resembles that of the PRV(Kaplan) strain are shown in FIG. 3, lanes 3 and 8 of U.S. Pat. No. 4,514,497. Restriction patterns for more than 90 additional field strains of PRV isolated from various regions of the United States, Europe, and Taiwan have been described (see: Gielkins, A. L. J., van Oirschot, J. T., and Berns, A. J. M., *J. Gen. Virol.* 66: 69–82 (1985); Kit, S., Kit, M., Lawhorn, B., and McConnell, S., In: *High-Technology Route to Virus Vaccines,* Eds. Dreesman, G. R., Bronson, J. G., and Kennedy, R. C. (American Society of Microbiology, Washington, D.C.), pp. 82–99 (1985); Lomniczi, B., Blankenship, M. L., and Ben-Porat, T., *J. Virol.* 49:970–979 (1984); Paul, P. S., Mengeling, W. L., and Pirtle, E. C., *Arch. Virol.* 73: 193–198 (1982); Pirtle, E. C., Wathen, M. W., Paul, P. S., Mengeling, W. L., and Sacks, J. M., *Am. J. Vet. Res.* 45: 1906–1912 (1984); and Pritchett, R. F., Bush, C. E., Chang, T. J. Wang, J. T., and Zee, Y. C., *Am. J. Vet. Res.* 45: 2486–2489 (1984)). Although the restriction patterns are generally similar to those shown for the Aujeszky strain of PRV (see: FIG. 3, lanes 3 and 8 of U.S. Pat. No. 4,514,497), cleavage pattern variations are demonstrable which distinguish different field isolates from one another. One type of variation involves the loss or gain of restriction endonuclease cleavage sites. For example, KpnI fragments of 3.15 Kbp and 10.7 Kbp are found in three Taiwan isolates, but not in the United States and European strains. Instead, the latter strains have a 13.8 Kbp KpnI fragment (KpnI-C), indicating that the Taiwanese strains have an additional KpnI cleavage site in the KpnI-C fragment (see: Pritchett, R. F., Bush, C. E., Chang, T. J., Wang, J. T., and Zee, Y. C., *Am. J. Vet. Res.* 45: 2486–2489 (1984)).

A second type of variation, which occurs at higher frequency for fragments mapping in the $IR_S$ and $TR_S$ regions of the PRV genome, involves sequence additions or deletions from existing fragments. This type of heterogeneity is particularly noticeable for the BamHI-5 of KpnI-K fragment of PRV strains and results from reiteration of sequences in these fragments.

A third type of variation involves minor changes in the size of homologous fragments. Since no fragments are lost and no new fragments are generated that could account for these molecular weight shifts, these variations are believed to result from small additions or deletions in preexisting fragments rather than by the addition or loss of restriction endonuclease cleavage sites.

The various PRV strains that have been studied have been isolated from epizootically unrelated outbreaks of pseudorabies and are highly virulent. This demonstrates that the above-described variations in restriction nuclease patterns are unrelated to PRV viability or virulence.

The restriction nuclease patterns of several attenuated vaccine strains of PRV, isolated after repeated passage in tissue culture, have also been described. Examples of these are the Bartha A57 and K strains, isolated in Hungary, the SUCH and Bucharest(BUK) strains, isolated in Romania (see: Zuffa, A. and Salaj, J., *Veterinarni Medicina* 17: 201–210 (1972)), derivatives of the Bucharest strains, e.g., the Norden, PRV(BUK-5), and PRV(BUK-7) strains (see: Paul, P. S., Mengeling, W. L., and Pirtle, E. C., *Arch. Virol.* 73: 193–198 (1982); U.S. Pat. No. 4,514,487; and Kit, S., Kit, M., and Pirtle, E. C., *Am. J. Vet. Res.* 46: 1359–1367 (1985)), and the NIA-4 strain, a derivative of the virulent NIA-3 strain isolated in Ireland (see: Baskerville, A., McFerran, J. B., and Dow, C., *Vet. Bull.* 43: 465–480 (1973)).

The KpnI and BamHI restriction patterns of the PRV(BUK-5) strain are shown in FIG. 3, lanes 2 and 7 of U.S. Pat. No. 4,514,497. The sizes of the KpnI, BamHI, and BglII restriction fragments of the PRV(BUK-5) and PRV(BUK-7) strains are summarized in Table 1, infra (see: U.S. Pat. No. 4,514,497)).

FIG. 3 of U.S. Pat. No. 4,514,497 demonstrates that the DNA restriction patterns of the virulent Aujeszky strain of PRV and the attenuated PRV(BUK-5) strain differ in the following three ways. First, the attenuated PRV(BUK-5) DNA contains several restriction fragments (e.g., BamHI-10B, BamHI-0, and KpnI-X) which are not present in the DNA of the virulent Aujeszky strain of PRV. These altered fragments in the Bucharest vaccine strains of PRV, such as Norden and PRV(BUK-5), result from the fact that a sequence normally present at the end of the $U_L$ region in all of the virulent PRV strains is also found in inverted form at the junction of the $U_L$ and the $IR_S$ regions in the Bucharest strains. As a result, both the $U_L$ and $U_S$ regions of the Bucharest strains can invert relative to each other to produce four DNA isomers (i.e., Class E DNA) (see: Lomniczi, B., Blankenship, M. L., and Ben-Porat, T., *J. Virol.* 49: 970–979 (1984)).

Second, the BamHI-11 fragment of PRV(BUK-5) migrates more slowly during gel electrophoresis and, hence, is larger in size than the BamHI-11 fragment of the Aujeszky strain of PRV. The BamHI-11 fragment encodes the PRV tk gene and other genes. Nucleotide sequencing studies have demonstrated that the increased size of the PRV(BUK-5) BamHI-11 fragment results from a reiteration of about 200 base pairs (hereinafter "bp") in the noncoding sequence that bridges the PRV tk gene and the next gene downstream from the PRV tk gene. The reiterated sequence contains a polyadenylation (AATAAA) signal (see: Kit, S., Kit, M., and Otsuka, H. In: Herpesvirus, Ed. Rapp, F. (Alan R. Liss, Inc., New York), pp. 311–327 (1984)). This reiterated sequence is not observed in the BamHI-11 fragment of the Aujeszky strain of PRV.

The third difference is especially important. The attenuated Bucharest, Bartha, and NIA-4 vaccine strains of PRV all possess a deletion of approximately 4 Kbp in the KpnI-I fragment. This corresponds to a loss of the entire BamHI-12 fragment and adjacent sequences from the BamHI-7 fragment (see: FIG. 1). This deletion is characteristic of attenuated strains and has not been observed in the many virulent PRV strains which have been isolated in the United States, Europe, and Taiwan. This deletion in the KpnI-I fragment accounts, at least in part, for the reduced virulence of the attenuated Bartha, Bucharest, and NIA-4 PRV strains. Thus, marker transfer experiments which restore all of the KpnI-I sequences of field strains to the attenuated vaccine strains have been found to restore virulence, while the genetic engineering of deletions in this KpnI-I fragment of virulent PRV strains has been found to produce an attenuated PRV (see: Lomniczi, B., Watanabe, S., Ben-Porat, T., and Kaplan, A. S., *J. Virol.* 52: 198–205 (1984); Lomniczi, B., Blankenship, M. L., and Ben-Porat, T., *J. Virol.* 49: 970–979 (1984), Berns, A., van den Ouweland, A., Quint, W., van Oirschot, J., and Gielkens, A. L. J., *J. Virol.* 53: 89 ∝ 93 (1985); Gielkens, A. L. J., van Oirschot, J. T., and Berns, A. J. M., *J. Gen. Virol.* 66: 69–82 (1985); and Pritchett, R. F., Bush, C. E., Chang, T. J., Wang, J. T., and Zee, Y. C., *Am. J. Vet. Res.* 45: 2486–2489 (1984)). The sequences deleted from the attenuated vaccine strains but which are present in virulent PRV field strains encode a minor PRV glycoprotein, designated gI or gA (see: Mettenleiter, T. C., Lukacs, N., and Rziha, H. J., *J. Virol.* 53: 52–57 (1985); and Mettenleiter, T. C., Lukacs, N., and Rziha, H. J., *J. Virol.* 56: 307–311 (1985)). The above-described observations indicate that the products of genes encoded by KpnI-I(BamHI-12+7) sequences of PRV are markers for PRV virulence.

Recently, it has been found that the Bartha K strain of PRV contains a "leaky" mutation in a PRV gene encoding a glycoprotein with an apparent molecular weight of about 92,000 to 98,000 daltons (hereinafter "g92") (see: Paul, P. S., Mengeling, W. L. and Pirtle, E. C., *Arch. Virol.* 73: 193–198 (1982)). That is, g92 glycoprotein is produced at about 10% of its normal levels. This "leaky" mutation may account, in part, for the reduced virulence of the Bartha K strain of PRV. This "leaky" mutation in the PRV g92 gene is not found in the Bartha A57 strain (see: Ben-Porat, T., DeMarchi, J., Pendrys, J., Veach, R. A. and Kaplan, A. S., *J. Virol.* 57: 191–196 (1986)).

It is to be emphasized, however, that all of the conventional attenuated vaccine strains, that is Bucharest and its derivatives, Bartha and its variants, and NIA-4, are unaltered in their tk gene, i.e., they all produce fully functional, virus-specific TK enzyme.

Further attenuation of the above-described PRV strains has been achieved by the isolation of spontaneous or mutagen-induced $tk^-$ viruses, or by the isolation of $tk^-$ deletion mutants of PRV (see: U.S. Pat. No. 4,514,497; Kit, S., Kit, M., and Pirtle, E. C., *Am. J. Vet. Res.* 46: 1359–1367 (1985); and Lomniczi, B., Watanabe, S., Ben-Porat, T., and Kaplan, A. S., *J. Virol.* 52: 198–205 (1984)). Thus, virulence of PRV is multigenic, i.e., virulence of PRV is the result of more than one active gene.

The restriction pattern of a PRV mutant with a deletion in the tk gene, i.e., PRV(BUK-dl 3) (ATCC No. VR-2074), is shown in FIG. 3, lanes 1 and 6 of U.S. Pat. No. 4,514,497. From FIG. 3 therein, it can be seen that the BamHI and KpnI restriction patterns of the $tk^-$ deletion mutant, i.e., PRV(BUK-dl 3), are the same as that of the $tk^+$ parental strain, i.e., PRV(BUK-5), with the exception that the BamHI-11 fragment, designated dl 11 and the KpnI-$J_L$ fragments, which encode the PRV tk gene (see: FIG. 2, plasmid pBK-$J_L$), migrate more rapidly and, hence, are smaller by about 150 bp in the PRV(BUK-dl 3) deletion mutant than in the parental PRV(BUK-5) strain (Compare FIG. 3 lanes 2 and 7 with lanes 1 and 6 of U.S. Pat. No. 4,514,497).

IV. Pseudorabies Virus Envelope Proteins

Pseudorabies virus particles are approximately 180 nm in diameter and, like other herpesviruses, comprise an icosahedral capsid (100 nm in diameter) composed of 162 capsomers surrounded by a lipoprotein envelope. Removal of this viral envelope with nonionic detergents, such as Triton X-100 or Nonidet P40, allows the separation of the envelope from the viral nucleocapsid, which contains all of the DNA and about half of the viral proteins. The nucleocapsid comprises three major proteins, about 142,000, 35,000, and 32,000 daltons in size, another protein of about 62,000 daltons in size, and about 12 other minor proteins ranging in size from 10,000 to 115,000 daltons. The envelope contains the remainder of the viral proteins, which include at least seven glycoproteins and a nonglycosylated protein. As with other alpha herpesviruses, such as HSV-1, the envelope proteins, and their precursors, have a role in inducing cellular and humoral immune responses; they function in virus penetration into infected cells; and they promote virus-cell fusion.

Sedimentation analyses and chromatographic studies of the PRV envelope proteins have revealed that several of them are complexed with one another, with some being covalently linked via disulfide bridges. Further analyses of the envelope proteins by immunoprecipitation with monoclonal antibodies has shown that the viral glycoproteins covalently linked by disulfide bridges are gIIa (molecular weight of about 120,000–125,000 daltons), gIIb (molecular weight of about 68,000–74,000 daltons), and gIIc (molecular weight of about 52,000–58,000 daltons) (see: Hampl, H., Ben-Porat, T., Ehrlicher, L., Habermehl, K. O., and Kaplan, A. S., *J. Virol.* 52: 583–590 (1984); and Lukacs, N., Thiel, H. J., Mettenleiter, T. C., and Rhiza, H. J., *J. Virol.* 53: 166–173 (1985)). All three glycoproteins share extensive sequence homology, as indicated by the identity of their antigenic determinants and by partial polypeptide mapping. Thus, they probably originate from a single precursor protein, i.e., gIIa.

Three minor glycoproteins, i.e., gI (molecular weight of about 115,000 to 120,000 daltons), gIV (molecular weight of about 98,000 daltons), and gV (molecular weight of about 62,000 daltons), form a noncovalently linked complex with p115, i.e., a nonglycosylated protein (molecular weight 115,000 daltons). Another major glycoprotein, i.e., gIII (apparent molecular weight of 92,000 to 98,000 daltons) is not complexed with any other protein.

All of the above-described glycoproteins react with monoclonal antibodies, indicating that they are exposed on the surface of the PRV particles. Further, monoclonal antibodies to gIII inhibit virus adsorption and neutralize virus infectivity in the absence of complement.

Molecular hybridization experiments have been carried out with cloned HSV-1 DNA probes to investigate whether the major HSV-1 glycoprotein genes, i.e., HSV-1 gB, HSV-1 gC, and HSV-1 gD, share nucleotide sequence homology with any of the PRV glycoprotein genes. These studies have revealed that HSV-1 DNA fragments representing HSV-1 gB coding sequences hybridize specifically to PRV DNA which encodes the gII complex, but that HSV-1 DNA fragments representing HSV-1 gC and HSV-1 gD do not specifically hybridize to PRV DNA (see: Robbins, A. K., Gold, C., Enquist, L. W., Whealy, M. E. and Watson, R. J., Abstracts presented at the Tenth International Herpesvirus Workshop, Ann Arbor, Mich. Aug. 11–26, 1985, p. 130). Genetic analyses and studies with monoclonal antibodies have also shown that the PRV gene encoding the gII glycoprotein complex maps at the left end of the $U_L$ region of the PRV genome, in the BamHI-1 fragment, at about 0.110 to 0.128 map units (see: FIG. 1 and Wathen, M., Holland, L., Glorioso, J., and Levine, M. Abstracts presented at the Tenth International Herpesvirus Workshop, Ann Arbor, Mich., Aug. 11–26, 1985, p. 140). This location is close to that of the PRV genes encoding the PRV-specific DNA polymerase and DNA binding proteins. The HSV-1 gB gene is also located next to the HSV-1-specific DNA polymerase and DNA binding protein genes. This further demonstrates the homologous relationship between the PRV gII gene and the HSV-1 gB gene.

The HSV-1 gB gene is the only HSV-1 glycoprotein gene known to have an essential role in viral replication and penetration. That is, temperature-sensitive mutants exist with alterations in the HSV-1 gB gene (see: Spear, P. G. In: *The Herpesviruses,* Ed. Roizman, B. (Plenum Press, New York), Vol. 3, pp. 315–356 (1985); Holland, T. C., Homa, F. L., Marlin, S. D., Levine, M., and Glorioso, J., *J. Virol.* 52: 566–574 (1984); and Marlin, S. D., Holland, T. C., Levine, M., and Glorioso, J. C., *J. Virol.* 53: 128–136 (1985)). This finding suggests that the PRV gII gene may also be essential for PRV replication.

The gene encoding PRV gI has been mapped in the $U_S$ region of the PRV genome in the BamHI-7 and BamHI-12 fragments (see: FIG. 1). Cell-free translation studies on PRV messenger RNAs transcribed from this region have shown that two polypeptides, with molecular weights of about 78,000 and 83,000 daltons, are transcribed and translated from the BamHI-12 and BamHI-7 fragment. These two polypeptides are precipitated by monoclonal antibodies directed against PRV gI, indicating that the 78,000 and 83,000 molecular weight polypeptides are nonglycosylated gI precursors (see: Mettenleiter, J. C., Lukas, N., and Rhiza, H. J., *J. Virol.* 53: 52–57 (1985)). As indicated previously, the apparent molecular weight of the mature glycosylated gI is about 115,000 to 120,000 daltons.

As discussed above, it has been shown that expression of PRV gI is not obligatory for PRV infectivity, but that gI expression is important for PRV virulence (Mettenleiter, T. C., Lukacs, N., and Rhiza, H. J., *J. Virol.* 56: 307–311 (1985); Berns, A. J. M., van den Ouweland, A., Quint, W., van Oirshot, J. T., and Gielkens, A. L. T., *J. Virol.* 53: 89–93 (1985); Lomniczi, B., Blankenship, M. L., and Ben-Porat, T., *J. Virol.* 49: 970–979 (1984)). That is, three vaccine strains of PRV, namely, Bucharest, Bartha, and NIA-4, lack the BamHI-12 fragment, exhibit deletions in the BamHI-7 fragment, and fail to synthesize gI. The $tk^-$ deletion mutant PRV(BUK-dl 3) also lacks the BamHI-12 fragment and has a deletion in the BamHI-7 fragment. This is as expected since it was derived from the Bucharest strains PRV(BUK-5) and PRV(BUK-7) (see: U.S. Pat. No. 4,514,497 and Kit, S., Kit, M., Pirtle, E. C., *Am. J. Vet. Res.* 46: 1359–1367 (1985)). In addition, attenuation of virulent PRV strains has been engineered by making DNA sequence deletions in the BamHI-7 and BamHI-12 fragments of PRV DNA (see: European Patent Publication No. 0141458). On the other hand, most of the virulent laboratory and field strains of PRV contain intact BamHI-7 plus BamHI-12 DNA sequences and therefore express PRV gI. (see: Gielkens, A. L. J., van Oirschot, J. T., and Berns, A. J. M., *J. Gen. Virol.* 66: 69–82 (1985); Pirtle, E. C., Wathen, M. W., Paul, P. S., Mengeling, W. L., and Sacks, J. M., *Am. J. Vet. Res.* 45: 1906–1912 (1984); and Pritchett, R. F., Bush, C. E., Chang, T. J., Wang, J. T., and Zee, Y. C., *Am. J. Vet. Res.* 45: 2486–2489 (1984)).

Cells infected with PRV excrete large amounts of an 89,000 molecular weight sulfated glycoprotein into the extracellular fluid. The sulfated glycoprotein is a nonstructural PRV protein, i.e., it is not a component of PRV particles. Its function is unknown. No major intracellular polypeptides with the same molecular weight as this sulfated glycoprotein have so far been detected. This sulfated PRV glycoprotein has been designated gX, and maps in the $U_S$ region of the PRV genome, in a 2 Kbp DNA fragment which contains parts of BamHI-10 and BamHI-7 fragments (see: Pennington, T. H. and McCrae, M. A., *J. Gen. Virol.* 34: 155–165 (1977); Kerr, C. L. and Pennington, T. H., *J. Gen. Virol.* 65: 1033–1041 (1984); and Rea, T. J., Timmins, J. G., Long, G. W., and Post, L. E., *J. Virol.* 54: 21–29 (1985)). Thus, the PRV gX gene is encoded in the $U_S$ region of the PRV genome in the BamHI-7 plus the BamHI-10 fragments and the PRV gI gene, which is also encoded in the $U_S$ region of the PRV genome, is encoded to the right of the PRV gX gene in the BamHI-7 plus the BamHI-12 fragments (see: FIG. 1).

The region of the PRV genome which encodes for gX has been sequenced and found to include an open reading frame coding for 498 amino acids, flanked by sequences which contain features common to eucaryotic promoters and polyadenylation signals. The predicted molecular weight of the coded amino acid sequence is 53,700 daltons which is considerably smaller than the apparent mass of the 70,000 molecular weight precursor seen after in vitro translation of the gX messenger RNA. This is believed to be due to the high percentage (8.8%) of proline residues in the sequence (see: Rea, T. J., Timmins, J. G., Long, G. W., and Post, L. E., *J. Virol.* 54: 21-29 (1985)).

The gene for yet another PRV glycoprotein, designated gp50, has been mapped at 0.813-0.832 map units, which is at least partly within the same BamHI-7 nucleotide sequences as gX (see: FIG. 1). However, unlike gX, gp50 is present on the surface of PRV particles. gp50 was identified through the isolation of a PRV variant, mar197-1, which was resistant to a neutralizing monoclonal antibody (MCA50-1) directed against wild-type PRV gp50. The mar197-1 mutant is completely resistant to neutralization with the MCA50-1 antibody in the presence or absence of complement, but is neutralized by polyvalent immune sera. The mar197-1 mutant synthesizes and processes gp50 normally, but the mutation prevents the binding and immunoprecipitation of gp50 by the MCA50-1 antibodies. This demonstrates that the mutation is within the structural portion of the gp50 gene affecting the epitope of the monoclonal antibody. The location of the genes for gX and gp50 within the same small region of the PRV genome raises the possibilities that the two glycoprotein genes map very close to each other, or that the glycoproteins are somehow related (see: Wathen, M. W. and Wathen, L. M. K., *J. Virol.* 51: 57-62 (1984)).

A PRV glycoprotein with an apparent molecular weight of 82,000 daltons (hereinafter "gp82") has been mapped in the $U_L$ region of the PRV genome at 0.290 to 0.309 map units on the PRV genome. This is within the BglII-B fragment near the junction of the BamHI-2 and BamHI-1 fragments (see: FIG. 1 and Wathen, M. W., Holland, L., Glorioso, J., and Levine, M. Abstracts presented at the Tenth International Herpesvirus Workshop, Ann Arbor, Mich., Aug. 11-26, 1985, p. 140). gp82 is not essential for replication in cell culture and the absence of gp82 is associated with an altered plaque morphology (syncytial formation). Using monoclonal antibodies raised against gp82, it has been determined that gp82 probably corresponds to g92 (see: Wathen, L. M. K., Platt, V. B., Wathen, M. W., van Deusen, R. A., Whetstone, C. A. and Pirtle, E. C., *Virus Research* 4: 19-29 (1985) and the studies herein).

Finally, the PRV gene encoding the glycoprotein with an apparent molecular weight of about 92,000 to 98,000 daltons i.e., g92, has been mapped at about 0.38-0.42 map units on the PRV genome. This is within the BglII-B fragment near the junction of the BamHI-2 and BamHI-9 fragments (see: FIG. 1 and Robbins, A. K., Weis, J. H., Enquist, L. W., and Watson, R. J., *J. Mol. Appl. Genet.* 2: 485-496 (1984)). It should be noted that this map location is at the opposite end of the BamHI-2 fragment from the map location assigned to gp82 by Wathen et al (see: Wathen, L. M. K., Platt, V. B., Wathen, M. W., van Deusen, R. A., Whetstone, C. A. and Pirtle, E. C., *Virus Research* 4: 19-29 (1985)).

Nucleotide sequencing studies on the PRV g92 gene have been described (see: Robbins, A. K., Presentations at the Ninth International Herpesvirus Workshop, Seattle, Wash., Aug. 24-29, 1984). These studies have revealed that the DNA fragment spanning the BamHI-2 and BamHI-9 junction contain an open reading frame encoding 479 amino acids. The putative translational start signal is at the NcoI restriction site at 5.2 map units on plasmid pBUK:StuI2/PstI (see: FIG. 4). A putative translational stop codon (TGA) is found 57 nucleotides downstream from the BamHI site connecting fragments BamHI-2 and BamHI-9 (6.6 map units on plasmid pBUK:StuI2/PstI; see: FIG. 4). Thirty-one nucleotides downstream from the TGA stop signal is a consensus "AATAAA" polyadenylation signal.

The molecular weight of the nonglycosylated protein predicted from the g92 sequence is 51,000 daltons. This 51,000 molecular weight polypeptide contains eight potential glycosylation sites, i.e., asparagine-X-threonine or asparagine-X-serine sequences. g92 is believed to represent a mature, processed, and fully glycosylated form of a 51,000 molecular weight precursor. A partially glycosylated precursor of PRV g92, with an apparent molecular weight of about 74,000 to 79,000 daltons, (hereinafter "g74") has also been observed through the use of the drug monensin, which inhibits glycoprotein processing (see: Lukacs, N., Thiel, H. J., Mettenleiter, T. C. and Rziha, H. J., *J. Virol* 53: 166-173 (1985)).

Antisera which specifically reacts, in immunoprecipitation and Western blot analyses, with both g92 and g74, have been obtained by immunizing rabbits with a denatured g74 polypeptide excised after sodium dodecyl sulfate-polyacrylamide gel electrophoresis assays (SDS-PAGE) (see: Robbins, A. K., Weis, J. H., Enquist, L. W., and Watson, R. J., *J. Mol. Appl. Genet.* 2: 485-496 (1984)). In contrast, antisera raised in rabbits against the denatured g110-g92 group of PRV proteins isolated from SDS-PAGE gels reacts in immunoprecipitation and Western blot analyses predominantly with proteins of apparent molecular weights of 110,000, 92,000, and 55,000 daltons. These experiments, and sucrose gradient centrifugation experiments to be described herein, suggest that g92, and its precursor, g74, which map at the BamHI-2/BamHI-9 junction, correspond to glycoprotein gIII (see: Hampl, H., Ben-Porat, T., Ehrlicher, L., Habermehl, K. O. and Kaplan, A. S., *J. Virol.* 52: 583-590 (1984) and Lukacs, N., Thiel, H. J., Mettenleiter, T. C. and Rziha, H. J., *J. Virol.* 53: 166-173 (1985)).

The production of glycoprotein gIII has been demonstrated in cells infected with virulent PRV strains such as the Rice strain, the Ind-F strain, the Iowa 62-26 strain, the Kaplan strain, the Becker strain and the Phylaxia strain, and with attenuated PRV strains such as the Bartha A57 strain, the Bucharest(Norden) strain and the NIA-4 strain (see: Rea, T. J., Timmins, J. G., Long, G. W. and Post, L. E., *J. Virol.* 54: 21-29 (1985); Wathen, M. W. and Wathen, L. M. K., *J. Virol.* 51: 57-62 (1984); Wathen, L. M. K., Platt, K. B., Wathen, M. W., Van Duesen, R. A., Whetstone, C. A. and Pirtle, E. C., *Virus Res.* 4: 19-29 (1985); Lukacs, N., Thiel, H. J., Mettenleiter, T. C. and Rziha, H. J., *J. Virol.* 53: 166-173 (1985); Robbins, A. K., Weis, J. H., Enquist, L. W. and Watson, R. J., *J. Mol. Appl. Genet.* 2: 485-496 (1984); Hampl, H., Ben-Porat, T., Ehrlicher, L., Habermehl, K. O. and Kaplan, A. S., *J. Virol.* 56: 307-311 (1985)).

As discussed above, the Bartha K strain underproduces glycoprotein g92. That is, the Bartha K strain only produces about 10% of the normal levels of the g92 glycoprotein (see: Ben-Porat, T., De Marchi, J., Pendrys, J., Veach, R. A. and Kaplan, A. S., *J. Virol.* 57: 191-196 (1986)). Nonetheless, this amount of glycoprotein g92 should be sufficient to elicit antibodies to glycoprotein g92 in animals vaccinated with such. As a result, antisera obtained from animals vaccinated with the Bartha K strain should still recognize the same antigens as antisera from pigs vaccinated with other PRV strains. Hence, it should not be possible to distinguish animals vaccinated with the Bartha K strain from animals infected with other PRV vaccines or any PRV field strain. Furthermore, reversion of the Bartha K strain to one which produces normal levels of the g92 glycoprotein is not precluded.

In the present invention, it has been possible for the first time to provide a PRV vaccine, wherein animals vaccinated with such, due to deletion and/or insertion mutations in the g92 gene, do not produce any antigenic polypeptide encoded by the g92 gene and can not revert to the production of g92 antigen. As a result, animals vaccinated with such can be distinguished from animals infected with other PRV vaccines or any PRV field strain, so as to enable the erradication of pseudorabies disease through the application of quarantine measures. Additionally, in the present invention, it has been possible for the first time to provide a PRV vaccine which is both distinguishable from other PRV vaccines and field strains, as discussed above, and which is not only effective in controlling the spread of pseudorabies disease, but wherein the animals vaccinated with such, due to the mutations in the PRV tk gene, are less likely to become a carrier of the vaccine virus and are unlikely to acquire a dormant infection with pathogenic field strains.

SUMMARY OF THE INVENTION

An object of the present invention is to provide a pseudorabies vaccine effective in controlling the spread of pseudorabies disease.

Another object of the present invention is to provide a pseudorabies vaccine wherein the animal vaccinated with such is less likely to become a carrier of either the vaccine virus or a field virus.

Still another object of the present invention is to provide a pseudorabies vaccine, wherein the vaccine virus is distinguishable from any field strain virus and from other PRV vaccine viruses.

A further object of the present invention is to provide a pseudorabies vaccine, wherein animals vaccinated with such can be distinguished from animals infected with any field strain virus or vaccinated with other PRV vaccine viruses.

A still futher object of the present invention is to provide a pseudorabies virus which fails to produce any antigenic g92 polypeptides as a result of a deletion and/or insertion mutation in the g92 gene.

An even further object of the present invention is to provide a pseudorabies virus which both fails to produce any functional thymidine kinase enzyme activity as a result of a mutation in the coding sequence of the tk gene and fails to produce any antigenic g92 polypeptides as a result of a deletion and/or insertion mutation in the g92 gene.

Another object of the present invention is to provide a pseudorabies vaccine wherein animals vaccinated with such do not develop antibodies to g92 glycoprotein.

Still another object of the present invention is to provide a pseudorabies virus which cannot revert to tk+, is easily distinguished from tk+ pseudorabies virus, and cannot revert to g92+.

Yet still another object of the present invention is to provide a pseudorabies virus which can replicate efficiently at temperatures ranging from 30° C. to 40° C., i.e., inclusive of temperature-resistant viruses.

An additional object of the present invention is to provide methods for the production of a pseudorabies virus which contain deletion and/or insertion mutations in the g92 gene.

Other objects of the present invention will be apparent from the detailed description of the invention hereinafter.

In an embodiment of the present invention, the above-described objects have been met by PRV which fails to produce any antigenic g92 polypeptides as a result of a deletion and/or insertion mutation in the g92 gene, and a vaccine for pseudorabies disease comprising (1) a pharmaceutically effective amount of said virus and (2) a pharmaceutically acceptable carrier or diluent.

In a further embodiment of the present invention, the PRV also fails to produce any functional TK as a result of a mutation in the tk gene.

In another embodiment of the present invention, the PRV also fails to produce any glycoprotein gI as a result of a mutation in the gI gene.

In still another embodiment of the present invention, the PRV is a temperature-resistant virus.

In an additional embodiment of the present invention, the above-described objects have been met by a process for producing a PRV which fails to produce any antigenic g92 polypeptides as a result of an insertion mutation in the g92 gene comprising:

(1) Constructing a hybrid plasmid comprising a cloning vector and a DNA fragment of PRV containing substantially all of the PRV g92 gene and flanking sequences thereof;

(2) Inserting a DNA fragment which encodes a functional selectable gene into the PRV g92 gene of the resulting hybrid plasmid of step (1) such that the functional selectable gene is flanked by DNA sequences of the PRV g92 gene;

(3) Cotransfecting into PRV host cells the hybrid plasmid of step (2) with infectious DNA from a pseudorabies virus which fails to produce the product of the selectable gene, and selecting for PRV recombinants which produce the product of the selectable gene so as to produce PRV mutants which fail to produce any antigenic g92 polypeptides as a result of an insertion mutation in the g92 gene.

In another embodiment of the present invention, the above-described objects have been met by a process for producing a PRV which fails to produce any antigenic g92 polypeptides as a result of a deletion mutation in the g92 gene comprising:

(1) Constructing a hybrid plasmid comprising a cloning vector and a DNA fragment of PRV containing substantially all of the PRV g92 gene and flanking sequences thereof;

(2) Inserting a DNA fragment which encodes a functional selectable gene into the PRV g92 gene of the resulting hybrid plasmid of step (1) such that the functional selectable gene is flanked by DNA sequences of the PRV g92 gene;

(3) Cotransfecting into PRV host cells the hybrid plasmid of step (2) with infectious DNA from a pseudorabies virus which fails to produce the product of the selectable gene, and selecting for PRV which produce the product of the selectable gene;

(4) Deleting DNA sequences from the hybrid plasmid of step (1) such that less than substantially all of the g92 gene is present, while retaining PRV DNA sequences adjacent to each side of the deletion;

(5) Cotransfecting in PRV host cells the resulting hybrid plasmid of step (4) with infectious DNA from the selected PRV of step (3), and selecting for PRV which do not produce the product of the selectable gene so as to produce PRV mutants which fail to produce any antigenic g92 polypeptides as a result of a deletion mutation in the g92 gene.

In a further embodiment, a foreign DNA sequence is inserted in place of the deleted g92 gene sequences in step (4) such that no antigenic g92 polypeptides are produced and such that PRV DNA sequences adjacent to each side of the deleted g92 gene sequences are retained. As a result, the PRV mutants of step (5) fail to produce any antigenic g92 polypeptides as a result of combined deletion and insertion mutations.

In a still further embodiment, step (4) is replaced by step (4′) Inserting a foreign DNA sequence into the plasmid of step (1) such that no antigenic g92 polypeptides are produced and such that PRV DNA sequences adjacent to each side of the insertion are retained. As a result, the PRV mutants of step (5) fail to produce any antigenic g92 polypeptides as a result of an insertion mutation in the g92 gene.

In a preferred embodiment of the present invention, the infectious DNA of step (3) is derived from a PRV mutant which fails to produce any functional thymidine kinase such that the resulting mutants of step (5) are both $tk^-$ and $g92^-$ mutants.

In a still further embodiment of the present invention, the infectious DNA of step (3) is derived from a temperature-resistant pseudorabies virus such that the resulting mutants of step (5) are both temperature-resistant and $g92^-$ mutants.

In yet another embodiment of the present invention, the resulting PRV of step (5) are propagated at a non-permissive temperature for a temperature-sensitive virus so as to select for and produce a temperature-resistant PRV which fails to produce any antigenic g92 polypeptides as a result of a deletion and/or insertion mutation in the g92 gene.

BRIEF DESCRIPTION OF THE DRAWINGS

FIG. 1) was cloned at the unique KpnI site (1.6 map units) of plasmid pMAR-Kpn to produce plasmid pBK-$J_L$. Plasmid pMAR-Kpn is a derivative of plasmid pMAR420 (see: Otsuka, H., Hazen, M., Kit, M., Qavi, H., and Kit, S., *Virol.* 113: 196–213 (1981)). The black bar and solid line represent, respectively, pBR322 and *Herpesvirus tamarinus* nucleotide sequences. Then, pBK-$J_L$ plasmid was cleaved at the StuI restriction site and BglII linkers were ligated to this site to produce pBK-$J_L$(StuI/BglII).

FIG. 2) was cleaved with BglII and KpnI to excise a 3.1 Kbp KpnI to BglII(StuI) fragment (4.8 to 7.9 map units), which was then inserted into plasmid pBUK:Stul2 (see.

FIG. 4 schematically illustrates, by example, the derivation of plasmids pBUK:BglII-B, pBUK:Stu12, pBUK:Stu12/PstI and pBUK:gCdlSal. Plasmid pBUK:BglII-B was constructed by cloning the 31.6 Kbp BglII fragment of PRV(BUK-7) (see: FIG. 1) at the BamHI site of pBR322. Next, BglII linkers were added at the StuI sites of plasmid pBUK:BglII-B (at about 11 and 21 map units) and the resulting BglII/StuI fragment was then transferred to the BamHI site of another pBR322 plasmid to produce plasmid pBUK:-Stu12. Plasmid pBUK:Stu12 was cleaved with PstI and a 4.0 Kbp PstI fragment containing the PRV g92 gene was transferred to the PstI site of pBR322 to produce plasmid pBUK:Stu12/PstI. Finally, a 1.1 Kbp SalI fragment (map units 5.2 to 6.3) was deleted from the g92 gene of plasmid pBUK:Stu12/PstI to produce plasmid pBUK:gCdlSal.

FIG. 5). Lanes 1 and 18 show ClaI-cleaved plasmids pMAR4 (13.4 Kbp), pAGO (6.4 Kbp), and pMH110 (4.4 Kbp), which were used as internal markers (see: Kit, S., Qavi, H., Dubbs, D. R., and Otsuka, H. J., *Med. Virol.* 12: 25-36 (1983)). Lanes 9 and 17 show HindIII lambda phage and HaeIII ΦX174 phage marker fragments.

In FIGS. 7A and 7B, lanes 4, 8, 12 and 16 show reactions of extracts with normal (prebleed) pig sera (NS). The marker proteins used to estimate molecular weights were myosin (205,000), beta-galactosidase (116,000), phosphorylase b (97,400), bovine serum albumin (66,000), ovalbumin (45,000), and carbonic anhydrase (29,000) (Sigma Chemical Co.).

DETAILED DESCRIPTION OF THE INVENTION

Figure 1:
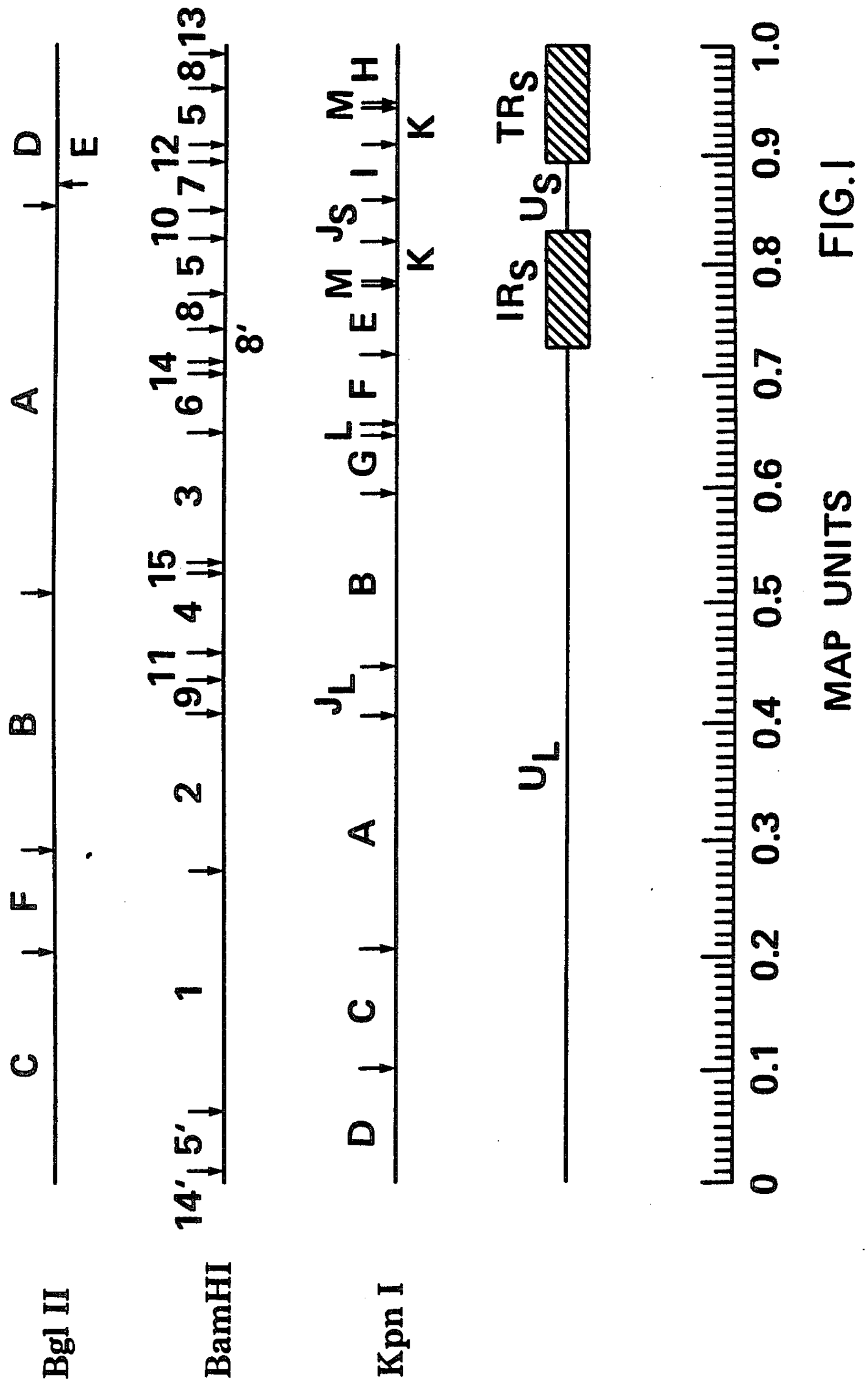
FIG. 1 illustrates the BglII, BamHI, and KpnI restriction nuclease maps for the DNA of virulent pseudorabies virus strains. The inverted repeat ($IR_S$) and terminal repeat ($TR_S$) regions which bracket the unique-short ($U_S$) region of the genome are shown. In addition, the unique-long ($U_L$) region of the genome is shown.

As described above, in an embodiment of the present invention, the above-described objects have been met by PRV which fails to produce any antigenic g92 polypeptides as a result of a deletion and/or insertion mutation in the g92 gene, and a vaccine for pseudorabies disease comprising (1) a pharmaceutically effective amount of said virus and (2) a pharmaceutically acceptable carrier or diluent.

In a further embodiment of the present invention, the PRV also fails to produce any functional TK as a result of a mutation in the tk gene.

In another embodiment of the present invention, the PRV also fails to produce any glycoprotein gI as a result of a mutation in the gI gene.

In still another embodiment of the present invention, the PRV is a temperature-resistant virus.

In an additional embodiment of the present invention, the above-described objects have been met by a process for producing a PRV which fails to produce any antigenic g92 polypeptides as a result of an insertion mutation in the g92 gene comprising:

(1) Constructing a hybrid plasmid comprising a cloning vector and a DNA fragment of PRV containing substantially all of the PRV g92 gene and flanking sequences thereof;

(2) Inserting a DNA fragment which encodes a functional selectable gene into the PRV g92 gene of the resulting hybrid plasmid of step (1) such that the functional selectable gene is flanked by DNA sequences of the PRV g92 gene;

(3) Cotransfecting into PRV host cells the hybrid plasmid of step (2) with infectious DNA from a pseudorabies virus which fails to produce the product of the selectable gene, and selecting for PRV recombinants which produce the product of the selectable gene so as to produce PRV mutants which fail to produce any antigenic g92 polypeptides as a result of an insertion mutation in the g92 gene.

In another embodiment of the present invention, the above-described objects have been met by a process for producing a PRV which fails to produce any antigenic g92 polypeptides as a result of a deletion mutation in the g92 gene comprising:

(1) Constructing a hybrid plasmid comprising a cloning vector and a DNA fragment of PRV containing substantially all of the PRV g92 gene and flanking sequences thereof;

(2) Inserting a DNA fragment which encodes a functional selectable gene into the PRV g92 gene of the resulting hybrid plasmid of step (1) such that the functional selectable gene is flanked by DNA sequences of the PRV g92 gene;

(3) Cotransfecting into PRV host cells the hybrid plasmid of step (2) with infectious DNA from a pseudorabies virus which fails to produce the product of the selectable gene, and selecting for PRV which produce the product of the selectable gene;

(4) Deleting DNA sequences from the hybrid plasmid of step (1) such that less than substantially all of the g92 gene is present, while retaining PRV DNA sequences adjacent to each side of the deletion;

(5) Cotransfecting in PRV host cells the resulting hybrid plasmid of step (4) with infectious DNA from the selected PRV of step (3), and selecting for PRV which do not produce the product of the selectable gene so as to produce PRV mutants which fail to produce any antigenic g92 polypeptides as a result of a deletion mutation in the g92 gene.

In a further embodiment, a foreign DNA sequence is inserted in place of the deleted g92 gene sequences in step (4) such that no antigenic g92 polypeptides are produced and such that PRV DNA sequences adjacent to each side of the deleted g92 gene sequences are retained. As a result, the PRV mutants of step (5) fail to produce any antigenic g92 polypeptides as a result of combined deletion and insertion mutations.

In a still further embodiment, step (4) is replaced by step (4'). Inserting a foreign DNA sequence into the plasmid of step (1) such that no antigenic g92 polypeptides are produced and such that PRV DNA sequences adjacent to each side of the insertion are retained. As a result, the PRV mutants of step (5) fail to produce any antigenic g92 polypeptides as a result of an insertion mutation in the g92 gene.

In a preferred embodiment of the present invention, the infectious DNA of step (3) is derived from a PRV mutant which fails to produce any functional thymidine kinase such that the resulting mutants of step (5) are both tk$^-$ and g92$^-$ mutants.

In a still further embodiment of the present invention, the infectious DNA of step (3) is derived from a temperature-resistant pseudorabies virus such that the resulting mutants of step (5) are both temperature-resistant and g92$^-$ mutants.

In yet another embodiment of the present invention, the resulting PRV of step (5) are propagated at a non-permissive temperature for a temperature-sensitive virus so as to select for and produce a temperature-resistant PRV which fails to produce any antigenic g92 polypeptides as a result of a deletion and/or insertion mutation in the g92 gene.

The g92 glycoprotein is approximately 1500 bp in size. The deletion and/or insertion mutants can be produced by, for example, (i) eliminating a 75 to 1500 bp DNA fragment from an appropriate region of the g92 gene; (ii) producing smaller deletions of 5, 7, 8, 10 and 11 bp or about 50 to 200 bp near the 5' end of the coding sequences, such that the translational reading frame is altered and g92 polypeptide synthesis is aborted; (iii) deleting about 50 to 200 bp to eliminate the nucleotide sequences encoding the principal epitopes of g92; (iv) deleting about 10 to 200 bp of PRV DNA and at the same time inserting a foreign DNA sequence, such that hybride RNAs are produced which are not processed, transported, or translated properly on the polyribosomes; or (v) inserting a foreign DNA sequence, such that hybrid RNAs are produced which are not processed, transported, or translated properly on the polyribosomes.

In the present invention, the deletion mutant PRV(dlg92/dltk), described in detail below, was produced by eliminating a 1171 bp PRV SalI fragment which contains more than 80% of the coding sequences of the g92 gene. The size of this deletion insured that: (i) no polypeptide would be made with antigenic determinants, i.e., epitopes, capable of eliciting g92 antibodies in vaccinated animals, or capable of reacting with antisera to g92 glycoprotein produced in pigs infected with field strains of PRV; and (ii) reversion, i.e., back mutation to a g92-producing virus was virtually impossible. In the present invention, PRV g92 deletion mutants are preferred due to their low reversion frequency.

As discussed above, in another embodiment, the deletion and/or insertion mutants can contain a foreign DNA sequence in place of the deleted PRV g92 gene DNA or in addition to PRV g92 gene DNA sequences.

Figure 5:
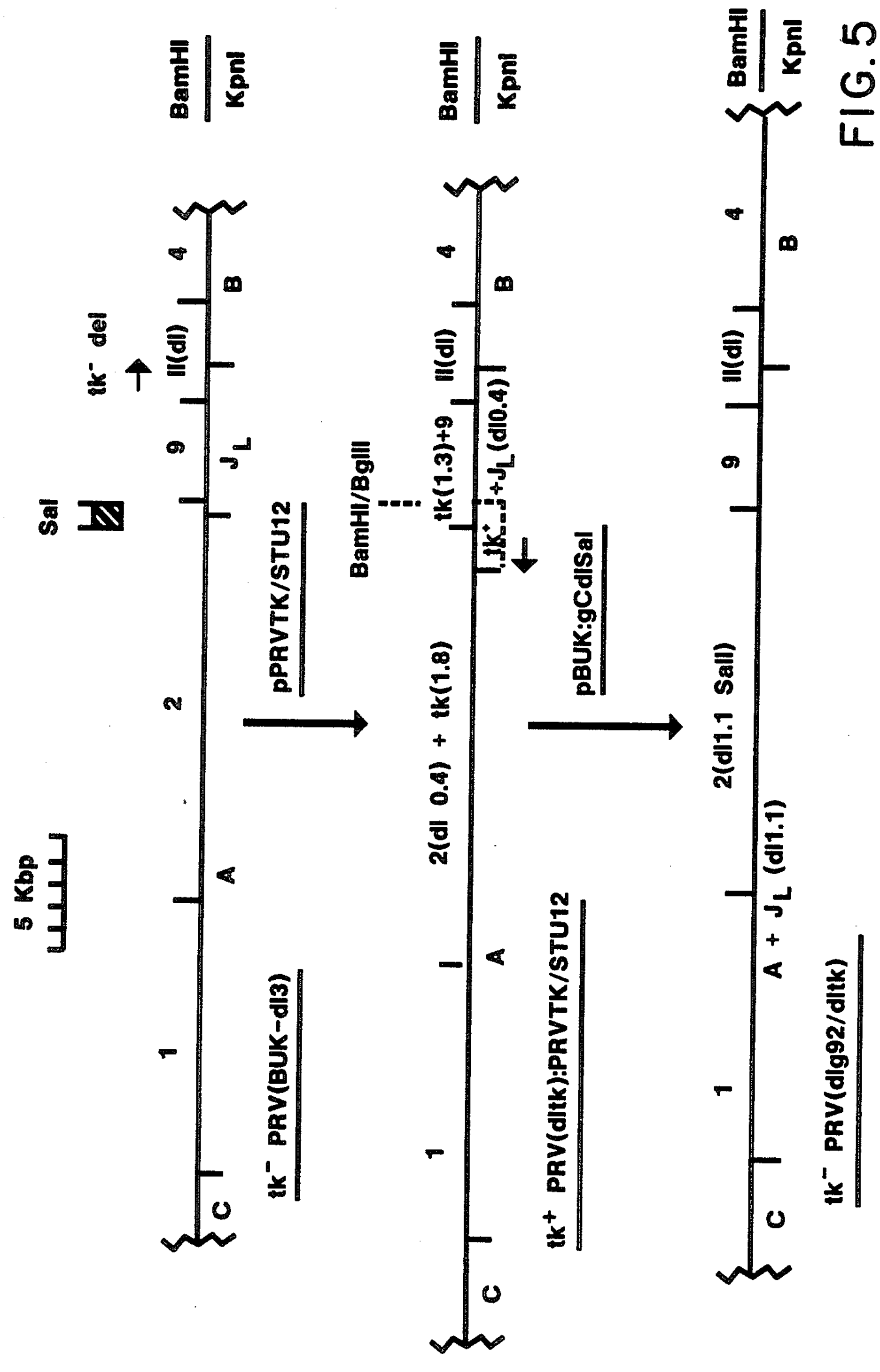
FIG. 5 shows the BamHI and KpnI restriction fragments in the regions of the PRV g92 and tk genes of infectious DNA of the $tk^-$ PRV(BUK-dl 3) and the $tk^+$ PRV(dltk):PRVTK/STU12, i.e., a virus isolated from recombinants of plasmid pPRVTK/STU12 and infectious DNA of the $tk^-$ PRV(BUK-dl 3). Also shown are the BamHI and KpnI restriction fragments of the $tk^-$ PRV(dlg92/dltk), which was formed by recombination between plasmid pBUK:gCdlSal and infectious DNA from the $tk^+$ PRV(dltk):PRVTK/STU12. The location of the 1.1 Kbp SalI fragment deleted from the PRV g92 gene is shown above the BamHI-2 fragment of PRV(BUK-dl 3). $tk^-$ del and 11(dl) indicate that an approximately 150 bp sequence was deleted from the BamHI-11 fragment of the $tk^+$ PRV(BUK-5) to form the $tk^-$ PRV(BUK-dl 3). To form the $tk^+$ PRV(dltk):PRVTK/STU12, a 3.1 Kbp KpnI to StuI/BglII fragment of pPRVTK/STU12 was inserted by recombination into the BamHI-2 fragment of the $tk^-$ PRV(BUK-dl 3) with the simultaneous deletion of the 0.4 Kbp KpnI to BamHI fragment of BamHI-2. This recombination generates new KpnI and BamHI restriction sites in the $tk^+$ PRV(dltk):PRVTK/STU12, as shown. The $tk^-$ PRV(dlg92/dltk) vaccine strain of the present invention has an approximately 150 bp deletion in the tk gene in the BamHI-11 fragment and a 1.1 Kbp SalI deletion in BamHI-2, which also eliminates a KpnI site and fuses the KpnI-A and KpnI-$J_L$ fragments.

As used herein, a "foreign DNA sequence" means (1) any DNA sequence which does not encode a gene, i.e., a non-coding DNA sequence, regardless of origin, such as a viral, eucaryotic, or procaryotic non-coding sequence and inclusive of oligonucleotide linkers; (2) any DNA sequence which encodes a gene other than a PRV gene, i.e., a coding DNA sequence, such as the selectable genes described above; or (3) any coding PRV DNA sequence which has been translocated from its normal location on the PRV genome to another location on the PRV genome, such as the PRV tk gene translocated into the PRV g92 gene found in PRV(dltk):PRVTK/STU12 (see: FIG. 5).

The oligonucleotide linker is generally 8-10 nucleotides in length, but can be longer, e.g., about 50 nucleotides, or shorter, e.g., 4, 5 or 7 nucleotides. The preferred length of the oligonucleotide linker is about 8 to 10 nucleotides in length. The DNA sequence of the oligonucleotide linker is not critical. Simarly, the size and sequences of other foreign DNA sequences employed in the present invention is not critical. Generally, the size of foreign DNA sequences, other than oligonucleotide linkers, is about 0.5 to 5 Kbp in length. For example, the HSV-1, HSV-2 and marmoset herpesvirus tk genes are about 1.3 Kbp in length; the chicken and human tk genes are about 2.9 and 4.2 Kbp in length, respectively; the neo® gene is about 1.0 Kbp in length; and the lacZ gene is about 3.0 Kbp in length.

The method of inserting the foreign DNA sequence into the plasmid DNA will depend upon the type of foreign DNA sequence used. Palindromic double stranded linkers containing one or more restriction nuclease sites in the oligonucleotide sequence (New England Biolabs) may be inserted by well known procedures (see: Maniatis, T., Fritsch, E. F. and Sambrook, J., *Molecular Cloning*, Cold Spring Harbor Laboratory (1982)). Foreign DNA sequences may also be inserted in plasmid DNA by tailing ends with complementary homopolymers using terminal transferase (see: Maniatis, T., Fritsch, E. F. and Sambrook, J., *Molecular Cloning*, Cold Spring Harbor Laboratory (1982)). By the judicious choice of foreign DNA sequence length, frame shift mutations may be produced in the g92 gene, augmenting the effect of deletions within the g92 gene.

Figure 3:
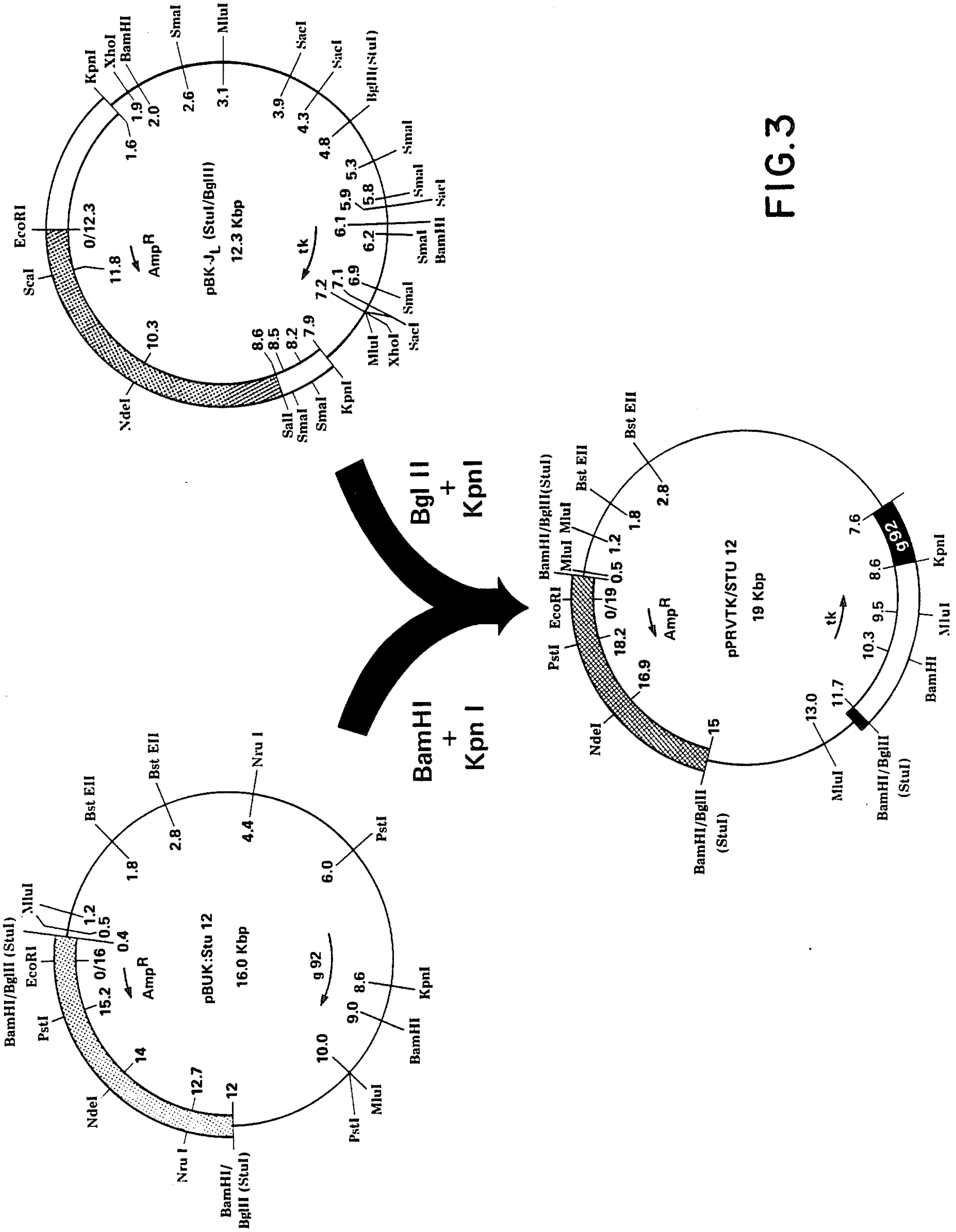
FIG. 3 schematically illustrates, by example, the derivation of plasmid pPRVTK/STU12. That is, the pBK-$J_L$(StuI/BglII) plasmid (see.

The particular cloning vector employed in the present invention to construct the hybrid plasmid comprising a DNA fragment of PRV containing substantially all of the PRV g92 gene and flanking sequences thereof of step (1) is not critical as long as the cloning vector contains a gene coding for a selective trait, e.g., drug resistance. Examples of such cloning vectors include pBR322 and pBR322-based vectors (see: Sekiguchi, T., Nishimoto, T., Kai, R. and Sekiguchi, M., *Gene* 21: 267–272 (1983)), pMB9, pBR325, pKH47 (Bethesda Research Laboratories), pBR328, pHC79 (Boehringer Manneheim Biochemicals), phage Charon 28 (Bethesda Research Laboratories), pKB11, pKSV-10 (P-L Biochemicals), pMAR420 (see: Otsuka, H., Hazen, M., Kit, M., Qavi, H. and Kit, S., *Virol.* 113: 196–213 (1981)) and oligo (dG)-tailed pBR322 (New England Nuclear). pBR322 is the preferred cloning vector in the present invention because the 31 Kbp PRV BglII-B fragment contains the PRV g92 gene and can be cloned in the single BamHI site of pBR322 (see: FIG. 3). Likewise, the 4 Kbp PstI fragment, which is shown in plasmid pBUK:Stu12 at 6.0 to 10.0 map units (see: FIG. 3), contains the PRV g92 gene and can be cloned at the single PstI site of pBR322.

The specific host employed for growing the hybrid plasmids of the present invention is not critical to the present invention. Examples of such hosts include *E. coli*, K12 RR1 (see: Bolivar, F., Rodriguez, R. L., Greene, P. J., Betlach, M. C., Heyneker, H. L., Boyer, H. W., Crosa, J. H. and Falkow, S., *Gene* 2: 95–113 (1977)); *E. coli* K12 HB101 (ATCC No. 33694); *E. coli* MM21 (ATCC No. 336780); and *E. coli DH*1 (ATCC No. 33849). *E. coli* K12 RR1 is the preferred host and has an F$-$ hsd R hsd M genotype.

Similarly, alternative vector/cloning systems can be employed such as plasmid vectors which grow in *E. coli* or *Saccharomyces cerevisiae*, or both, or plasmid vectors which grow in *B. subtillus*, or even vectors such as bovine papilloma virus (ATCC No. 37112) which grow in animal cells such as mouse (ATCC No. RL1616) (see: Elder, J. T., Spritz, R. A. and Weissman, S. M., *Ann. Rev. Gen.* 15: 295–340 (1981) and Ure, R., Grossman, L. and Moldave, K., *Methods in Enzymology* "Recombinant DNA", vol. 101, Part C, Academic Press, N.Y. (1983)).

As used herein, "flanking sequences" means the sequences upstream, downstream, or both upstream and downstream, from the g92 gene coding sequences. The upstream sequences contain the transcriptional control signals, i.e., promoters and enhancers, wherein the downstream sequences contain the transcription termination and polyadenylation signal of the g92 gene.

The precise PRV g92 gene sequences which must be present in the hybrid plasmids of steps (1) and (4) will depend on the sequences chosen for the deletion and the restriction nucleases to be employed in the engineering of the deletion mutant.

Figure 4:
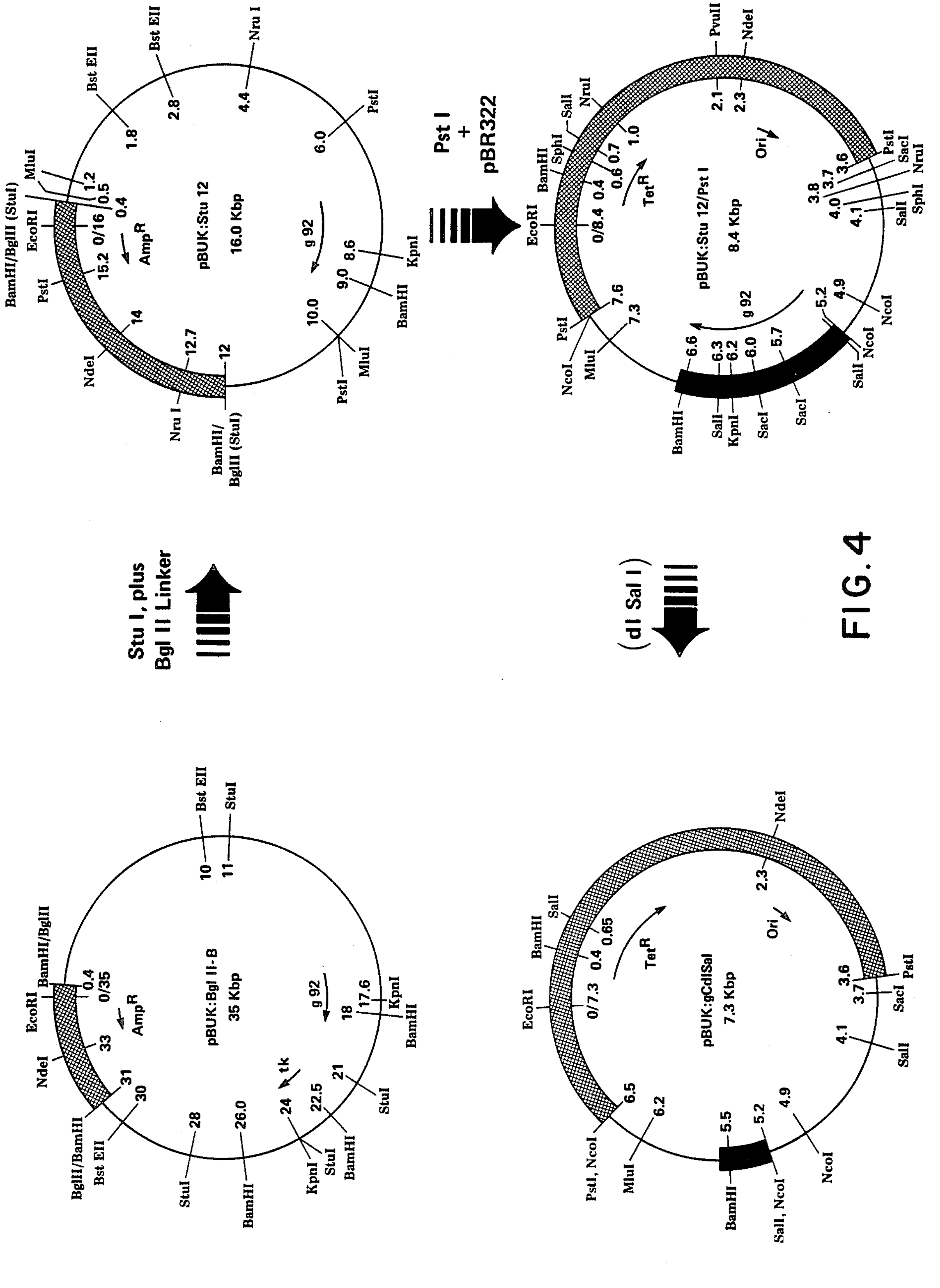
FIG. 4) to produce plasmid pPRVTK/Stul2. The pPRV TK/STU12 plasmid contains the PRV tk gene from pBK-$J_L$ inserted into the coding sequences of the PRV g92 gene. The derivation of pBUK-Stu12 is described in FIG. 4.

The specific PRV DNA sequences adjacent to the deletion in the plasmid required in steps (1) and (4) will depend on the specifics of the deletion in the hybrid plasmid. In general, the size of the PRV DNA sequences adjacent to both the 3′ and 5′ sides of the deletion and/or insertion will be at least about 400 bp. In plasmid pBUK:gCdlSal (see: FIG. 4), described in detail below, the 3′ and 5′ sequences on both sides of the deletion were 1.3 kb and 1.6 kb in length.

The specific PRV strain employed as a starting material in the present invention from which the PRV DNA fragment containing the g92 glycoprotein gene of step (1) is obtained is not critical. Examples of such strains include tk+ PRV strains, e.g., well-known attenuated strains such as the Bucharest strain, the SUCH-1 strain (see: Skoda, R. Brauner, I, Sadecky, E. and Mayer, V., *Acta Virol.* 8: 1–9 (1964)), and the Norden strain (see: Paul, P. S., Mengeling, W. L. and Pirtle, E. C., *Arch. Virol.* 73: 193–198 (1982)); and virulent strains isolated directly from diseased animals or passaged frequently in the laboratory such as the Aujeszky strain (ATCC No. VR-135), the P-2208 strain, the KC-152D strain (see: Maes, R. K., Kanitz, C. L. and Gustafson, D. P., *Am. J. Vet. Res.*, 44: 2083–2086 (1983)), the S62/26 Iowa strain, the Ind-F strain, the Ind-S strain, the Ind-R strain and the Shope strain (see: Paul, P. S., Mengeling, W. L. and Pirtle, E. C., *Arch. Virol.* 73: 193–198 (1982)); and tk− PRV strains such as PRV(BUK-5A) (ATCC No. VR-2028) and PRV(BUK-dl 3) (ATCC No. VR-2074), all of which produce g92.

As used herein, a "selectable gene" means a DNA sequence which encodes a gene product whose presence or absence can be easily detected. The selectable gene employed in step (2) is not critical to the present invention. Examples of such selectable genes can include a tk gene, the transposon Tn5 gene ($neo^R$) and the *E. coli* lacZ gene.

The specific tk gene employed as a selectable gene is not critical to the present invention. That is, the tk gene can be derived from any of the tk+ PRV strains discussed above or from other viruses which contain a viral specific tk gene such as HSV-1, the HSV-2, and marmoset herpesvirus (see: Kit, S., Kit, M., Qavi, H., Trkula, D. and Otsuka, H., *Biochem. Biophys. Acta* 741: 158–170 (1983); Otsuka, H. and Kit, S., *Virol.* 135: 316–330 (1984) and Wagner, M. J., Sharp, J. A. and Summers, W. C., *Proc. Natl. Acad. Sci.* U.S.A. 78: 1441–1445 (1981)). Alternatively, the tk gene can be of cellular origin such as the chicken and human tk genes (see: Merill, G. F., Harland, R. M., Graudine, M. and McKnight, S. L., *Mol. Cell. Biol.* 4: 1769–1776 (1984) and Bradshaw, H. D., Jr. and Deininger, P. L., *Mol. Cell. Biol.* 4: 2316–2320 (1984)). The tk gene of a Bucharest strain of PRV, such as PRV(BUK-5), is the preferred tk gene employed in the present invention as a selectable gene when the infectious tk− PRV DNA used in step (3) is derived from the Bucharest strain of PRV. The resulting recombinant viruses of step (3) should express with high efficiency, the tk+ gene in response to immediate-early PRV control signals. Heterologous viral and cellular tk+ genes may be expressed less efficiently in hybrid PRV recombinants. Alternatively, the hybrid plasmid of step (2) can contain the coding sequences of the heterologous viral or cellular tk+ gene linked to upstream transcriptional control sequences of the PRV tk+ gene.

The specific selection means for selecting for the presence or absence of a functional TK, i.e., tk+ or tk− viruses is not critical. Examples of the selection means for a tk+ virus include: growth medium supplemented with $10^{-4}$M hypoxanthine, $10^{-6}$M aminopterin, $4\times10^{-5}$M thymidine and $10^{-5}$M glycine (hereinafter "HATG") (see: Dubbs, D. R., Otsuka, H., Qavi, H. and Kit, S., *Virol.* 126: 408–411 (1983)) and growth medium supplemented with $6\times10^{-7}$M methotrexate; $1.6\times10^{-5}$M thymidine, $5\times10^{-5}$M adenosine, $5\times10^{-5}$M guanosine and $10^{-4}$M glycine (hereinafter "MTAGG") (see: Mungon, W., Kraiselburd, E., Davis, D. and Mann, J., *J. Virol.* 7: 813–820 (1971)). Examples of the selection means for a tk− virus include: growth medium containing 25 μg/ml 5-bromodeoxyuridine (hereinafter "BrdUrd"), growth medium containing 100 μg/ml 5-iododeoxyuridine (hereinafter "IdUrd") or growth medium containing 100 μg/ml arabinosylthymine. Many modifications of the nucleoside analog selection techniques for tk− viruses can also be used. For example, the virus infected cells can be grown in media with about 2.5 to 25 μg/ml BrdUrd. Since the BrdUrd is incorporated into DNA of tk+ viruses and BrdUrd-containing DNA is highly photosensitive the virus harvests can be treated with about 0.5 μM Hoechst 33258 to further photosensitize the DNA. The DNA is then exposed to "cool white" fluorescent light (General Electric, 15 w) for 4 min to deliver about 50 ergs/$mm^2$/sec (Hillary, A. M., Lugo, T. G. and Fournier, R. E. K., *Biochem. Genet.* 22: 201–213 (1984)). Following this procedure, the infectivity of tk+ viruses is selectively destroyed, while tk− viruses are resistant to this treatment.

As discussed above, selectable genes other than the tk gene can be used in step (2) such that the resulting hybrid plasmid of step (2) contains a functional selectable gene flanked by DNA sequences of the PRV g92 gene. For example, the transposon Tn5 gene ($neo^R$) which encodes an aminoglycoside 3′-phosphotransferase capable of conferring resistance to neomycin and to the drug, G418 (see: pNeo; Pharmacia P-L Biochemicals). To obtain expression of the transposon Tn5 gene, it is necessary that a PRV promoter be positioned 5′ to the coding region of the transposon Tn5 gene. The chimeric plasmid produced in this way can then be used with G418 in step (3) to select for recombinant PRV g92 mutants which fail to express the g92 glycoprotein (see: Franke, C. A., Rice, C. M., Strauss, J. H. and Hruby, D. E., *Mol. Cell. Biol.* 5: 1918–1924 (1985)).

Alternatively, as discussed above, the *E. coli* lacZ gene can be used instead of the tk gene in step (2) such that the *E. coli* lacZ gene is fused to a PRV promoter and the resulting chimeric gene is flanked on both the 5′ and 3′ sides by PRV g92 nucleotide sequences. This hybrid plasmid can then be used in step (3) to select for recombinant PRV plaques expressing β-galactosidase, which is detected by the blue color produced with O-nitrophenyl-β-D-galactopyranoside and XGal (Boehringer-Mannheim) (see: Chakrabarti, S., Brechling, K. and Moss, B., *Mol. Cell. Biol.* 5: 3403–3409 (1985)).

The specific PRV strain which fails to produce the product of the selectable gene is not critical and will depend upon the selectable gene employed. That is, PRV encodes a viral specific tk gene. Thus, when the selectable gene is a tk gene, the PRV strain employed must be a tk− PRV strain. The tk− PRV strains can be spontaneous mutants, mutagen-induced mutants, or deletion and/or insertion mutants, so long as they do not revert with a detectable frequency to tk+ in, for example, growth medium supplemented with HATG. Examples of spontaneous mutants include the araT-resistant strains such as tk− PRV(Ka), tk− PRV(Bartha) and tk− PRV(Norden) (see Lomniczi, B., Watanabe, S., Ben-Porat, T. and Kaplan, A. S., *J. Virol.* 52: 198–205 (1984)). Examples of mutagen-induced mutants include the mutants described in U.S. Pat. No. 4,514,497, including the tk− PRK(BUK-5A) (ATCC No. VR-2028). Examples of deletion mutants include the mutants described in U.S. Pat. No. 4,514,497, including PRV(BUK-dl 3) (ATCC No. VR-2074). PRV(BUK-dl 3) is the preferred deletion mutant since it was derived from a mutagen-induced tk− PRV, i.e., PRV(BUK-5A) (ATCC No. VR-2078) which is a highly attenuated temperature-resistant PRV which also does not produce PRV gI. Since PRV does not encode for a viral specific transposon Tn5 gene or *E. coli* lacZ gene, when employing these selectable genes, any of the PRV strains discussed above, including the tk− PRV strains can be employed.

The particular PRV host cells employed in the present invention will depend on the selectable gene employed. That is, to select for a tk+ gene, tk− host cells should be employed. However, to select for a functional $neo^R$ gene or lacZ gene, either tk+ or tk− host cells can be employed since neither naturally produce the $neo^R$ or lacZ gene products.

The specific tk+ host cells employed in the present invention are not critical as long as they allow for permissive growth of PRV. Examples of such tk+ host cells include RAB-9 (rabbit skin cells) having ATCC No. 1414; primary rabbit kidney cells; secondary rabbit kidney cells; monkey cells; e.g., CV-1 and OMK; human cells, e.g., HeLa(S3) and human embryonic kidney cells; and chick embryo fibroblast cells. RAB-9 are the preferred tk+ host cells employed in the present invention. However, it should be noted that for the production of virus to be used for vaccination of animals in the field, a United States Department of Agriculture certified cell line permissive for PRV, preferably of the same species as the animal to be vaccinated, and free of other infectious agents, should be used. For example, a suitable porcine cell line would be a certified diploid non-tumorgenic swine testicle (ST) cell line free of mycoplasma and other viruses.

The specific tk− host cells employed in the present invention are not critical as long as they allow for permissive growth of PRV. Examples of such tk− host cells include rabbit Rab(BU), mouse LM(TK−), human HeLa(BU25) (see: Kit, S., Dubbs, D. R. and Frearson, P. M., *Int. J. Cancer* 1: 19–30 (1966); Kit, S., Dubbs, D. R., Prekarski, L. J. and Hsu, T. C., *Exp. Cell Res.*, 31: 297–312 (1963); Kit, S. and Qavi, H., *Virol.* 130: 381–389 (1983); Kit, S., Qavi, H., Dubbs, D. R. and Otsuka, H., *J. Med. Virol.* 12: 25–36 (1983)), syrian hamster BHK 21(TK−) (see: Sandus, P. G., Wilkie, N. M. and Davidson, A. J., *J. Gen. Virol.* 63:277–295 (1982)), and human line 143 (see: Campione-Picardo, Rawls, W. E. and Bacchetti, S., *J. Virol.* 31: 281–287 (1979)). Rab(BU) are the preferred tk− host cells employed in the present invention.

In the context of this invention, a temperature-resistant virus is a virus which is non-temperature sensitive. Thus, a temperature-resistant virus is capable of replicating, at a non-permissive temperature, i.e., about 38.5° C. to 40° C. preferably 39.1° C., about as well as the parental virus or field isolates of PRV replicate at a permissive temperature. By contrast, temperature-sensitive PRV strains contain mutations in viral genes essential for replication, whereby functional gene products are produced at permissive temperatures, i.e., about 32° C. to 37.5° C., preferably 34.5° C., but not at non-permissive temperatures. Therefore, in temperature-sensitive viruses, production of infectious virus particles is 4 to 7 logs lower at the non-permissive temperatures compared to production at permissive temperatures. With temperature-resistant virus strains, production of infectious virus particles is about the same at non-permissive temperatures as at permissive temperatures.

Temperature-resistant viruses are superior to temperature-sensitive viruses as modified live virus vaccines because (1) attenuation results from alterations in pathogenic viral genes rather than from crippling viral genes required for replication; and (2) temperature-resistant viruses can be safely administered intramuscularly, intranasally or intravenously and can replicate in the deep tissues of the body so as to elicit a more complete and prolonged immunological response.

In contrast, temperature-sensitive viruses only replicate at low temperature sites, such as the upper respiratory tract, and thus, can only be administered intranasally.

The g92− PRV mutants of the present invention can be employed as modified live virus vaccines against pseudorabies diseases when containing additional mutations which attenuate PRV. Such additional mutations include tk− mutations and gI− mutations.

Alternatively, the g92− PRV mutants of the present invention can be employed as killed virus vaccines against pseudorabies disease. That is, inactivation of infectivity by ultraviolet light or formalehyde treatment of the g92− PRV mutants yields a vaccine capable, after intraperitoneal administration, of eliciting cytotoxic T cells and protective antibodies against glycoproteins gIIa, gIIb, gIIc, gIV and gV. Animals immunized with this vaccine would thus be protected against virulent virus infections.

Furthermore, non-ionic detergent extracts (Nonidet P40 or Triton X-100) can be made from PRV g92−-infected pig cells to produce subunit PRV vaccines. These extracts contain all of the glycoproteins and non-glycoproteins encoded by the PRV strain employed with the exception of glycoprotein g92. After purification of the glycoproteins, they can be employed as subunit vaccines (see: Hilleman, M. R., Larson, V. M., Lehman, E. D., Salerno, R. A., Conrad, P. G., McLean, A. A., In: *The Human Herpesvirus: An Interdiciplinary Perspective,* Eds. Nahmias, A. J., Dowdle, W. R. and Schinazi, R. F., (Elsevier, N.Y.), page 503 (1981); Eisenberg, R. J., Ponce de Leon, M., Perevia, L., Long, D. and Cohen, G. H., *J. Virol.* 41: 1099–1104 (1982); Long, D., Madara, T. J., Ponce de Leon, M., Cohen, G. H., Montgomery, P. C., Eisenberg, R. J., *Inf. Immun.* 37: 761–764 (1984); and Dix, R. D. and Mills, J., *J. Med. Virol.* 17: 9–18 (1985)).

As another alternative, the g92− PRV mutants of the present invention can be employed as the tk+ PRV strain used as a starting material to obtain the tk− PRV mutants described in U.S. Pat. No. 4,514,497.

A pharmaceutically effective amount of the above-described viruses of the present invention can be employed along with a pharmaceutically acceptable carrier or diluent as a vaccine against pseudorabies disease in animals, such as swine, cattle, sheep and goats.

Examples of pharmaceutically acceptable carriers or diluents useful in the present invention include any physiological buffered medium, i.e., about pH 7.0 to 7.4, containing from about 2.5 to 15% serum which does not contain antibodies to PRV, i.e., is seronegative for PRV. Agammaglobulin serum is preferred to serum which contains gammaglobulin. Examples of serum to be employed in the present invention include: swine serum, calf serum, fetal calf serum, horse serum and lamb serum. Agammaglobulin swine serum from pigs seronegative for PRV would be preferred for vaccination of swine and fetal calf serum or agammaglobulin calf serum would be preferred for vaccination of calves. Serum protein such as porcine albumin or bovine serum albumin in an amount of from about 0.5 to 3.0% can be employed as a substitute for serum. However, it is desirable to avoid the use of foreign proteins in the carrier or diluent which will induce allergic responses in the animal being vaccinated. Prior to lypholization, the virus may be diluted using any of the conventional stabilizing solutions containing phosphate buffered saline, glutamate, casitone or lactose hydrolyzate, sucrose, sorbose, lactose, gelatin and preservatives such as gentamicin, fungazone and amphotericin B.

It is preferred that the viruses of the present invention be stored at a titer of at least $10^{5.5}$ to $10^{6.5}$ p.f.u./ml in a lypholized state at 4° C. to −20° C. The lypholized virus may be reconstituted for use with sterile distilled water containing 1.0% (v/v) glycerol.

The useful dosage to be administered will vary depending upon the age, weight and species of the animal vaccinated and the mode of administration. As a live modified virus vaccine, a suitable dosage can be, for example, about $10^{4.5}$ to $10^{6.5}$ p.f.u., preferably about $10^{5.0}$ to $10^{6.0}$ p.f.u. As a killed vaccine, a suitable dosage can be, for example, about 10 fold greater than that employed for a modified live virus vaccine.

The vaccines of the present invention can be administered intramuscularly and subcutaneously. Intramuscularly is the preferred mode of administration. The modified-live vaccines of the present invention can also be administered intranasally.

The following examples are provided for illustrative purposes and are in no way intended to limit the scope of the present invention.

In the following examples, all media and buffer solutions were made up in glass distilled water unless otherwise indicated.

EXAMPLE 1

Production Of g92− Mutants Of PRV

A. Purification of PRV DNA

PRV DNA was prepared essentially as described by Pignatti et al for the preparation of HSV DNA (see: Pignatti, P. F., Cassai, E., Meneguzzi, G., Chemciner, N., and Milanesi, G., *Virol.* 93: 260-264 (1979)).

More specifically, 20 8-oz prescription glass bottle monolayer cultures of RAB-9 (about $5\times10^6$ cells/culture) containing 20 ml of Eagle's minimal essential medium (AutoPow, APMEM, Flow Laboratories, Inc.) plus 10% (v/v) fetal calf serum, 50 μg/ml neomycin and 2.0 mM glutamine and 10 mM HEPES, pH 7.3 (hereinafter "growth medium") were infected at an m.o.i. of 5.0 PFU/cell with PRV(BUK-7). PRV(BUK-7) is a plaque purified clone of the well known and readily available Bucharest strain of PRV strain (see: U.S. Pat. No. 4,514,497). The infected cells were then incubated for 3 hr at 34.5° C., at which time cellular DNA synthesis had been inhibited by the viral infection. Then 1.0 μCi/ml and 0.25 μg/ml of $^3$H-thymidine was added to radioactively label the viral DNA and incubation was continued at 34.5° C. for 17 hr more. The cells were dislodged from the glass by scraping into the growth medium with a rubber policeman, centrifuged at 600Xg, washed with ice cold phosphate-buffered saline solution comprising 0.14M NaCl, 0.003M KCl, 0.001M $CaCl_2$, 0.0005M $MgCl_2$, and 0.01M phosphate, pH 7.5 (hereinafter "PBS"), containing 10 μg/ml nonradioactive thymidine. Next, the cells were centrifuged at 600Xg and then frozen in an ethanol-dry ice bath.

After thawing, the cell pellet (about 0.7 ml) was resuspended in 9 volumes of lysing solution comprising 0.25% (w/v) Triton X-100, 10 mM EDTA, 10 mM Tris-HCl, pH 7.9. Next, the cell suspension was transferred to a Dounce homogenizer and incubated at room temperature for 20-30 min with gentle mixing.

Then, the cell suspension was transferred to a glass centrifuge tube and NaCl was added to a final concentration of 0.2M. Next, the tube was inverted several times and the solution was immediately centrifuged at 1000×g at 4° C. for 10 min.

The resulting supernatant was decanted into a glass tube and deproteinized by incubating with 100 μg/ml proteinase K (E. M. Science) in buffer solution comprising 10 mM Tris-HCl, pH 7.5, 1.0 mM EDTA (hereinafter "TE buffer") for 1 hr at 37° C. Then, 1 volume of 90% (v/v) redistilled phenol was added, the solution was mixed by inversion, centrifuged at 20,000×g, and the aqueous phase, i.e., top phase, was transferred to a polyallomer centrifuge tube. Solid sodium acetate was then added to a concentration of 4.0% (w/v), the nucleic acids were precipitated with 2 volumes of ice cold ethanol, and incubated overnight at −20° C. Thereafter, the precipitate was collected by centrifugation at 16,000 rpm at 4° C. in a Spinco SW25 rotor, dissolved in 2.0 ml TE buffer, dialyzed at 4° C. against TE buffer.

The resulting DNA solution was then transferred to a polyallomer centrifuge tube and CsCl in TE buffer was added to 57% (w/w) ($\rho$=1.715 g/cm$^2$). Next, the DNA was centrifuged for 46 hr at 22.5° C. at 44,000 rpm in a Spinco No. 50 Ti rotor. Then, 12 drop fractions were collected from the bottom of the polyallomer tube and aliquots of 4.0 μl were counted in a liquid scintillation spectrometer to locate the PRV DNA containing fractions ($\rho$=about 1.727 g/cm$^2$). When a total of 25 fractions were collected, generally fractions 13-15 contained the PRV DNA.

The PRV DNA containing fractions were then pooled and dialyzed against several changes of TE buffer at 4° C. for about 24 hr. The concentrations of DNA was determined fluorometrically. The PRV(BUK-7) DNA yield was about 50 μg from $10^8$ cells.

The identity of the PRV(BUK-7) DNA was verified by the pattern of restriction nuclease-digested PRV(BUK-7) DNA fragments obtained after electrophoresis at 4° C. in a submarine gel apparatus (Bethesda Research Laboratories, Inc.) as described below.

The resulting PRV(BUK-7) DNA was cleaved with BamHI, BglII, and KpnI restriction nucleases under the reaction conditions recommended by the manufacturer (New England BioLabs, Inc.). Next, 1/10 volume of a solution comprising 0.4% (w/v) bromophenol blue, 125 mM EDTA, and 50% (v/v) glycerol was added to terminate the reaction, followed by heating at 65° C. for 10 min. Twenty μl aliquots of each sample was applied into the sample wells of the agarose gel, and electrophoresis was carried out as described below.

Figure 2:
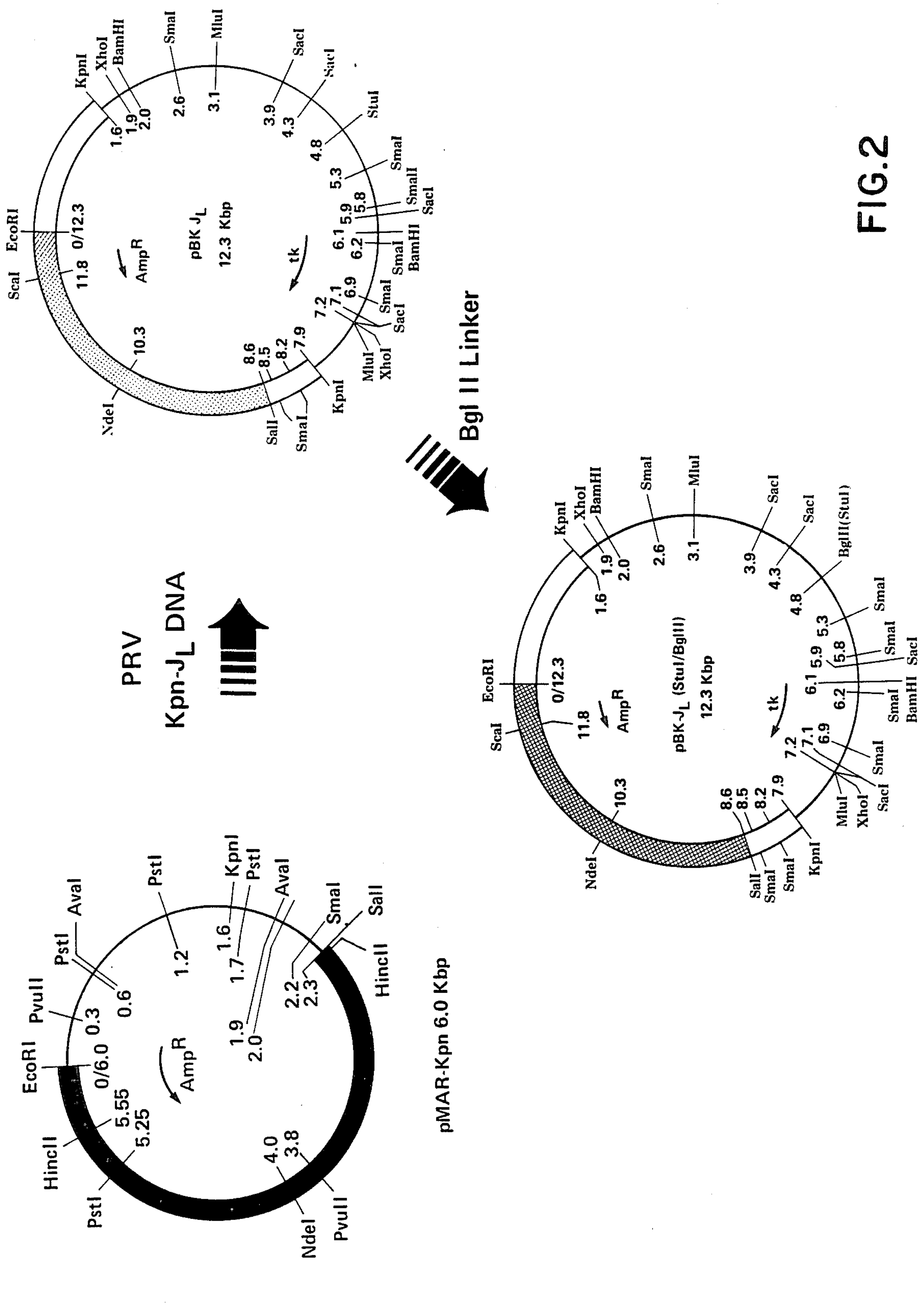
FIG. 2 schematically illustrates, by example, the derivation of plasmids pBK-$J_L$ and pBK-$J_L$(StuI/BglII) employed in the present invention. That is, the PRV(BUK-7) KpnI-$J_L$ fragment (see.

Electrophoresis of restriction nuclease fragments was carried out on 0.6% (w/v) agarose slab gels (see: Kit, S., Qavi, H., Dubbs, D. R., and Otsuka, H., *J. Med. Virol.* 12: 25–36 (1983)) in electrophoresis buffer comprising 30 mM $NaH_2PO_4$, 1.0 mM EDTA, 40 mM Tris-HCl, pH 8.1 (hereinafter "electrophoresis buffer") at 45 volts, 4° C. for about 16 hr. After electrophoresis, DNA fragments were stained by soaking the gel in electrophoresis buffer containing 0.5 μg/ml ethidium bromide, visualized over a long-wave UV illuminator, and photographed. The restriction nuclease patterns were similar to those previously described for PRV DNA (see: Kit, S., Kit, M., and Pirtle, E. C., *Am. J. Vet. Res.* 46: 1359–1367 (1985); Lomniczi, B., Blankenship, M. L., and Ben-Porat, T., *J. Virol.* 49: 970–979 (1984)). Restriction nuclease maps illustrating the location of BglII, BamHI and KpnI fragments of the PRV(BUK-5) and PRV(BUK-7) genome are shown in FIG. 2 of U.S. Pat. No. 4,514,497. These fragments map at essentially the same locations as do the corresponding DNA fragments of PRV(Kaplan) shown in FIG. 1. PRV(BUK-5) or PRV(BUK-7) could be employed interchangeably in the present invention. The sizes of the BglII, BamHI and KpnI fragments are shown in Table 1 below.

PRV(BUK-7) DNA prepared in this manner had an infectivity of about 100 PFU/μg DNA in the standard transfection assay (see: Graham, F. L. and Van der Eb, A. J., *Virol.* 52: 456–467 (1973)).

TABLE 1

SIZE OF BamHI, KpnI AND BglII Restriction Fragments OF PRV(BUK-5) AND PRV(BUK-7)

| BamHI fragment | Kbp | KpnI fragment | Kbp | BglII fragment | Kbp |
|---|---|---|---|---|---|
| 1 | 30.3 | A | 29.0 | A | 50.8 |
| 2 | 17.8 | B | 21.4 | B | 31.6 |
| 3 | 16.7 | C | 14.5 | C | 28.5 |
| 4 | 9.8 | D | 13.0 | D/E | 19.7 |
| 5 | 8.2 | E | 10.4 | F | 12.3 |
| 5 | 8.2 | F | 9.4 | — | — |
| 5 | 7.5 | G | 8.6 | — | — |
| 6 | 7.5 | H | 8.6 | — | — |
| 7 | 6.7 | I | 4.4 | — | — |
| 8 | 5.1 | $J_L$ | 6.3 | — | — |
| 8 | 5.1 | $J_S$ | 5.9 | — | — |
| 8 | 5.5 | K | 5.9 | — | — |
| 9 | 4.3 | K | 5.9 | — | — |
| 10 | 3.8 | L | 1.7 | — | — |
| 11 | 3.5 | M | 0.7 | — | — |
| 13 | 1.7 | M | 0.7 | — | — |
| 14 | 1.4 | N | 0.5 | — | — |
| 14 | 1.4 | — | — | — | — |
| 15 | 1.0 | — | — | — | — |
| 16 | 0.8 | — | — | — | — |
| TOTAL: | 146.3 | TOTAL: | 146.9 | TOTAL: | 142.9 |
| Fragments generated by inversion of L segment: BamHI-Z = 3.2 Kbp | | Fragments generated by inversion of L segment: KpnI-X = 1.9 | | Fragment E produced by inversion of S segment | |

TABLE 1-continued

SIZE OF BamHI, KpnI AND BglII Restriction Fragments OF PRV(BUK-5) AND PRV(BUK-7)

| BamHI fragment | Kbp | KpnI fragment | Kbp | BglII fragment | Kbp |
|---|---|---|---|---|---|
| BamHI-10B" = 3.8 Kbp | | KpnI-D + H = 21.6 | | | |

B. Construction of Plasmid pBK-$J_L$

KpnI fragments of DNA isolated from PRV(BUK-7) were cloned at the KpnI cleavage site of pMAR-Kpn by the following procedure (see: FIG. 2):

pMAR-Kpn is a 6.0 Kbp plasmid derived from pMAR420 with a single KpnI cloning site (see: Otsuka, H., Hazen, M., Kit, M., Qavi, H. and Kit, S., *Virol.* 113: 196–213 (1981)) pMAR-Kpn was obtained by deleting the 4.3 Kbp XhoI to SalI fragment from pMAR-420. In this step, cloning vectors other that pMAR-Kpn could be employed without departing from the spirit and scope of this invention. For example, pKB111, pKSV-10 (Pharmacia P-L Biochemicals) and pMAR420 could be employed since they have only one KpnI cloning site. Similarly, oligo(dG)-tailed pBR322 could be employed as the cloning vector with an oligo(dC)-tailed KpnI fragment of PRV.

4.0 μg DNA from PRV(BUK-7) was dissolved in 100 μl of a buffer (hereinafter "KpnI cutting buffer") comprising 6.0 mM NaCl, 6.0 mM Tris-HCl (pH 7.5), 6.0 mM $MgCl_2$, 1.0 mM dithiothreitol, and 100 μg/ml bovine serum albumin (hereinafter "BSA"). The DNA was then digested for 1 hr with 40 units of KpnI (New England BioLabs, Inc.). The reaction was terminated by adding cyclohexanediamine tetraacetate (hereinafter "CDTA") to 20 mM and heating at 65° C. for 30 min. After adding sodium acetate to 0.1M, the DNA was precipitated with 2 volumes of ethanol, stored at −20° C. overnight, and collected by centrifugation.

The cloning vector, pMAR-Kpn, was linearized by incubating 0.5 μg of pMAR-Kpn DNA in 50 μl of KpnI cutting buffer, then digesting with 5 units of KpnI at 37° C. for 1 hr. The reaction was terminated as described above, and the DNA collected by centrifugation after ethanol precipitation.

4.0 μg of KpnI-cleaved PRV(BUK-7) and 0.1 μg of KpnI-cleaved pMAR-Kpn were dissolved in 50 μl of a buffer comprising 50 mM Tris-HCl (pH 7.8), 10 mM $MgCl_2$, 20 mM dithiothreitol, 1.0 mM ATP, 50 μg/ml BSA (hereinafter "ligation buffer"), and containing 1000 units T4 DNA ligase (New England BioLabs, Inc.), and incubated overnight at 4° C. The reaction was terminated by adding EDTA to 20 mM and heating at 65° C. for 30 min.

The recombinant plasmid DNA was diluted in TE buffer and used to transform *E. coli* K12 RR1 bacteria as described below (see: Bolivar, F., Rodriguez, R. L., Greene, P. J., Betlach, M. C., Heyneker, H. L., Boyer, H. W., Crosa, J. H., and Falkow, S., *Gene* 2: 95–113 (1977)).

Bacteria were prepared for transformation using $CaCl_2$ (see: Mandel, M. and Higa, A., *J. Mol. Biol.* 53: 159–162 (1970)). Specifically, an overnight culture at a density of 2.0 ($A_{600}$) of *E. coli* K12 RR1 was used to inoculate 200 ml of broth comprising 1.0% (w/v) bactotryptone, 0.5% (w/v) yeast extract, and 0.5% (w/v) NaCl (hereinafter "ML broth"), at a bacterial density of 0.02 ($A_{600}$). The bacteria were incubated for about 2 hr until a density of about 0.5 ($A_{600}$) was achieved. The bacteria were then pelleted by centrifugation and resuspended in ¼ volume of cold 50 mM $CaCl_2$. After a 5-min incubation on ice, the bacteria were again pelleted and resuspended in 1/40 the volume of ice cold 50 mM $CaCl_2$.

Next, 1/10 ml of the recombinant plasmid DNA, about 10–100 ng, in TE buffer was added to 0.2 ml of the $CaCl_2$-treated bacteria. The mixture was kept at 4° C. for 30 min. Then, the temperature was raised to 37° C. for 5 min and 0.3 ml of ML broth was added. Thereafter, incubation was continued for 45 min at 37° C. with gentle shaking. Samples were plated on trypticase soy agar plates (BBL Microbiology Systems) supplemented with 30 μg/ml ampicillin.

Rapid screening of the resulting clones for the desired recombinant plasmid DNA was conducted as follows:

An overnight culture of bacteria containing recombinant plasmid DNA was inoculated into 5.0 ml of ML broth containing 30 μg/ml ampicillin and incubated at 37° C. to a density of about 1.5 ($A_{600}$). One ml of this bacterial culture was then transferred to a 1.5 ml Eppendorf polypropylene tube and centrifuged in an Eppendorf centrifuge for about 1 min at room temperature to pellet the bacteria. Next, the bacteria was resuspended in 0.1 ml of lysozyme solution No. 1 comprising 2.0 mg/ml egg lysozyme, 50 mM glucose, 10 mM CDTA, and 25 mM Tris-HCl buffer, pH 8.0 (hereinafter "lysozyme solution No. 1"), and then incubated for 30 min at 4° C. Next, 0.2 ml of 0.2N NaOH plus 1.0% (w/v) sodium dodecylsulfate was added to the bacterial suspension and the tube was vortexed and kept at 4° C. for 5 min. Thereafter, 0.15 ml of 3.0M sodium acetate, pH 4.8, was added, and the tube was gently inverted, during which time a "clot" of DNA formed. The DNA was kept at 4° C. for 1 hr to allow chromosomal DNA, protein, and high molecular weight RNA to precipitate. Next, the precipitate was centrifuged in an Eppendorf centrifuge for 5 min at room temperature and the clear supernatant fluid, approximately 0.4 ml, containing recombinant plasmid DNA was transferred to a second Eppendorf centrifuge tube. Then, 2½ volumes of ethanol (approximately 1.0 ml) were added to the second tube which was placed at −20° C. for 30 min. The precipitated recombinant plasmid DNA was collected by centrifugation for 2 min at room temperature in an Eppendorf centrifuge. Then, the recombinant plasmid DNA was dissolved in 0.1 ml of 0.1M sodium acetate, 0.05M Tris-HCl, pH 8.0, reprecipitated with ethanol, collected by again centrifuging, and finally dissolved in 50 μl of water.

Then, a 10 μl aliquot of plasmid DNA was diluted in KpnI cutting buffer and 2.0 units of KpnI were added. Following a digestion period of 60 min at 37° C., the sample was mixed with 1/10 volume of a solution comprising 0.4% (w/v) bromophenol blue, 125 mM EDTA, and 50% (v/v) glycerol, and about 20 μl was applied to a 0.6% (w/v) agarose slab gel for electrophoretic analysis as described above. This analysis revealed whether the recombinant plasmid contained a KpnI insert and, if so, the size, in Kbp, of the insert (see: Birnboim, H. C. and Doly, J., *Nucl. Acids Res.* 7: 1513–1523 (1973)).

For large-scale preparation of recombinant plasmid DNA, 200 times the amount of plasmid-transformed bacteria were processed as compared with the bacteria used to produce recombinant plasmid DNA for the rapid screening procedure described above, except that after the first ethanol precipitation, the sample was treated, at 37° C. for 30 min, with 0.5 mg of pancreatic RNase A (Worthington Biochemicals) from a stock solution comprising 1.0 mg/ml RNase A in 5.0 mM Tris-HCl pH 8.0 which had been heated at 100° C. for 10 min. The treatment was followed by the addition of 500 μg of proteinase K (E. M. Science) in TE buffer at 37° C. for 30 min. Subsequently, an equal volume of phenol was added, the sample was vortexed and centrifuged as described above to separate the phases. The aqueous phase was then removed, precipitated with ethanol, and collected by centrifugation as described above. The precipitate was then dissolved in 0.2 ml of TE buffer and layered on a 10.4 ml linear 10–40% (w/v) sucrose gradient in 50 mM NaCl, 10 mM Tris-HCl, pH 7.5, 1.0 mM EDTA, and was then centrifuged at 4° C. for 20 hr at 24,000 rpm in a Spinco SW41 rotor. Fifteen drop fractions were collected from the bottom of polyallomer centrifuge tubes into wells of plastic trays. A total of 35 fractions was obtained. Five μl aliquots were then screened by employing agarose gel electrophoresis as described above. Fractions containing recombinant plasmid DNA were pooled, dialyzed against 0.1X TE buffer, and stored at 4° C. for further studies. Using these procedures, a 12.3 Kbp recombinant plasmid containing the 6.3 Kbp KpnI-$J_L$, fragment cloned into the KpnI site of pMAR-Kpn was obtained. The KpnI-$J_L$ fragment contains the PRV tk gene (see: U.S. Pat. No. 4,514,497). The resulting plasmid was designated pBK-$J_L$ (see: FIG. 2).

C. Construction of pBK-$J_L$(StuI/BglII)

In order to mobilize efficiently and selectively the DNA fragment from pBK-$J_L$ that contained the tk gene, the StuI site of plasmid pBK-$J_L$ was converted to a BglII site as follows (see: FIG. 2):

1.0 μg of pBK-$J_L$ was dissolved in 100 μl of a buffer comprising 100 mM NaCl, 10 mM Tris-HCl (pH 8.0), 10 mM $MgCl_2$, 6.0 mM 2-mercaptoethanol, 100 μg/ml BSA (hereinafter "StuI cutting buffer"), and digested with 5 units of StuI (New England BioLabs, Inc.) for 2 hr at 37° C. The reaction was terminated by the addition of CDTA to 20 mM and heating to 65° C. for 30 min. Then, sodium acetate was added to 0.1M, and the DNA was precipitated with ethanol and collected by centrifugation. The StuI-cleaved pBK-$J_L$ was dissolved in ligation buffer containing 1.0 μg of phosphorylated BglII linker (New England BioLabs, Inc.) and 1000 units of T4 DNA ligase. After overnight incubation at 4° C., the reaction was terminated by adding EDTA to 20 mM and heating at 65° C. for 10 min. The StuI-cleaved pBK-$J_L$ plasmids now possessing concatenated BglII linkers were separated from the unreacted linkers by centrifugation of the DNA on a 10–40% (w/v) sucrose gradient in 50 mM NaCl, 10 mM Tris-HCl (pH 7.5) 1.0 mM EDTA at 40,000 rpm for 8 hr in a Spinco SW41 rotor. Fractions were then collected and the DNA was localized by analysis of aliquots on agarose gel electrophoresis as described above. Then, the plasmid DNA was brought to 0.1M sodium acetate, 2.0 μg of carrier yeast tRNA added, and the DNA was precipitated with ethanol and collected by centrifugation. In order to create BglII cohesive ends on the plasmid, the StuI-cleaved pBK-$J_L$ with concatenated BglII linkers at the termini was dissolved in 50 μl of a buffer comprising 100 mM NaCl, 10 mM Tris-HCl (pH 7.4), 10 mM $MgCl_2$, 10 mM 2-mercaptoethanol, 100 μg/ml BSA (hereinafter "BglII cutting buffer"), and digested with 8 units of BglII (New England Biolabs, Inc.) for 1 hr at 37° C. The DNA was ethanol precipitated and collected by centrifugation, then dissolved in 50 μl of ligation buffer, and religated to circularize the plasmid as described above. After transformation of *E. coli* K12 RR1 with the resulting plasmids as described above, colonies were screened for plasmids lacking a StuI site but containing a BglII site at the position of the former StuI site. A representative plasmid was isolated and designated pBK-$J_L$(StuI/BglII) (see: FIG. 2).

D. Cloning of pBUK:BglII-B

The 31.6 kbp BglII-B fragment of PRV(BUK-7) was cloned into the BamHI site of pBR322 as follows (see: FIGS. 1 and 4).

4.0 μg of PRV(BUK-7) DNA was dissolved in 100 μl of BglII cutting buffer and digested with 32 units of BglII (New England BioLabs, Inc.) for 1 hr at 37° C. The reaction was terminated by adding an equal volume of 90% (v/v) redistilled phenol, mixing, and centrifuging for phase separation. After dialysis of the aqueous phase against 0.1 X TE buffer, sodium acetate was added to 0.1M followed by the addition of 2 volumes of ethanol, and the DNA precipitate was stored at −20° C. overnight. The DNA precipitate was collected by centrifugation and redissolved in 0.1 X TE buffer.

The restriction nuclease fragments were then combined with BamHI-digested, dephosphorylated pBR322 in the following manner:

4.0 μg of BglII-digested PRV(BUK-7) DNA was mixed with 0.2 μg of BamHI-digested, dephosphorylated pBR322 DNA (New England BioLabs, Inc.) in 0.05 ml of ligation buffer and containing 1000 units of T4 DNA ligase (New England BioLabs, Inc.), and incubated overnight at 4° C. The reaction was terminated by adding EDTA to 20 mM and heating at 65° C. for 10 min. The recombinant DNA plasmid was used to transform *E. coli* K12 strain RR1, as described above, and the resulting colonies were screened by the rapid plasmid screening procedure described above. A plasmid, about 35 Kbp in size, comprising the approximately 31.6 Kpb BglII-B fragment of PRV(BUK-7) cloned into the BamHI site of pBR322 was isolated and designated pBUK:BglII-B.

E. Subcloning pBUK-BglII-B and Construction of pBUK:Stu12

The StuI fragment from pBUK:BglII-B, which maps at about 11 to 21 map units (see: FIG. 4), was transferred to the BamHI site of pBR322 by the following procedure.

1.0 μg of pBUK-BglII-B was dissolved in 100 μl of StuI cutting buffer. The DNA was digested by the addition of 10 units of StuI (New England BioLabs, Inc.) and incubated at 37° C. for 1 hr. The reaction was terminated by the addition of CDTA to 20 mM and sodium acetate to 0.2M, followed by heating at 65° C. for 30 min. The DNA was precipitated with ethanol and collected by centrifugation as described above.

The StuI-digested pBUK:BglII-B was dissolved in 25 μl of ligation buffer containing 1.0 μg of phosphorylated BglII linker (New England BioLabs, Inc.) and 1000 units of T4 DNA ligase. After overnight incubation at 4° C., the reaction was terminated by adding EDTA to 20 mM and heating at 65° C. for 10 min. The StuI-digested pBUK:BglII-B, now possessing concatenated BglII linkers at the former StuI termini, was separated from the unligated BglII linkers by layering the reaction mixture on a 10–40% (w/v) sucrose gradient in 50 mM NaCl, 10 mM Tris-Hcl (pH 7.5), 1.0 mM EDTA, and centrifuging for 8 hr at 40,000 rpm at 4° C. in an SW41 Spinco rotor. Fractions were collected and the DNA located by analyzing aliquots on agarose gel electrophoresis as described above. The linkers remained at the top of the gradient, whereas the plasmid DNA sedimented to the middle of the gradient. After adding sodium acetate to 0.1M and 2.0 μg of carrier yeast tRNA to each fraction, the plasmid DNA was precipitated with ethanol, collected by centrifugation, dissolved in 50 μl of BglII cutting buffer, and then digested with 8 units of BglII (New England Biolabs, Inc.) at 37° C. for 1 hr in order to create BglII cohesive ends. The reaction was terminated, the DNA was precipitated with ethanol, and collected by centrifugation, as described above.

The StuI-digested pBUK:BglII-B, now containing BglII cohesive ends on the StuI fragments, was cloned into the BamHI site of pBR322 by first dissolving the DNA in 50 μl of ligation buffer. Then, 0.1 μg of BamHI-digested, dephosphorylated pBR322 was added and the mixture was ligated with 1000 units of T4 DNA ligase, as described above. After termination of the ligation reaction *E. coli* K12 RR1 was transformed with the hybrid plasmids and the resulting colonies were screened for recombinants, as described above. A 16 Kbp plasmid containing a 12 Kbp StuI fragment derived from pBUK:BglII-B inserted in the BamHI site of pBR322 was isolated and designated pBUK:Stul2.

F. Construction of pPRVTK/STUl2

A hybrid plasmid comprising a selectable gene, i.e., the PRV tk gene, inserted into the PRV g92 gene was constructed by transferring the 3.1 kb BglII-KpnI fragment from pBK-$J_L$(StuI/BglII) into the BamHI and KpnI sites of pBUK:Stul2 as follows (see: FIG. 3):

4.0 μg of pBUK:Stul2 was dissolved in 200 μl of a buffer comprising 150 mM NaCl, 6.0 mM Tris-HCL (pH 7.9), 6.0 mM $MgCl_2$, 100 μg/ml BSA (hereinafter "BamHI cutting buffer"), and digested with 10 units of BamHI (New England BioLabs, Inc.) for 2 hr at 37° C. The reaction was terminated by adding CDTA to 20 mM and sodium acetate to 0.1M, followed by heating at 65° C. for 30 min. The DNA was precipitated with ethanol and collected by centrifugation. Subsequently, the DNA was dissolved in 200 μl of KpnI cutting buffer and digested with 20 units of KpnI for 2 hr at 37° C. followed by termination of the reaction with CDTA added to 20 mM and heating to 65° C. for 30 min. Then, sodium acetate was added to 0.3M and the DNA was ethanol precipitated and collected by centrifugation.

The combined KpnI and BamHI cuts resulted in two fragments of about 0.4 and 15.6 Kbp. In order to minimize religation of the small fragment into its original position during the subsequent steps, these two fragments were separated by centrifugation on a sucrose gradient as follows:

The KpnI- and BamHI-digested pBUK:Stul2 fragments were dissolved in 100 μl of TE buffer and layered on top of a 10–40% (w/v) sucrose gradient as described above and sedimented by centrifugation in a Spinco SW41 rotor at 40,000 rpm for 8 hr at 4° C. Fractions were collected and the positions of the DNA fragments were located by agarose gel electrophoresis analyses of portions of each fraction as described above. To the fraction containing the large DNA fragment, sodium acetate to 0.3M and also 2.0 μg of yeast tRNA were added, followed by ethanol precipitation and collection of the DNA by centrifugation.

Then, 2.0 μg of pBK-$J_L$(StuI/BglII) was dissolved in 100 μl of KpnI cutting buffer and digested with 10 units of KpnI for 1 hr at 37° C. The reaction was terminated and the DNA was ethanol precipitated and collected by centrifugation as described above. Next, the KpnI-digested pBK-$J_L$(StuI/BglII) was redissolved in 100 μl of BglII cutting buffer and digested with 10 units of BglII (New England Biolabs, Inc.) for 2 hr at 37° C. After termination of the reaction, the DNA was ethanol precipitated and collected by centrifugation. In order to minimize religation of these fragments in subsequent steps, the KpnI- plus BglII-digested pBK-$J_L$(StuI/BglII) fragments were dephosphorylated in 100 μl of a buffer comprising 50 mM Tris-HCl (pH 8.0), 50 mM NaCl (hereinafter "alkaline phosphatase buffer") and digested with 0.2 units of bacterial alkaline phosphatase (International Biotechnologies) at 65° C. for 1 hr. The reaction was terminated by adding proteinase K to 100 μg/ml and incubating for 1 hr at 37° C., followed by adding an equal volume of redistilled 90% (v/v) phenol. After shaking, the aqueous phase was collected and extracted with ether to remove residual phenol. The DNA was precipitated with ethanol and collected by centrifugation.

Finally, the PRV tk gene was transferred into the PRV g92 gene by ligating the KpnI- and BamHI-digested pBUK:Stul2 with the dephosphorylated and KpnI- and BglII-digested pBK-$J_L$(StuI/BglII) in 50 μl of ligation buffer and 1000 units of T4 DNA ligase overnight at 4° C. The reaction was terminated as described above, and the plasmid DNA transfected into *E. coli* K12 strain RRl as described above. Candidate recombinant plasmids were screened by the rapid screening procedure as described above and a 19 Kbp plasmid lacking the 0.4 Kbp KpnI to BamHI fragment of pBUK:Stul2, but containing an insert of the 3.1 Kbp KpnI to BglII fragment of pBK-$J_L$(StuI/BglII) was obtained. This plasmid was designated pPRVTK/STUl2.

G. Construction of pBUK:Stul2/PstI

In order to construct a plasmid with a deletion in PRV g92 gene, a 4.0 Kbp PstI fragment containing the PRV g92 gene was subcloned from the 16 Kbp pBUK:Stul2 plasmid into the PstI site of pBR322 as follows (see: FIG. 4):

2.0 μg of pBUK:Stul2 was dissolved in 100 μl of a buffer comprising 100 mM NaCl, 10 mM Tris-HCL (pH 7.5), 10 mM $MgCl_2$, 100 μg/ml BSA (hereinafter "PstI cutting buffer") and digested with 10 units of PstI (New England BioLabs, Inc.) for 1 hr at 37° C. The reaction was terminated by the addition of CDTA to 20 mM and heating at 65° C. for 30 min. Then, sodium acetate was added to 0.1M and the DNA was ethanol precipitated and collected by centrifugation. The 4 Kbp PstI fragment of pBUK:Stul2 was cloned into the PstI site of pBR322 by dissolving the plasmid DNA in 50 μl of ligation buffer containing 0.2 μg of PstI-digested and dephosphorylated pBR322 (New England BioLabs, Inc.) and 1000 units of T4 DNA ligase, then incubating at 4° C. overnight. The reaction was terminated by the addition of EDTA to 20 mM and heating at 65° C. for 10 min. The recombinant DNA was introduced into *E. coli* K12 RRl by transformation, and colonies were screened by the rapid plasmid screening procedure, as described above, for a plasmid about 8.4 Kbp in size and containing the 4.0 Kbp PstI fragment from pBUK:Stul2 inserted into the PstI site of pBR322 (see: FIG. 4). In this manner, a representative recombinant plasmid was isolated and was designated pBUK:Stul2/PstI.

H. Construction of pBUK:gCdlSal

A plasmid with a 1.1 SalI deletion in the PRV g92 gene from 5.2 to 6.3 map units of pBUK:Stul2/PstI was constructed as follows (see: FIG. 4):

0.25 μg of pBUK:Stu12/PstI was dissolved in a buffer comprising 150 mM NaCl, 6.0 mM Tris-HCL (pH 7.9), 6.0 mM $MgCl_2$, 6.0 mM 2-mercaptoethanol, 100 μg/ml BSA (hereinafter "SalI cutting buffer") and digested by 1.5 units of SalI (New England BioLabs, Inc.) for 1 hr at 37° C. Then, the reaction was terminated by the addition of CDTA to 20 mM and heating at 65° C. Sodium acetate was added to 0.1M and the DNA then ethanol precipitated and collected by centrifugation. This procedure introduced a series of partial SalI cuts in plasmid pBUK:Stul2/PstI.

The partially digested pBUK:Stul2/PstI was then redissolved in 50 μl of ligation buffer and incubated in the presence of 1000 units of T4 DNA ligase overnight at 4° C. The reaction was terminated by the addition of EDTA to 20 mM and heating at 65° C. for 10 min. The plasmid DNA was introduced into bacteria by transformation of *E. coli* K12 RRl, as described above, and the resulting colonies were analyzed by the rapid screening procedure, as described above, until a plasmid was obtained which had a 1.1 Kbp deletion of pBUK:Stul2/PstI extending from map units 5.2 to 6.3. The desired plasmid was designated pBUK:gCdlSal (see: FIG. 4).

I. Construction of PRV(dltk):PRVTK/STUl2

In order to obtain, by homologous recombination, a recombinant PRV with a selectable gene, i.e., a functional PRV tk gene, inserted into the PRV g92 gene, it was necessary to start with intact, infections DNA of a $tk^-$ PRV strain and a hybrid plasmid containing a functional PRV tk gene inserted into a deletion within the coding region of the PRV g92 gene (see: FIG. 5). The progeny virus obtained following this type of cross mainly comprise parental $tk^-$ PRV and $tk^+$ PRV rescued by homologous recombination at the tk gene locus. In order to obtain $tk^+$ PRV recombinants containing a functional PRV tk gene inserted into the g92 gene, it was necessary to enrich and screen for the desired recombinants as follows:

The $tk^+$ PRV was enriched for by growth of the progeny of the above cross in $tk^-$ rabbit cells (i.e., RAB(BU)) (see: Kit, S. and Qavi, H., *Virol.* 130: 381–389 (1983)) in the presence of HATG containing growth medium, since HATG inhibits $tk^-$ PRV replication and favors the outgrowth of $tk^+$ PRV. The enriched population of $tk^+$ PRV were then screened by molecular hybridization to identify virus clones which have a functional PRV tk gene inserted into a deletion within the PRV g92 gene.

The hybrid plasmid chosen for the construction of the above described PRV recombinant was pPRVTK/STUl2 (see: FIG. 3). However, other hybrid plasmids containing larger or smaller flanking sequences adjacent to the coding sequences of a functional PRV tk gene or the g92 gene, or larger or smaller deletions in other portions of the g92 gene, could be employed to create a $tk^+$ PRV recombinant with a functional PRV tk gene inserted into a deletion within the g92 gene, or inserted directly into the g92 gene, such that the formation of any antigenic g92 polypeptides is prevented. Convenient restriction nuclease sites for the construction of the deletion and/or insertion mutations in the g92 gene can be ascertained from an examination of the restriction map of the g92 DNA fragment of plasmid pBUK:Stul2/PstI (see: FIG. 4) and from the restriction nuclease cleavage sites, shown in Table 2 below, which are predicted from the nucleotide sequence of the 2.4 Kbp NcoI to MluI DNA fragment which contains the coding sequences of the g92 gene (see: Robbins, A. K., Presentations at the Ninth International Herpesvirus Workshop, Seattle, Wash., Aug. 24–29 (1984)).

TABLE 2

RESTRICTION NUCLEASE CLEAVAGE SITES OF 2.4 Kbp NcoI TO MluI DNA FRAGMENT CONTAINING THE PRV g92 GENE*

| Restriction endonuclease | Location of first nucleotide in sequence (Nucleotide number) |
|---|---|
| NcoI | 1, 294 |
| XhoI | 100, 1553 |
| MluI | 2370 |
| ApaI | 163, 1529 |
| AhaIII | 253 |
| SalI | 364, 1535 |
| ScaI | 738 |
| SacI | 764, 1166 |
| DdeIC | 1016 |
| HpHIA | 1040, 1195 |
| AATII | 1214, 1734 |
| SmaI | 1219 |
| NotI | 1229 |
| XmaIII | 1230 |
| KpnI | 1284 |
| BglI | 1551 |
| PvuII | 1571 |
| NaeI | 1661 |
| BamHI | 1671 |
| Sau3AI | 1648, 1672 |
| BalI | 1677 |

*See FIG. 4, plasmid pBUK:Stu12/PstI; map units 4.9 (NcoI) to 7.3 (MluI).

The tk− PRV DNA chosen for the recombination step was PRV(BUK-dl 3) (ATCC No. VR-2074) (see: U.S. Pat. No. 4,514,497). Since PRV(BUK-dl 3) contained a deletion in the tk gene, and is a virus strain with known superiority as a vaccine, it was the preferred virus to other tk− PRV vaccine strains for the construction of the above-described recombinant. However, other tk− PRV strains, such as spontaneous tk− mutants or mutagen-induced tk− mutants, e.g., PRV(BUK-5A) (ATCC No. VR-2078) (see: U.S. Pat. No. 4,514,497), could also be employed without departing from the scope and spirit of this invention.

The construction of the recombinant tk+ PRV containing a functional PRV tk gene inserted into a deletion within the g92 gene of PRV(BUK-dl 3) was carried out as follows:

RAB-9 cells were seeded in 60 mm Petri dishes ($0.2\times10^6$ cells/dish) and incubated at 37° C. for 48 hr. Then, the following sterile solutions were added to a test tube in sequential order:

(1) 0.02 ml of a 50 μg/ml solution of PRV(BUK-dl 3) DNA in TE buffer;

(2) 0.2 ml of a 10 μg/ml solution of hybrid plasmid pPRVTK/STUl2;

(3) 0.65 ml of water;

(4) 1.0 ml of a 20 μg/ml solution of salmon sperm DNA in 2 X a HEPES buffer solution comprising 8.0 g/l NaCl, 0.37 g/l KCl, 0.125 g/l $Na_2HPO_4.2H_2O$, 1.0 g/l glucose, 5.0 g/l HEPES, pH 7.05; and (5) 0.13 ml of 2.0M $CaCl_2$.

The resulting solution was mixed by inversion and kept at room temperature for 30 min while a DNA-calcium phosphate precipitate formed. Then, 0.5 ml of the suspension containing a calcium phosphate precipitate of DNA was added directly to 5.0 ml of growth medium and plated on RAB-9 cells which had been seeded in 60 mm Petri dishes 48 hr earlier. The cells were incubated at 37° C. for 5 hr. Then, the media was aspirated, and the monolayer rinsed with 5.0 ml of fresh growth media, followed by the addition of 1.0 ml of a solution of a 1 X HEPES buffer solution plus 15% (v/v) glycerol. After a 3-min incubation at room temperature, the solution was aspirated, the monolayer rinsed with media again, and fresh growth media added. The culture was incubated at 34.5° C. for 2 days until extensive cytopathic effects occurred. A virus harvest was then made as described above and stored at −80° C. The virus harvest was then titrated in RAB-9 cells under agar overlay.

The virus harvest from the cotransfection was thawed, sonicated, and diluted in growth media containing HATG. In order to enrich for tk+ PRV recombinants, the harvested virus was diluted to give an input multiplicity of 0.01 PFU/cell and passaged in confluent monolayer cultures of RAB(BU) cells in 8-oz prescription bottles in growth medium supplemented with HATG. After a 1-hr absorption at 37° C., the infected monolayer cultures were washed three times with a solution comprising 8.0 g NaCl, 0.4 g KCl, 0.1 g glucose and 0.02 g phenol red per liter of water (hereinafter "GKN"). Then, growth medium containing HATG was added, incubation was continued at 34.5° C. for 48 hr, and virus harvests were made. The harvest of the selection step was titrated in RAB-9 cells, candidate recombinant tk+ PRV picked at random from plaques, and virus pools were prepared. In this manner, 96 tk+ PRV candidate recombinants were obtained.

J. Preparation of Probes for Molecular Hybridization

To identify candidate recombinant PRV mutants with a deletion in the PRV tk gene and a deletion and/or insertion in the PRV g92 gene, molecular hybridization experiments with $^{32}P$-labeled probes were carried out. These probes were as follows:

(1) Ml3mpl9/BB2(KpnI-BamHI)

This probe was prepared by nick-translation of the RF form of phage Ml3mpl9/BB2(KpnI-BamHI), which, in turn, was prepared by inserting the 0.38 Kbp KpnI to BamHI nucleotide sequence of plasmid pBB2 into the polycloning sites of phage Ml3mpl9 (see: Yanisch-Perron, C., Vieira, J., and Messing, J., *Gene* 33:103–119 (1985)). Plasmid pBB2 comprises the BamHI-2 fragment of PRV(BUK-5) cloned at the BamHI restriction site of pBR322. The 0.38 Kbp KpnI to BamHI fragment spans about one-fourth of the PRV g92 structural gene at the 3′ end of the gene. More specifically, phage M13mp19/BB2(KpnI-BAmHI) was prepared as follows:

One μg of pBB2 and 0.1 μg of the RF DNA of Ml3mpl9 were incubated at 37° C. in a reaction mixture comprising 6.0 mM NaCl, 6.0 mM Tris HCl (pH 7.5), 6.0 mM $MgCl_2$, 6.0 mM 2-mercaptoethanol, 100 μg/ml BSA, and 10 units of KpnI. After a 1-hr incubation, 10 μl to 10 X a BamHI buffer comprising 1.5M NaCl, 60 mM Tris-HCl (pH 7.9), 60 mM $MgCl_2$, 1.0 mg/ml BSA, 10 units of BamHI and water to 100 μl were added. Then, the reaction mixture was further incubated at 37° C. for 1 hr. The reaction was terminated by adding 10 μl of 0.25M EDTA (pH 7.6) and heating at 65° C. for 10 min. The mixture was extracted once with phenol:chloroform (1 vol:1 vol) and the DNA was precipitated from the aqueous phase by adding 0.1 volume of 3.0M sodium acetate (pH 7.6) and 2.2 volumes of ethanol. The DNA precipitate was rinsed once with ethanol and dried in vacuo.

The digested DNA was ligated in a 40 μl reaction mixture comprising 50 mM Tris-HCl (pH 7.8), 10 mM $MgCl_2$, 20 mM dithiothreitol, 1.0 mM ATP, 50 μg/ml BSA, and 400 units of T4 ligase. The reaction was carried out at 4° C. for 18 hr and terminated by adding 160 μl TE buffer and heating at 65° C. for 10 min. The resulting recombinant phage were used to transform $CaCl_2$-activated *E. coli* JMlO5 bacteria as described above and screened for transformants containing the 0.38 Kbp KpnI to BamHI inserted fragment. Nick-translated probes were then prepared from the desired hybrid phage, namely, Ml3mpl9/BB2(KpnI-BamHI) as follows:

To 25 μl of a reaction mixture comprising 6.0 μmol PBS, pH 7.4, 1.8 nmol dATP, 1.8 nmol dGTP, 0.1 mCi ($\alpha$-$^{32}$P)dTTP (400 Ci/mmole), 0.1 mCi ($\alpha$-$^{32}$P)dCTP (400 Ci/mmole) (Amersham Corporation), about 1.0 μg of the hybrid phage DNA was added. Then, 1.33 ng of DNase I (Worthington Biochemicals) in 1.0 μl of a solution comprising 10 mM Tris-HCl, pH 7.5, 5.0 mM $MgCl_2$ and 100 μg/ml BSA, was added and the reaction mixture was allowed to stand for 1 min at room temperature. Next, the reaction mixture was incubated at 14° C. with 5.0 units of *E. coli* DNA polymerase I (Boehringer-Mannheim Biochemicals) in 1.0 μl of a solution comprising 50 mM potassium phosphate buffer, pH 7.0, 2.5 mM dithiothreitol and 50% (v/v) glycerol. When the specific activity became higher than $2\times10^8$ cpm/μg DNA, i.e., about 3 hr, the reaction was terminated by adding 10 μl of 0.25M EDTA (pH 7.4) and heating at 68° C. for 10 min. Then, as carrier, 50 μl of a solution comprising 5.0 mg/ml sonicated salmon sperm DNA in TE buffer was added to the mixture and the nick-translated DNA was purified by Sephadex G50 (fine) column chromatography using 10 mM NaCl, 10 mM Tris-HCl, pH 6.5, 2.0 mM EDTA as the elution buffer.

The resulting $^{32}$P-labeled, nick-translated DNA was used as a probe in DNA-DNA hybridization experiments after boiling in a water bath for 20 min, and quickly cooling on ice to form single-stranded DNA (see: Rigby, P. W. J., Dieckmann, M., Rhodès, G., and Berg, P., *J. Mol. Biol.* 113:237-251 (1977)).

(2) pBTK probe

This probe was prepared by nick-translation of plasmid pBTK as described above. Plasmid pBTK was derived from pBK-$J_L$ by deleting the EcoRI to StuI fragment (0 to 4.8 map units of pBK-$J_L$) as described below.

0.25 μg of pBK-$J_L$ was dissolved in 50 μl of StuI cutting buffer and digested with 2 units of StuI (New England BioLabs, Inc.) for 2 hr at 37° C. Then, Tris-HCl (pH 7.5) was added to 100 mM and the StuI-digested plasmid was further digested with 5 units of EcoRI (New England BioLabs, Inc.) for 1 hr at 37° C. The reaction was terminated by deproteinization with an equal volume of redistilled 90% (v/v) phenol and the aqueous phase was separated by centrifugation. The aqueous phase containing the digested plasmid DNA was then extracted with ether and dialyzed against 0.1 X TE, then brought to 0.3M sodium acetate and ethanol precipitated. The plasmid DNA was collected by centrifugation, redissolved in 25 μl of a buffer comprising 6.0 mM Tris-HCl (pH 7.5), 1.0 mM dithiothreitol, 6.0 mM $MgCl_2$, 50 mM NaCl (hereinafter "Hin buffer"), and 0.1 mM each of dATP, dCTP, dGTP, and dTTP. Then 2 units of the Klenow fragment of *E. coli* DNA polymerase I was added, and the reaction mixture was incubated for 30 min at 22° C. This reaction filled in the cohesive EcoRI end, converting it to a blunt end. The reaction was terminated by heating at 70° C. for 5 min. An equal volume of 2× ligation buffer was added, and religation accomplished by adding 1000 units of T4 DNA ligase and incubating at 4° C. overnight. The reaction was terminated by the addition of EDTA to 20 mM and heating at 65° C. for 10 min. *E. coli* K12 strain RR1 was transformed with the religated DNA and colonies screened by the rapid plasmid screening procedure as described above until a 7.5 Kbp plasmid containing an EcoRI to StuI deletion was obtained. The plasmid was designated pBTK.

(3) pSal probe

This probe was prepared by nick-translation of plasmid pSal as described above. Plasmid pSal was derived from pBUK:Stul2/PstI by subcloning the 1.1 Kbp SalI fragment of pBUK:Stu12/PstI (5.2 to 6.3 map units (see: FIG. 4) into the SalI site of pBR322 as described below.

1.0 μg of pBUK:Stu12/PstI was dissolved in 50 μl of SalI cutting buffer and digested with 20 units of SalI (New England BioLabs, Inc.) for 1 hr at 37° C. Also, 1.0 μg of pBR322 was treated in the same manner. The reactions were separately terminated by adding CDTA to 20 mM and heating at 65° C. for 30 min. The SalI-digested plasmids were then pooled. Next, sodium acetate was added to 0.1M and the DNA was precipitated by the addition of 2 volumes of ethanol. The DNA was collected by centrifugation and redissolved in 50 μl of ligation buffer with 1000 units of T4 DNA ligase. After an overnight incubation at 4° C., the reaction was terminated by the addition of EDTA to 20 mM and heating at 65° C. for 10 min. *E. coli* K12 strain RR1 was transformed with the ligated DNA, and colonies of $Amp^R$ $Tet^S$ phenotypes were analyzed by the rapid plasmid screening procedure as described above. A clone was isolated which contained the 1.1 Kbp SalI fragment of pBUK:Stu12/PstI inserted into the SalI site of pBR322 and was designated pSal.

(4) pBUK:Stu12/PstI probe

This probe was prepared by nick-translation of plasmid pBUK:Stu12/PstI as described above.

(5) Oligo-006 probe

This probe was prepared by phosphorylation with polynucleotide kinase of the terminal nucleotide of oligonucleotide-006 described below. Oligonucleotide-006 was synthesized by the phosphoramidite chemistry method on an automated DNA synthesizer (Systec, Inc.) according to manufacturer's instructions, and has the following nucleotide sequence:

5'-GCGCCGCGCTTCGACCAGACC-3'.

This sequence is part of a small SacI fragment derived from the BamHI-11 fragment of PRV(BUK-5) and is a portion of the approximately 150 bp sequence deleted from the tk gene of PRV(BUK-dl 3) (see: U.S. Pat. No. 4,514,497)).

50 picomoles of oligonucleotide-006 was added to a reaction mixture comprising 150 μCi ($\gamma$-$^{32}$P)ATP, 70 mM Tris-HCl (pH 7.6), 10 mM $MgCl_2$, 5.0 mM dithiothreitol), and 5 units of T4 polynucleotide kinase (New England BioLabs, Inc.). The mixture was incubated for 1 hr at 37° C. and the reaction was terminated by adding EDTA to 20 mM, followed by purification of the labeled oligonucleotide-006 by gel filtration on gel P4 (Bio-Rad, Inc.) to remove the unreacted ($\gamma$-$^{32}$P)ATP. The elution buffer was the same as that used for Sephadex G-50 chromatography discussed above. The probe was not heat-treated before use, since it was already single-stranded.

K. Identification of Recombinant tk+ PRV Containing a functional PRV tk Gene Inserted into the Deletion in the PRV g92 Gene PRV DNAs prepared from the candidate recombinants described above were analyzed by the dot-blot method (see: Brandsma, J. and Miller, G., *Proc. Nat. Acad. Sci. USA* 77: 6851–6855 (1980)) to identify viruses that lacked the 0.4 Kbp KpnI to BamHI fragment of BamHI-2. This fragment is part of the coding sequence of the PRV g92 gene and was cloned in phage M13mp19, as described above, to yield the phage described M13mp19/BB2(KpnI-BamHI). A nick-translated, $^{32}$P-labeled probe of the double-stranded (RF) form of M13mp19/BB2(KpnI-BamHI) was then used as a probe in these dot-blot, and the subsequent Southern blot, molecular hybridization experiments.

Specifically, 24-well multiwell tissue culture trays containing confluent monolayers of RAB-9 cells were infected with 0.05 ml of undiluted candidate virus and incubated at 34.5° C. for 8 hr. The virus inoculum was aspirated, the wells rinsed with 1.0 ml of GKN, and 0.2 ml of 0.5M NaOH was added to each well to lyse the cells and release the DNA. After storage at room temperature overnight, 0.3 ml of 1.0M Tris-HCl (pH 7.5) and 0.5 ml of 20× a buffer comprising 0.15M NaCl, 0.015M sodium citrate, pH 7.0 (hereinafter "SSC") were added per well. For dot-blot analysis, nitrocellulose filters in a 96-well Schleicher and Schuell filtration apparatus was used. The filters were washed with water and with 1×SSC prior to the addition of the DNA samples. To bake the DNA samples to the filters, the nitrocellulose filters were dried, heated overnight at 60° C. in a vacuum desiccator, and then heated for 2 hr at 80° C. The filter was placed in a plastic sealable pouch containing 50 ml of 3×SSC, 0.02% (w/v) Ficoll, 0.02% (w/v) BSA, 0.02% (w/v) polyvinylpyrrollidone, 50 μg/ml of boiled and alkali-denatured salmon sperm DNA (hereinafter "modified Denhardt's solution"), 10 μg/ml poly(A), and incubated overnight at 60° C. with shaking. Alkaline salmon sperm DNA was added from a stock solution of about 5.0 mg/ml prepared by dissolving 50 mg of salmon sperm DNA in 10 ml of 0.2N NaOH, heating at 100° C. for 20 min to denature, and shearing the DNA to about 0.4 Kbp segments, and then neutralizing with 0.2 ml of 10N HCl.

The modified Denhardt's solution was then replaced with 50 ml of hybridization buffer comprising 50% (w/v) formamide, 0.6M NaCl, 0.2M Tris-HCl, pH 8.0, 0.02M EDTA, 0.1% (w/v) sodium dodecylsulfate, 50 μg/ml alkali-denatured salmon sperm DNA, and 10 μg/ml poly(A) (hereinafter "hybridization buffer"). Next, air bubbles were squeezed out of the bag which was then sealed using an Oster Touch-a-Matic Bag Sealer and incubated at 37° C. for 1 hr on a shaker.

Thereafter, about 1.0 ml, containing about $10^7$ cpm and 50 ng of the ($^{32}$P) nick-translated M13mp19/BB2(KpnI-BamHI) probe, obtained as described below, was added to the bag with a 3.0 ml syringe by piercing the side of the bag at a corner. Next, the bag was resealed and incubated at 37° C. for up to 48 hr on a shaker to allow for hybridization.

After hybridization had been accomplished, the bag was cut and the solution was decanted. The filter was then carefully removed and placed in a tray containing about 100 ml of hybridization buffer plus 50 μg/ml denatured salmon sperm DNA for the first wash only, but no poly(A) in any wash. The filter was washed for 30 min at 37° C. five times with gentle shaking. Next, the filter was washed for 30 min at 37° C. with 0.3×SSC and then placed on filter paper to dry overnight at room temperature.

For autoradiography, the filter was replaced on a thin piece of cardboard covered with Saran-Wrap, and exposed to Fuji X-ray film with an intensifying screen for periods of 5 hr to 2 days at −70° C. One out of the 96 candidate viruses did not hybridize to the $^{32}$P-labeled M13mp19/BB2(KpnI-BamHI) probe, indicating that this nonhybridizing clone had a deletion in the KpnI to BamHI sequence of the PRV g92 gene. This clone was designated PRV(dltk):PRVTK/STU12 (see: FIG. 5).

Figure 6A:
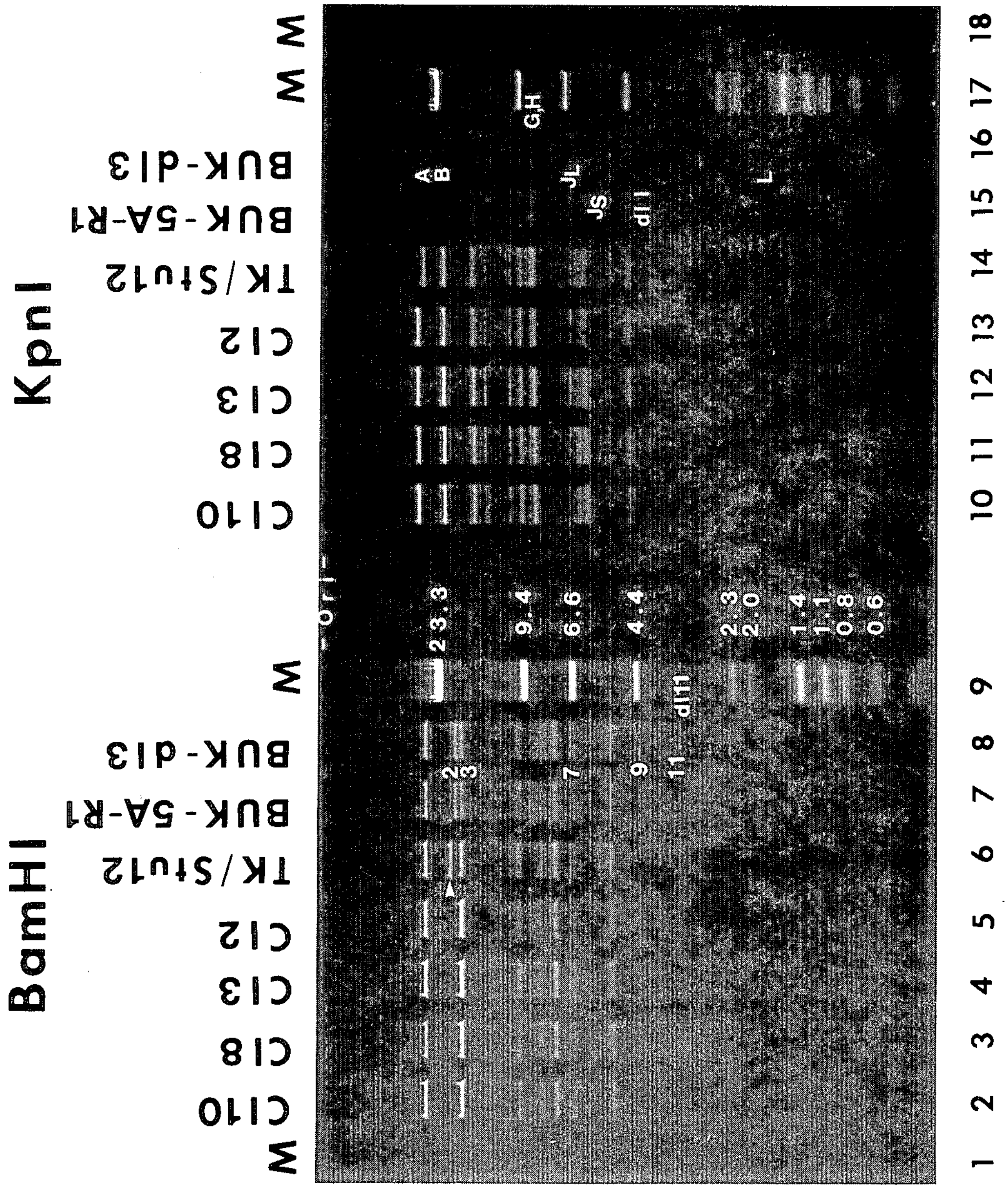
FIG. 6A shows ethidium bromide-stained agarose gel fragments of BamHI- and KpnI-digested DNA from parental and recombinant PRV(Bucharest) strains. Lanes 2 and 10, 3 and 11, 4 and 12 and 5 and 13 show Clones 10, 8, 3, and 2, respectively. These clones are candidate recombinant $tk^-$ PRV(dlg92/dltk) viruses with deletions in the g92 and tk genes. The $tk^+$ PRV(BUK-5A-R1) in lanes 7 and 15 is the parental virus used in the construction of the $tk^-$ deletion mutant PRV(BUK-dl 3) shown in lanes 8 and 16 (see: Kit, S., Kit, M., and Pirtle, E. C., *Am. J. Vet. Res.* 46: 1359–1367 (1985) and U.S. Pat. No. 4,514,497). Lanes 6 and 14 show the $tk^+$ recombinant PRV(dltk):PRVTK/STU12 (see.

Viral DNA of high purity was prepared from the tk+ PRV(dltk):PRVTK/STU12 as described above. Then, 0.5 μg of viral DNA from this candidate deletion mutant was digested with restriction nucleases, KpnI and BamHI, under conditions specified by New England BioLabs, Inc., and the fragments were separated by electrophoresis on 0.6% (w/v) agarose at 35 volts at constant voltage for 16 hr at 4° C. The electrophoresis buffer was 0.04M Trizma base, pH 8.1, 0.03M $NaH_2PO_4$, and 0.001M EDTA. Restriction nuclease fragments of the parental tk− PRV(BUK-dl 3) (see: FIG. 6A, lanes 8 and 16), the parent tk+ strain fron which PRV(BUK-dl 3) was derived, i.e., PRV(BUK-5A-R1) (see: FIG. 6A, lanes 7 and 15 and U.S. Pat. No. 4,514,497) and marker fragments obtained by HindIII digestion of phage lambda DNA and HaeIII digestion of phage ΦX174 RF DNA (see: FIG. 6A, lanes 1, 9, 17 and 18) were also electrophoresed. The agarose gel was stained with 0.5 μg/ml ethidium bromide dissolved in electrophoresis buffer, and photographed under shortwave UV illumination. The ethidium bromide-stained gel revealed that the 6.1 Kbp KpnI-$J_L$ fragment of PRV(BUK-dl 3) had disappeared in the recombinant tk30 PRV(dltk):PRVTK/STU12 and had been replaced with an 8.6 Kbp hypermolar band comigrating with the KpnI-G/H fragments (see: FIG. 6A, lanes 14 and 16). Also, the 17.8 Kbp BamHI-2 fragment of PRV(BUK-dl 3) had disappeared in the recombinant tk+ PRV(dltk):PRVTK/STU12 and was replaced by a novel, slower migrating BamHI fragment of about 19.2 Kbp (see: FIG. 6A, lanes 6 and 8). These results are consistent with the deletion of the 0.4 Kbp KpnI-BamHI fragment from the PRV g92 gene, and its replacement with the 3.1 Kbp BglII to KpnI fragment of pBK-$J_L$(Stu/BglII), which contains the PRV tk gene.

The separated DNA restriction fragments in the agarose gel were next transferred to nitrocellulose filters (Schleicher and Schuell) by the Southern blotting procedure (see: Southern, E. M., *J. Mol. Biol.* 98: 503–513 (1975)) in the following manner:

The agarose gel was placed in a glass baking tray containing 1.0M KOH for 30 min at room temperature and, then, in a glass baking tray containing 1.0M Tris-HCl, pH 7.0, and 0.6M NaCl for 60 min at room temperature. The treated gel was then transferred to a blot apparatus (Bethesda Research Laboratories, Inc.).

A nitrocellulose filter was prewetted in water for 10 min and then in 20×SSC for 5 min. Next, the filter was placed on the gel. Using 20×SSC as the transfer fluid, blotting was allowed to proceed for about 24 hr. The adherent gel was removed from the nitrocellulose filter, and the filter was rinsed with 6×SSC, dried at room temperature for several hours, and then in a vacuum desiccator overnight at 60° C. This was followed by 2 hr of baking at 80° C. The nitrocellulose filters were removed from the desiccator and placed in Dazey Seal-a-Meal cooking bags.

The filter was first pretreated overnight at 60° C. with 50 ml of modified Denhardt's solution and hybridization buffer at 37° C. as described above.

The nitrocellulose filters from two separate gels were next hybridized to two different $^{32}P$-labeled, nick-translated probes, i.e.: (i) pBTK and (ii) M13mp19/BB2(KpnI-BamHI). The procedure for molecular hybridization of the probes to the nitrocellulose filters and the washing step were the same as described above.

The pBTK probe contains the entire tk gene, but none of the PRV g92 gene sequences. The pBTK probe hybridized to specific fragments of the candidate recombinant virus as well as to those of the parental PRV(BUK-dl 3). As expected, hybridization occurred to the 6.1 Kbp KpnI-$J_L$ fragment of PRV(BUK-dl 3) and to a new 8.6 Kbp fragment in the recombinant. Also, hybridization occurred to both the BamHI-11 and the BamHI-9 fragments of PRV(BUK-dl 3). With regard to the recombinant tk+ PRV(dltk):PRVTK/STUl2, the pBTK probe hybridized to the BamHI-11 fragment and to a new BamHI fragment, about 19.2 Kbp in size. This demonstrated that the PRV tk gene had been inserted into the g92 gene in the recombinant.

The M13mp19/BB2(KpnI-BamHI) probe hybridized to the KpnI-$J_L$ and BamHI-2 fragments of PRV(BUK-dl 3), but there was no hybridization to any fragments of the recombinant, indicating that the 0.4 Kbp KpnI-BamHI fragment had been deleted from the PRV g92 gene. These experiments conclusively demonstrate that the tk+ PRV(dltk):PRVTK/STUl2 virus had a selectable gene, i.e., a functional PRV tk gene, inserted into a deletion of the PRV g92 gene.

L. Construction of PRV(dlg92/dltk)

In order to obtain, by homologous recombination, a recombinant of PRV(BUK-dl 3) which also contains a deletion in the PRV g92 gene, it was necessary to start with the intact DNA of a tk+ PRV strain, wherein the functional tk gene was inserted in the PRV g92 gene, and a hybrid plasmid containing a deletion in the g92 gene (see: FIG. 5). The progeny virus obtained following this type of cross mainly comprise parental tk+ PRV. In order to enrich for tk− PRV recombinants in the harvest, selective media containing IdUrd was employed. IdUrd inhibits tk+ PRV replication and favors the outgrowth of tk− PRV. Other selective agents, such as BdUrd and 1-β-D arabinosylthymine, could be employed without departing from the spirit and scope of this invention.

The hybrid plasmid chosen for the construction of the above-described recombinant was pBUK:gCdlSal. However, other hybrid plasmids containing larger or smaller flanking sequences adjacent to the coding sequence of the PRV g92 gene, or larger or smaller deletions in other portions of the g92 gene, could be employed to create additional deletion mutants, without departing from the scope and spirit of this invention. Table 2 above shows some of the restriction nuclease cleavage sites which could be chosen for constructing such deletion mutants.

The tk+ PRV DNA chosen for the recombination step was PRV(dltk):PRVTK/STUl2. As discussed above, this strain contains a deletion in the PRV tk gene at the normal tk gene locus, and a second, fully functional PRV tk gene inserted into a deletion in the PRV g92 gene (see: FIG. 5). Homologous recombination by crossing the tk+ PRV(dltk):PRVTK/STUl2 with pBUK:gCdlSal results in the removal of the functional PRV tk gene and its replacement with a deletion only in the g92 gene.

The construction of the recombinant tk− PRV with a deletion in the g92 gene was carried out as follows:

RAB-9 cells were seeded in 60 mM Petri dishes (0.2×$10^6$ cells/dish) and incubated at 37° C. for 48 hr. Then, the following sterile solutions were added to a test tube in sequential order:

(1) 0.02 ml of a 50 μg/ml solution of the tk+ PRV(dltk):PRVTK/STUl2 in TE buffer;

(2) 0.2 ml of a 10 μg/ml solution of PstI-digested plasmid pBUK:gCdlSal. The PstI-digested plasmid was obtained by dissolving 10 μg of pBUK:gCdlSal in 500 μl of PstI cutting buffer and then digesting the plasmid for 1 hr at 37° C. with 20 units of PstI and then incubating the reaction mixture for one hr at 37° C. with proteinase k (EM Science) at 100 μg/ml. The reaction mixture was vortexed with an equal volume of phenol, centrifuged for phase separation, and dialyzed against 0.1×TE buffer;

(3) 0.65 ml of water;

(4) 1.0 ml of 20 μg/ml solution of salmon sperm DNA in 2× a HEPES buffer solution comprising 8.0 g/l NaCl, 0.37 g/l KCl, 0.125 g/l $Na_2HPO_4.2H_2O$, 1.0 g/l glucose, 5.0 g/l HEPES, pH 7.05; and (5) 0.13 ml of 2.0M $CaCl_2$.

The resulting solution was mixed by inversion and kept at room temperature for 30 min while a DNA-calcium phosphate precipitate formed. Then, 0.5 ml of the suspension containing a calcium phosphate precipitate of DNA was added directly to 5.0 ml of growth medium and plated on RAB-9 cells which had been seeded in 60 mm Petri dishes 48 hr earlier. The cells were incubated at 37° C. for 5 hr. Then, the media was aspirated, and the monolayer rinsed with 5.0 ml of fresh growth media, followed by the addition of 1.0 ml of a solution of a 1×HEPES buffer solution plus 15% (v/v) glycerol. After a 3-min incubation at room temperature, the solution was aspirated, the monolayer rinsed with media again, and fresh growth media added. The culture was incubated at 34.5° C. for 2 days until extensive cytopathic effects occurred. Virus harvests were made as described above and stored at −80° C. The virus harvest was then titrated in RAB-9 cells under an agar overlay.

The virus harvest from the cotransfection was thawed, sonicated, and diluted in growth media supplemented with 100 μg/ml IdUrd. In order to enrich for the tk− PRV recombinants, the harvested virus was diluted to give an input multiplicity of 0.1 PFU/cell and passaged in subconfluent monolayer cultures of RAB(BU) cells in 8-oz prescription bottles in growth medium supplemented with 100 μg/ml IdUrd. After a 1 hr absorption at 37° C., the infected monolayer cultures were washed three times with GKN. Then, growth medium containing 100 μg/ml IdUrd was added, incubation was continued at 34.5° C. for 48 hr, and virus harvests were made. The harvest of the selection step was titrated in RAB-9 cells, candidate recombinant tk− PRV were picked at random from plaques, and virus pools were prepared. In this manner, 96 tk− g92− PRV candidate recombinants were obtained.

M. Identification of Recombinant tk− g92− PRV Mutants with Deletions in Both the tk Gene and the g92 Gene Viral DNAs prepared from the candidate recombinants described above were analyzed by the dot-blot method, as described above, in order to identify recombinants that lacked both the 1.1 Kbp SalI sequence of the PRV g92 gene, and the approximately 150 bp SacI-C sequence of the PRV tk gene (see: U.S. Pat. No. 4,514,497)). Crude extracts of viral DNA from the 96 candidate recombinants were prepared from lysed cells and absorbed by filtration on nitrocellulose sheets. After drying, heating to fix the DNA to the filters, and pretreatment with modified Denhardt's solution, as described above, the filters were placed in hybridization buffer containing the $^{32}$P-labeled pSal probe discussed above. After hybridization and washing of the filters, the nitrocellulose filters were dried and exposed to X-ray film. About one-third of the candidate recombinants failed to hybridize to the probe, indicating that the sequences present in the 1.1 Kbp SalI fragment of pSal, which contains the majority of the g92 gene, were absent from these recombinant viruses. Clone 2 was selected at random and designated PRV(dlg92/dltk). This virus has been deposited with the American Type Culture Collection under ATCC No. VR-2116.

Viral DNA of high purity was prepared, digested with KpnI and BamHI, and the fragments were then separated by electrophoresis on agarose gels as described above. The ethidium bromide stained gels revealed that the KpnI-A fragment had been replaced by a fragment about 5 Kbp larger (see: FIG. 6A, lanes 10–13), and that the hypermolar band of the tk+ PRV(dltk):PRVTK/STUl2 (see: FIG. 6A, lane 14) which comigrated with KpnI-G/H of 8.6 Kbp was no longer present. The 19.2 Kbp BamHI-2 fragment of the tk+ PRV(dltk):PRVTK/STUl2 (see: FIG. 6A, lane 6) was absent in the recombinants and was replaced by a hypermolar band comigrating with the BamHI-3 fragment (16.7 Kbp) (see: FIG. 6A, lanes 2–5). Also, the BamHI-9 fragment which had disappeared in the tk+ PRV(dltk):PRVTK/STUl2 had again reappeared. These results are consistent with the deletion of a 1.1 Kbp SalI fragment from the PRV g92 gene which has replaced the functional PRV tk gene inserted in the deleted fragment of the PRV g92 gene of the tk+ PRV(dltk):PRVTK/STUl2 (see: FIG. 5).

After electrophoresis, Southern blots of the above gels were hybridized, as discussed above, to the (i) $^{32}$P-labeled oligo-006, (ii) $^{32}$P-labeled pBUK:Stul2/PstI, and (iii) $^{32}$P-labeled pSalI probes described above, except that the hybridization buffer for the oligo-006 probe was 35% (v/v) formamide, 0.6M NaCl, 0.2M Tris-HCl, pH 8.0, 0.02M EDTA, 0.1% (w/v) sodium dodecylsulfate, 50 μg/ml alkaline-denatured salmon sperm DNA, and 10 μg ml poly(A), and the final wash was in 6×SSC.

The following results were obtained from these autoradiographic experiments:

(1) The oligo-006 probe hybridized to the KpnI-$J_L$ and the BamHI-11 fragments of PRV(BUK-5A-Rl) (see: U.S. Pat. No. 4,514,497) and to the 8.6 Kbp KpnI and the 19.2 Kbp BamHI fragments of PRV(dltk):PRVTK/STUl2, both which contain intact functional tk genes, but not to the tk− deletion mutants, PRV(BUK-dl 3) and PRV(dlg92/dltk). This demonstrates that the candidate recombinants, designated PRV(dlg92/dltk) (Clones 2, 3, 8, and 10) lacked the same approximately 150 bp sequence of the PRV tk gene that had previously been deleted from PRV(BUK-dl 3).

Figure 6B:
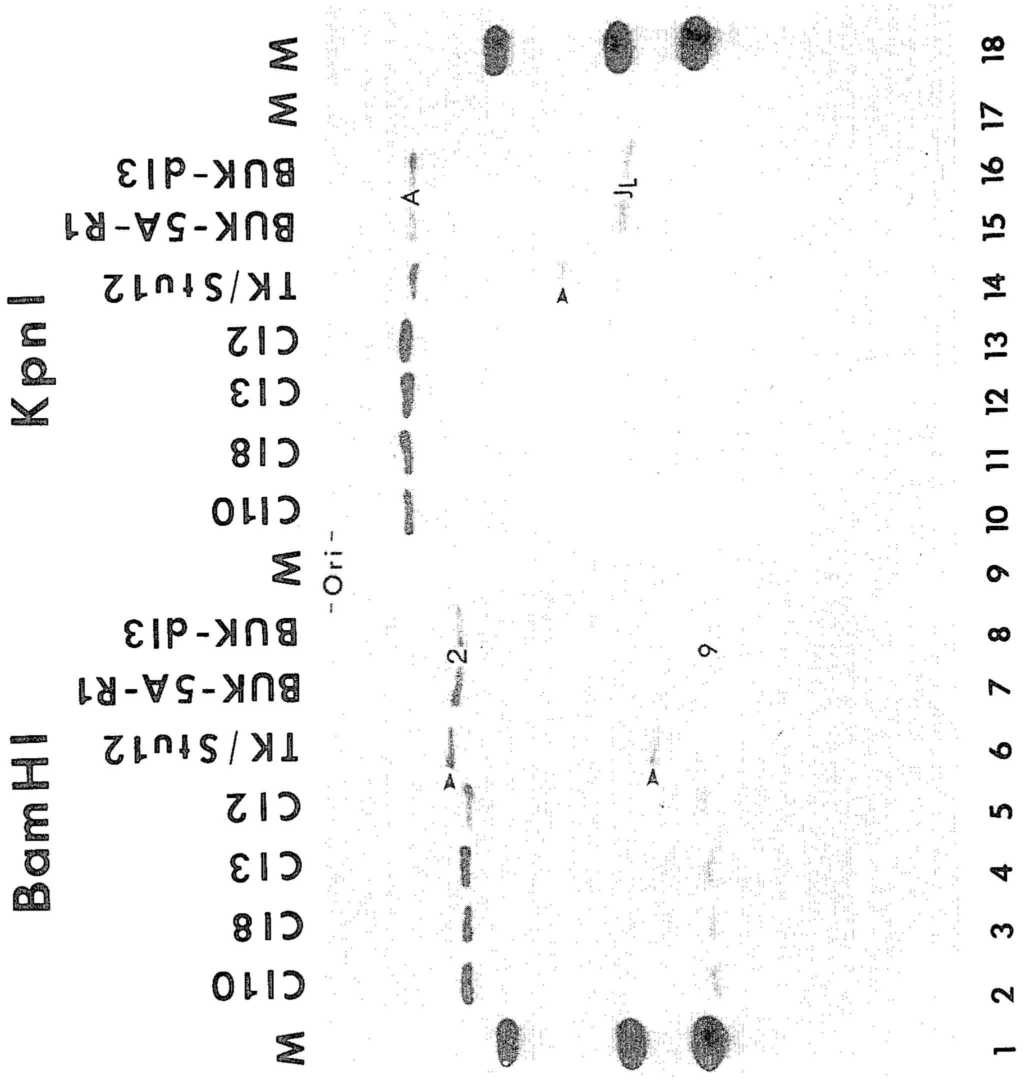
FIG. 6B shows autoradiographs demonstrating molecular hybridization of the $^{32}$P-labeled pBUK:Stu12/PstI probe to the DNA fragments of the PRV strains shown in FIG. 6A.

(2) The $^{32}$P-pBUK:Stul2/PstI probe hybridized to the BamHI-2, the BamHI-9, the KpnI-$J_L$, and the KpnI-A fragments of PRV(BUK-5A-Rl) and PRV(BUK-dl 3), as expected (see: FIG. 6B). This probe did not hybridize to the original KpnI-$J_L$ or KpnI-A fragments of the recombinant PRV(dlg92/dltk) viruses, but instead, hybridized to a new fragment, 34.2 Kbp, which results from the fusion of the KpnI-A and the KpnI-$J_L$ (deleted) fragments (see: FIG. 5 and FIG. 6B). Likewise, the pBUK:Stul2/PstI probe hybridized to a new 16.7 Kbp BamHI-2 fragment, which resulted from the deletion of the 1.1 Kbp SalI sequence from the parental BamHI-2 (See FIG. 6B).

Figure 6C:
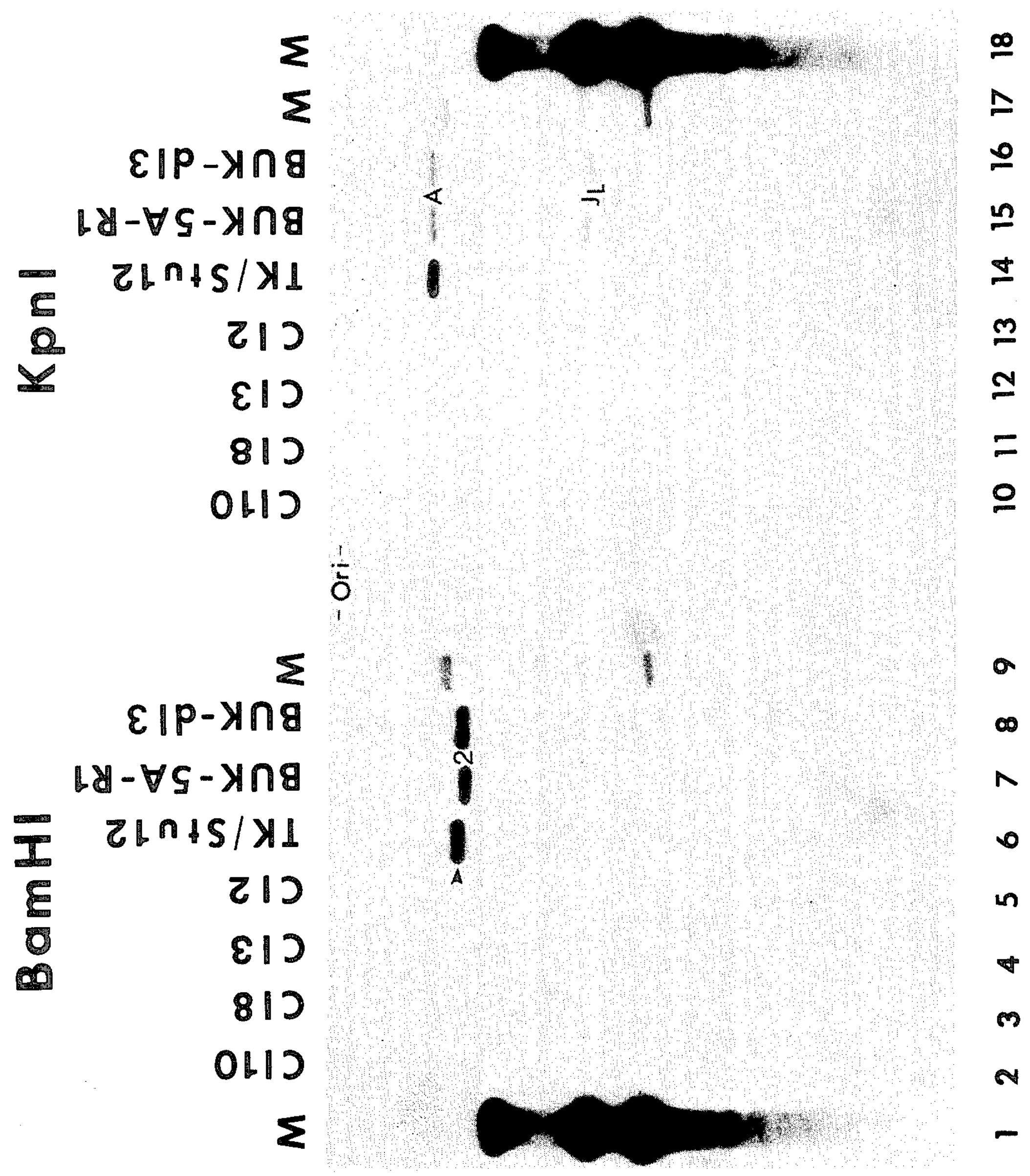
FIG. 6C shows autoradiographs demonstrating molecular hybridization of the $^{32}$P-labeled pSal probe to specific DNA fragments of the PRV strains shown in FIG. 6A.

(3) The $^{32}$P-pSal probe hybridized only to the BamHI-2, KpnI-$J_L$, and KpnI-A fragments of PRV(BUK-5A-Rl), PRV(BUK-dl 3), and the NOVEL 34.2 Kbp KpnI and 19.2 Kbp BamHI fragments of PRV(dltk):PRVTK/STUl2 (see: FIG. 5 and FIG. 6C). However, this probe did not hybridize at all to the fragments of the candidate recombinant PRV(dlg92/dltk) viruses (see: FIG. 6C).

The preceding results demonstrate that the PRV(dlg92/dltk) recombinant viruses were double mutants, with an approximately 150 bp deletion in the PRV tk gene and an approximately 1.1 Kbp deletion in the PRV g92 gene.

EXAMPLE 2

TK Activity Of PRV Strains

In order to analyze the phenotypes of the PRV g92 deletion and/or insertion mutants, i.e., PRV(dlg92/dltk) and PRV(dltk):PRVTK/STUl2 (see: FIG. 5), autoradiography of infected cells was performed as follows:

RAB(BU) cells were seeded (50,000 cells/well) into an 8-well Lab-Tek™ (Miles Laboratories, Inc.) slide and incubated for 1–2 days at 37° C. until confluent. The cells were infected at about 10 PFU/cell with the parental virus strains PRV(BUK-5) and PRV(BUK-dl 3) or with the recombinant viruses, PRV(dltk):PRVTK/STUl2 and PRV(dlg92/dltk). After a 1-hr absorption at 37° C., fresh growth media was added. At 3 hr post-infection, the growth media was changed to fresh growth medium with 5.0 μCi $^{3}$H-dThd/ml, 0.1 μg/ml dThd. At 20 hr post-infection, the medium was aspirated and the cells were rinsed with 1X GKN, methanol, and then fixed in methanol for 1 min at room temperature. The wells and gasket were removed from the slide and the cells were washed at 4° C. for 5 min each with 5.0% (w/v) trichloroacetic acid (twice), 70% (v/v) ethanol (3 times), and 100% ethanol (twice). After drying in air, the slides were stained in 2.0% (w/v) acetic-orcein for 2 min, then destained in ethanol. The slides were dipped in autoradiographic photographic emulsion (Kodak-NTB2) at 40° C. and dried in a horizontal position for 1 hr. Then, the slides were placed in a darkened box with drierite and left at room temperature for 20 hr. The slides were developed in Kodak Dektol for 2 min at 16° C., rinsed in water for 10 sec, fixed in Kodak fixer for 5 min, and rinsed in water 2 times, each for 2.5 min.

In all cells infected with PRV(BUK-5), i.e., a tk+ PRV, the nuclei were heavily labeled due to the phosphorylation of $^3$H-dThd by the PRV TK enzyme, and the subsequent incorporation of the $^3$H-dTTP into acid insoluble nuclear DNA. Similarly, in all cells infected with PRV(dltk):PRVTK/STU12, the nuclei were heavily labeled with $^3$H-dThd which demonstrates that a functional PRV tk gene was inserted into the PRV g92 gene. This result was expected since this recombinant virus was selected with HATG medium. As expected, PRV(BUK-dl 3) and PRV(dlg92/dltk) produced pronounced cytopathic effects in the infected cells due to virus growth, but the nuclei of the cells infected with these viruses were not labeled because of the absence of a functional TK enzyme with which to phosphorylate the $^3$H-dThd. Thus, these experiments demonstrate that PRV(dlg92/dltk) was a tk− PRV and that PRV(dltk):PRVTK/STU12 was a tk+ PRV.

In addition to the autoradiographic experiments described above, cytosol extracts from PRV-infected cells were assayed for $^3$H-dThd-phosphorylating activity to verify that PRV(dlg92/dltk) lacked TK-inducing activity. These experiments were carried out as describd above (see: U.S. Pat. No. 4,514,497, and Kit, S., Kit, M., and Pirtle, E. C., *Am. J. Vet. Res.* 46: 1350–1367 (1985)). The results are shown in Table 3 below:

TABLE 3

THYMIDINE KINASE (TK) ACTIVITY OF RAB(BU) CELLS INFECTED FOR 6.5 HR WITH tk+ PRV AND tk− PRV VIRUSES

| PRV strain used to infect RAB(BU) cells | TK activity[a] |
|---|---|
| Mock-infected RAB(BU) | 0.05 |
| PRV(BUK-5) | 2.40 |
| PRV(dlg92/dltk) | 0.05 |

[a]picomoles $^3$H-dTMP formed from $^3$H-dThd in 10 min at 38° C. per μg protein.

Table 3 above shows that: (1) mock-infected RAB(BU) cells, i.e., tk− cells, have negligible TK activity; (ii) TK activity is acquired by RAB(BU) cells after infection with the tk+ virus, PRV(BUK-5); but (iii) TK activity is not acquired after infection by the mutant virus, PRV(dlg92/dltk). Thus, like PRV(BUK-dl 3), the PRV(dlg92/dltk) virus is a tk− PRV.

EXAMPLE 3

Temperature Resistance of PRV Strains

Replicate, subconfluent monolayer cultures of RAB-9 cells were infected with PRV(BUK-dl 3) or PRV(dlg92/dltk) at an input multiplicity of about 0.1 PFU/cell and incubated in a $CO_2$-incubator at 30° C., 34.5° C. and 39.1° C. Virus harvests were prepared at 5 hr after infection at 34.5° C. to determine the amount of infectious virus present immediately after the absorption and penetration of the virus strains. Virus harvests were also made at 43–54 hr after the cells were infected with the viruses at 34.5° C. and 39.1° C. and at 91–115 hr after the cells were infected with the viruses at 30° C. (see: Table 4). Extensive cytopathic effects were observed at the harvest times. The virus harvests were then plaque titrated at 34.5° C. and at 39.1° C. in RAB-9 cells as described in U.S. Pat. No. 4,514,497. The results are shown in Table 4 below.

TABLE 4

REPLICATION OF tk− PRV STRAINS

| Virus | Temperature of virus growth | Time postinfection harvested (hr) | Virus yield (PFU/ml) when plaque titrated at 34.5° C. | 39.1° C. |
|---|---|---|---|---|
| PRV(BUK-dl 3) | 34.5° C. | 5 | $2.0 \times 10^3$ | $1.5 \times 10^3$ |
| | 34.5° C. | 43 | $6.0 \times 10^8$ | $6.1 \times 10^8$ |
| | 39.1° C. | 43 | $2.7 \times 10^8$ | $2.8 \times 10^8$ |
| | 30° C. | 91 | $7.8 \times 10^7$ | $7.0 \times 10^7$ |
| PRV(dlg92/dltk) | 34.5° C. | 5 | $3.0 \times 10^2$ | $4.0 \times 10^2$ |
| | 34.5° C. | 54 | $1.3 \times 10^8$ | $1.3 \times 10^8$ |
| | 39.1° C. | 52 | $2.5 \times 10^7$ | $2.4 \times 10^7$ |
| | 30° C. | 115 | $5.9 \times 10^6$ | $5.7 \times 10^6$ |

Table 4 above demonstrates that PRV(BUK-dl 3) replicated to about the same titer at 39.1° C. as at 34.5° C. (about $3\times10^8$ and $6\times10^8$ PFU/ml, respectively). Harvests prepared at 91 hr postinfection from the 30° C. incubations had a titer of about $8\times10^7$ PFU/ml, demonstrating that efficient virus replication also occurred at 30° C. Significantly, these titers were observed regardless of whether the plaque titrations to assay for virus yields were performed at 34.5° C. or at 39.1° C.

Table 4 shows that PRV(dlg92/dltk) replicated more slowly then PRV(BUK-dl 3) and that the titers obtained after infection of cells by PRV(dlg92/dltk) were somewhat lower than those obtained after infection of cells by PRV(BUK-dl 3). However, efficient replication by PRV(dlg92/dltk) was observed at 30° C., 34.5° C., and 39.1° C. Likewise, plaque titration assays of the virus harvests demonstrated that about the same titers were measured regardless of whether the plaque titration was performed at 34.5° C. or 39.1° C. These results clearly demonstrate that both PRV(BUK-dl 3) and PRV(dlg92/dltk) are temperature-resistant and can replicate efficiently over a broad range of temperatures, specifically from 30° C. to 39.1° C. or higher.

EXAMPLE 4

Specific Antibody Production And Protection Study In Swine Vaccinated With PRV(dlg92/dltk)

In order to analyze the PRV-specific glycoproteins made in cells infected with PRV(dlg92/dltk), and to compare these glycoproteins with the glycoproteins made in cells infected with other PRV strains, it was necessary to obtain PRV(dlg92/dltk)-specific antisera (hereinafter "Type C antisera). This was accomplished by immunizing pigs, WP2 and BP2, with PRV(dlg92/dltk) as descibed in detail below. Subsequently, these two immunized pigs were challenge-exposed to virulent PRV(Ind-F), and postchallenge antisera (hereinafter "Type D antisera") was collected as described in detail below. In this way, it was possible to obtain antibodies induced only by PRV(dlg92/dltk) proteins and, also, those additional antibodies, i.e., anti-g92 antibodies, induced by virulent PRV strains, but not by PRV(dlg92/dltk). Furthermore, this pilot study permitted an evaluation of the safety and efficacy of the PRV(dlg92/dltk) vaccine virus.

The Type C antisera was produced from pig WP2, i.e., a 6-week-old castrated male, and from pig BP2, i.e., a female pig. The two pigs were Yorkshire X Duroc X Landrace X Hampshire crosses, each weighing 11.4 Kg, and were housed in a climate-controlled environment in separate rooms. Nipple waterers provided free-choice water, and a 16% commercial swine feed was provided in self-feeders daily. The prevaccination antisera for pigs WP2 and BP2 were negative for anti-PRV neutralizing antibodies.

On day one, both pigs were inoculated in the neck muscle with 2.0 ml ($4\times10^8$ PFU/ml) of PRV(dlg92/dltk). The appetite of the pigs did not decrease and no adverse reactions were observed during the post-vaccination period.

Twenty days later, both pigs were again vaccinated in the neck muscle with the same dose of PRV(dlg92/dltk) and a second serum sample was obtained. The PRV neutralization titer was 1:4 at this time. The appetite of the pigs did not decrease and no adverse reactions were observed during the second post-vaccination period. Fourteen days later, serum samples were again obtained and this latter sera was designated at Type C antisera.

At the same time Type C antisera was collected, both pigs were challenge-exposed intramuscularly in the neck muscle to about $3\times10^8$PFU of the virulent Ind-F strain of PRV. Sixteen days later, serum saamples were obtained and designated as Type D antisera. No adverse reactions were noted during the 51-day course of this experiment. The female pig and the castrated male weighed 41.4 Kg and 34.6 Kg, respectively, at that end of the experiment. Weight gain had occurred at a normal rate for commercially raised pigs and both pigs remained vigorous and healthy.

Thus, PRV(dlg92/dltk) retained the previously proven protective properties of PRV(BUK-dl 3) (see: Kit, S., Kit, M., Pirtle, E. C., *Am. J. Vet. Res.* 46: 1359–1367 (1985); Kit, S., Kit, M., Lawhorn, B., and McConnell, S., In: *High-Technology Route to Virus Vaccines* Eds. Dreesman, G. R., Bronson, J. G. and Kennedy R. C. (American Society for Micrology, Washington, D.C.). pp. 82–99 (1985)), despite the deletion in the PRV g92 gene.

EXAMPLE 5

Analyses Of Mannose-Labeled Glycoproteins Synthesized In PRV-Infected Cells

(A) Immunoprecipitation of mannose-labled glycoproteins from cell extracts

Several types of PRV antisera were employed in these experiments: (i) Type A antisera from pigs vaccinated with PRV(BUK-dl 3); (ii) Type B antisera from pigs vaccinated with PRV(BUK-dl 3) and subsequently challenge-exposed to the highly virulent Ind-F strain of PRV; (iii) Type C antisera from pigs vaccinated with PRV(dlg92/dltk); (iv) Type D antisera from pigs vaccinated with PRV(dlg92/dltk) and subsequently challenge-exposed to the highly virulent Ind-F strain of PRV; (v) Type E antisera from domestic pigs naturally infected with PRV; (vi) Type F antisera from feral pigs naturally infected with PRV; and (vii) Type G antisera comprising PRV monoclonal antibodies, derived from mouse hybridoma cells, which react with PRV gp82.

Types B, D, E, and F antisera react with all of the principal glycoproteins of tk+ PFV field strains. Type A antisera reacts with all of the principal glycoproteins of tk+ PRV field strains except for gI (see: Mettenleiter, T. C., Lukacs, N. and Rziha, H. J., *J. Virol.* 53: 52–57 (1985)). This is because, as discussed above, PRV(BUK-dl 3) is derived from the Bucharest strain which does not produce gI. Type C antisera reacts with all of the principal PRV glycoproteins, except gI and g92. This is because, as discussed above, PRV(dlg92/dltk) is derived from PRV(BUK-dl 3) which does not produce gI, and PRV(dlg92/dltk) does not produce g92 because of the engineered deletion in the PRV g92 gene. Hence, Type C antisera was useful to differentiate PRV(dlg92/dltk)-vaccinated pigs from pigs vaccinated with other Bucharest strains, e.g., PRV(BUK-5), PRV(BUK-dl 3), or PRV(Norden) as described in detail below.

Types A and B antisera were produced from pigs Nos. 103 and 106, respectively, i.e., 6-week-old pigs. The pigs were Landrace X Hampshire X Yorkshire crosses which are housed in a climate-controlled environment in separate rooms. The prevaccination antisera from pigs Nos. 103 and 106 were negative for anti-PRV neutralizing antibodies.

On day one, pig No. 103 was inoculated in the gluteal muscle with 1.25 ml ($4\times10^8$ PFU/ml) of PRV(BUK-dl 3). Thirteen days later, pig. No. 103 was again vaccinated in the gluteal muscle with 1.5 ml of the same viral preparation and pig No. 106 was vaccinated for the first time with 1.5 ml of the same viral preparation. The PRV neutralization titer for pig No. 103 was 1:4 at this time. Fourteen days later, i.e., 27 days afer the first vaccination, pig No. 103 was bled to obtain Type A antisera. The PRV neutralization titer at this time was 1:64. On the same day, pig No. 106 was challenge-exposed intranasally with about $7\times10^8$ PFU/ml of the virulent Ind-F strain of PRV. Ten days after the challenge-exposure of pig No. 106 to the virulent Ind-F strain of PRV, serum samples were obtained from pig No. 106 and designated Type B antisera. The PRV neutralization titer was 1: 256 (see: Kit, S., Kit, M. and Pirtle, E. C., *Am. J. Vet. Res.* 46: 1359–1367 (1985)).

Types C and D antisera were derived as described above.

Type E antisera were obtained from E. C. Pirtle, Virologinal Research Laboratory, National Animal Disease Center, Ames, Iowa.

Antisera Nos. 6-1, 3-35 and 5-29 were obtained from individual pigs at a packing plant in Iowa. These antisera were positive for PRV antibodies as determined by microimmunodiffusion tests (MIDT) (see: Gutekunst, D. E., Pirtle, E. C. and Mengeling, W. L., *Am. J. Vet. Res.* 39: 207–210 (1978) for MIDT procedures). Approximately 10% of the pigs slaughtered at the packing plant were seropositive for PRV, and, hence, had previously been naturally infected with PRV. The virus-neutralizing antibody titers of these sera were not determined.

Type F antisera was provided by Dr. Robert A. Crandell, Texas Veterinary Medical Diagnostic Laboratory, College Station, Tex. This antisera was obtained by bleeding Piney Wood rooter pigs that were being sold at an East Texas auction market. The bleeding was performed to determine the incidence of PRV antibodies, and, hence, PRV natural infection in the feral pigs of this region (see: Kit, S., Kit, M., Lawhorn, B. and McConnell, S., In: *High-Technology Route to Virus Vaccines,* Eds. Dreesman, G. R., Bronson, J. G. and Kennedy, R. C. (American Society for Microbiology, Washington, D.C.) pp. 82–99 (1985)). Antisera from six different feral pigs with virus neutralization titers ranging from 1:4 to 1:64 were analyzed.

Type G antisera was provided by Dr. R. A. van Deusen, Biologics Virology Laboratory, National Veterinary Services Laboratory, United States Department of Agriculture, Ames, Iowa. The antisera was anti PRV gp82-2 monoclonal antibody clone 3G9-F2 (mouse IgM) produced against PRV(IND-F) (see: Wathen, L. M. K., Platt, K. B., Wathen, M. W., van Deusen, R. A., Whetstone, C. A. and Pirtle, E. C., *Virus Research* 4: 19–29 (1985)).

To obtain the PRV-specific glycoproteins made in cells infected with attenuated vaccine or virulent PRV strains, confluent cultures of RAB-9 cells in 4-oz prescription bottles were infected with various PRV strains at an input multiplicity of about 20 PFU/cell. The viruses were absorbed for 1 hr at 37° C. with gentle agitation every 15 min. Then, 5.0 ml growth medium supplemented with 2.0% (w/v) dialyzed (against PBS buffer) fetal calf serum was added. The use of dialyzed fetal calf serum at the lowered concentration of 2.0% (w/v) rather than 10% (w/v) facilitates the incorporation of labelled precursors, such as $^{35}$S-methonine and $^{3}$H-mannose or $^{3}$H-glucosamine, into viral-specific proteins and glycoproteins and reduces the dilution of the radioactive metabolites by endogenous non-labelled metabolites. The PRV-infected cells were incubated at 34.5° C. until 5 hr post-infection. To label the cells, the medium was removed, the cell monolayers were washed with glucose-free medium, and 5.0 ml of glucose-free, growth medium containing 100 μCi of $^{3}$H-mannose (Amersham Corporation) was added. The cells were reincubated at 34.5° C. until 24 hr post-infection, at which time the media were removed by aspiration, the cells were washed with GKN, and then 0.4 ml of Nonidet P40-extraction buffer comprising 1.0% (w/v) NP40 (nonionic detergent), 0.9% (w/v) NaCl, 0.0625M Tris-HCl, pH 7.0, was added with gentle swirling for 5 min. The cells were then frozen at −80° C., thawed, and disrupted by sonication. The protein extracts were stored at −80° C.

For immunoprecipitation, 70 μl of each extract was added to 30 μl of Type A, B, C, D, E or F antisera and then the mixture was incubated at 4° C. for 16–20 hr. Then, 150 μl of Pansorbin (protein A; Calbiochem) was added to absorb the antigen-antibody complexes, and the mixture was incubated at 4° C. for 45 min. After centrifugation at 9,000 rpm for 10 min in an SS34 rotor of a Sorvall centrifuge, the supernatant was removed, and the pellet was resuspended in wash buffer comprising PBS plus 0.05% (v/v) of Tween 20. The centrifugation and washing of the pellet were repeated 3 times and, finally, the pellet was suspended in 60 μl of distilled water. Thirty μl of buffer D comprising 0.0625M Tris-HCl, pH 6.8, 0.3% (w/v) sodium dodecyl sulfate, 0.5% (v/v) 2-mercaptoethanol, 10% (v/v) glycerol, and 0.001% (w/v) bromophenol blue, was added, and the mixture was boiled for 2 min and stoed at −80° C. until used.

In the case of the immunoprecipitation with monoclonal antibody gp82-2, 90 μl of each extract was added to 10 μl of Type G antisera (IgM) and the mixture was incubated at 4° C. for 20 hr. Then, 30 μl of a 1.0 mg/ml solution of antimouse polyclonal sera in 50% (v/v) glycerol (Kirkegaard and Perry Laboratories Inc.) was added and the incubation was continued at 4° C. for another 20 hr. Then, 165 μl of Pansorbin (protein A) was added. The remainder of the procedure was the same as that described above.

The samples were next analyzed by electrophoresis on SDS-polyacrylamide gels under denaturing conditions as described below.

(1) 5× electrophoresis buffer comprising:
  (a) 144 g glycine (Calbiochem);
  (b) 30 g Trizma (Sigma Chemical Co.); and
  (c) 5.0 g sodium dodecyl sulfate.

(2) 3.0% (w/v) polyacrylamide stacking gel comprising:
  (a) 3.17 ml $H_2O$;
  (b) 1.25 ml upper Tris buffer (4×0.5M Tris-HCl, pH 6.8, 0.4% (w/v) sodium dodecyl sulfate);
  (c) 0.5 ml acrylamide:bisacrylamide (30:0.8 w/w);
  (d) 75 μl 2.0% (w/v) ammonium persulfate (BioRad Labs); and
  (e) 5.0 μl TEMED (Sigma Chemical Co.).

(3) 10% (w/v) polyacrylamide running gel comprising:
  (a) 12 ml $H_2O$;
  (b) 7.5 ml lower Tris buffer (4×1.5M Tris-HCl, pH 8.8+0.4% (w/v) sodium dodecyl sulfate);
  (c) 10 ml acrylamide:bisacrylamide (30:0.8 w/w);
  (d) 0.6 ml 2% (w/v) ammonium persulfate;
  (e) 15 μl TEMED; and
  (f) 0.5 ml 50% (v/v) glycerol.

The $^{3}$H-mannose-labeled samples in 100 μl of buffer D were applied to 1.5 mm thick Laemmli gels and electrophoresed at 40 volts at constant voltage, for 16 hr at room temperature (see: Laemmli, U. K., *Nature* 227:680–685 (1970)). The gels were fixed and stained for 30 min at room temperature with a solution comprising 50% (v/v) methanol, 10% (w/v) acetic acid, and 0.015% (w/v) coomassie blue, then destained for 2 hr at room temperature with a solution comprising 10% (v/v) acetic and 10% (v/v) methanol. The gel was then treated with En$^{3}$Hance™ (New England Nuclear Products) for 1 hr at room temperature and washed with distilled water for 30 min. The gel was next dried and subjected to direct autoradiography with Fuji X-ray film and a lighting plus intensifying screen (Cronex screen; E. I. DuPont de Nemours and Co., Inc.) at −70° C. for 1–5 days.

Figure 7A:
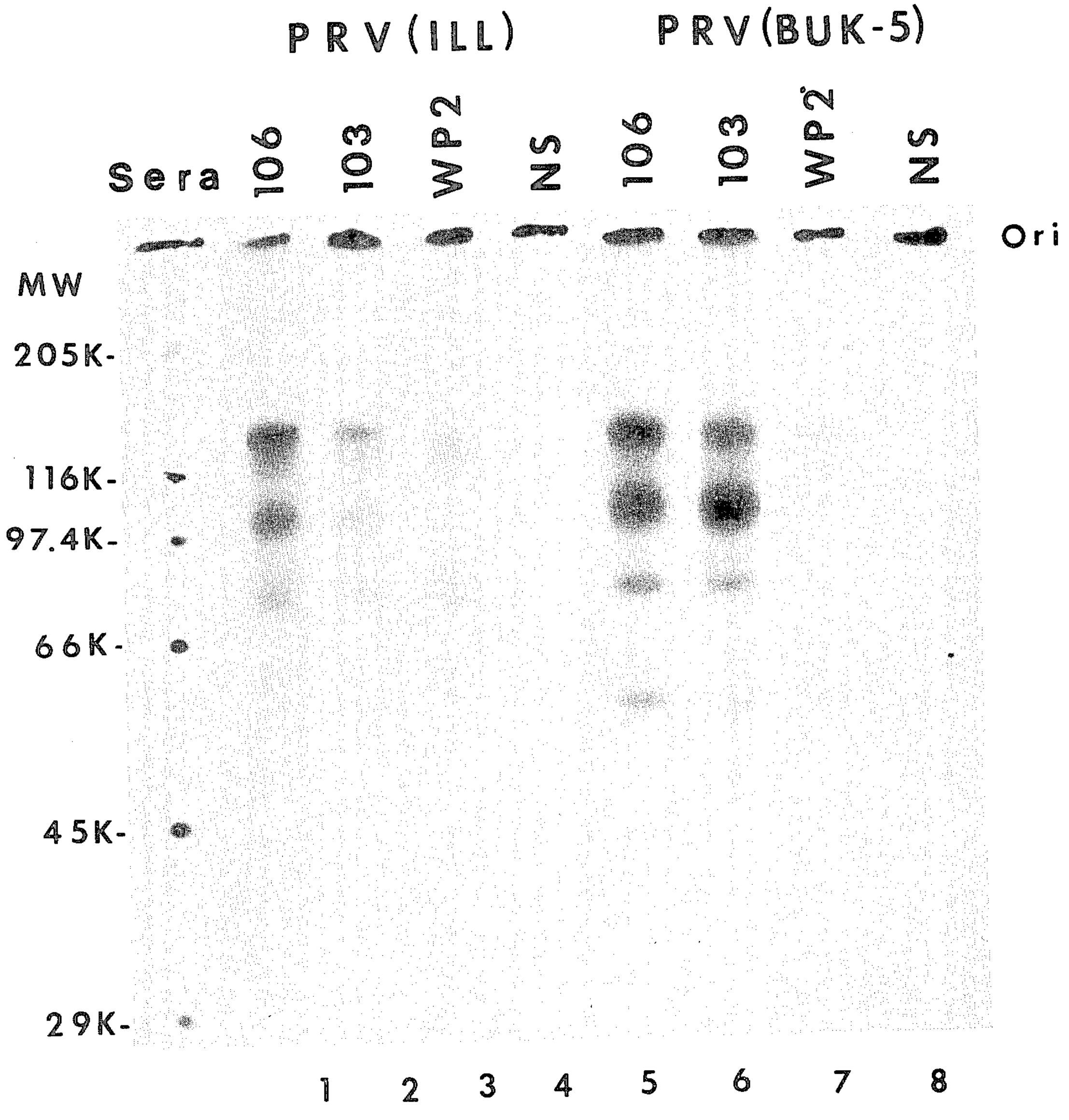
FIGS. 7A and 7B show $^{3}$H-mannose-labeled proteins from PRV-infected RAB-9 cells after immunoprecipitation with different PRV-specific antisera, electrophoresis on SDS-polyacrylamide (7.5%) gels, and autoradiography. Cultures were infected at an input multiplicity of about 20 PFU/cell and labeled with $^{3}$H-mannose at 34.5° C. in glucose-free medium from 5-24 hr after infection. PRV strains utilized for infection were the virulent Illinois strain, tk+ PRV(I11) (FIG. 7A, lanes 1-4), the parental tk+ PRV(BUK-5) (FIG. 7A, lanes 5-8), the tk$^-$ deletion mutant, PRV(BUK-dl 3) (FIG. 7B, lanes 9-12), and the recombinant tk$^-$ g92$^-$ deletion mutant, PRV(dlg92/dltk) (FIG. 7B, lanes 13-16). Type A antisera was from pig No. 103 which had been vaccinated twice with PRV(BUK-dl 3), but not challenge-exposed to virulent virus. Type B antisera was from pig No. 106 which had been vaccinated with the tk$^-$ PRV(BUK-dl 3), then challenge-exposed 14 days post-vaccination to the virulent tk+ PRV(Ind-F), and finally, bled 2 weeks after the challenge-exposure to the virulent virus to obtain post-challenge sera (see: Kit, S., Kit, M. and Pirtle, E. C., *Am. J. Vet. Res.* 46: 1359∝1367 (1985)). Type C antisera was obtained from pig WP2 which had been vaccinated with the tk$^-$ PRV(dlg92/dltk).
Figure 7B:
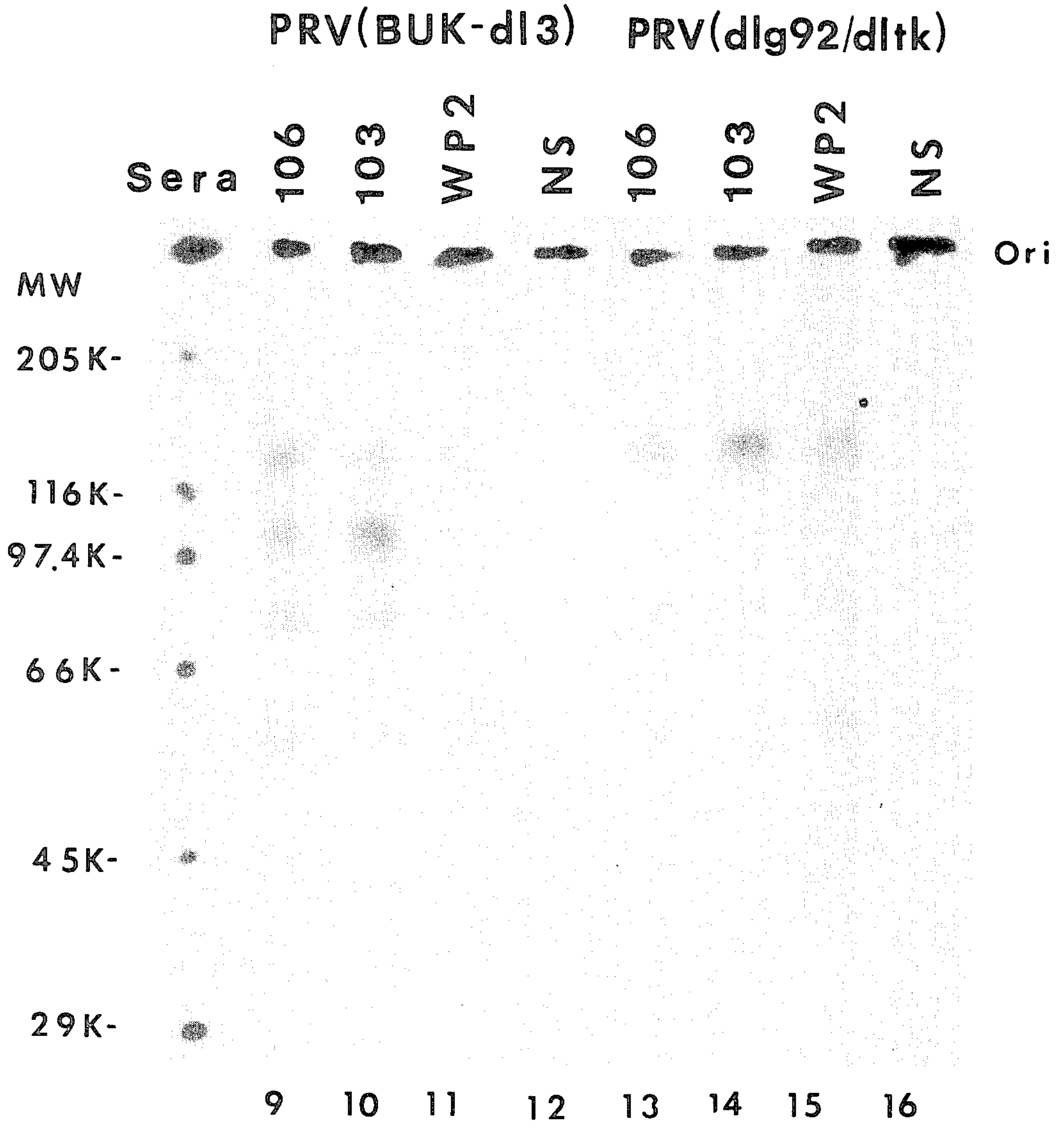

The following results were obtained:

(1) Normal (preblend) pig serum (NS) did not precipitate $^{3}$H-mannose-labeled glycoprotein from extracts of PRV-infected cells (see: FIGS. 7A and 7B).

(2) Type A, Type B, Type C, Type D, Type E and Type F antisera did not precipitate $^{3}$H-mannose-labeled glycoprotein from extracts of mock-infected cells (data not shown).

(3) Type B (see: FIG. 7A, lane 1), Type D, Type E and Type F antisera immunoprecipitated, from virulent tk+ PRV(I11)-infected cells, heavily $^{3}$H-mannose-labeled glycoproteins with apparent molecular weights of about 116,000 to 130,000 daltons (PRV gIIa and gI), 92,000 to 98,000 daltons (PRV gIII and gIV), 74,000 (PRV gIIb), 62,000 (PRV gV) and 58,000 daltons (PRV gIIc) and a lightly $^{3}$H-mannose-labeled glycoprotein with a molecular weight of about 40,000 daltons. These results are similar to those obtained by other investigators (see: Hampl, H., Ben-Porat, T., Ehrlicher, L, Habermehyl, K. O., and Kaplan, A. S., *J. Virol.* 52: 583–490 (1984); Lukacs, N., Thiel, H. J., Mettenleiter, T. C., and Rziha, H. J., *J. Virol.* 53: 166–173 (1985); and Robbins, A. K., Weis, J. H., Enquist, L. W., and Watson, R. J., *J. Mol. Appl. Genet.* 2: 485–496 (1984)).

(4) In the case of the extracts from PRV(BUK-5) and PRV(BUK-dl 3)-infected cells, Type B (see: FIG. 7A, lane 5 and FIG. 7B, lane 9) and Types D, E and F antisera precipitated similar $^{3}$H-mannose-labeled glycoproteins, except that the 116,000 to 130,000 molecular weight band presumably did not contain gI, since gI is absent from cells infected with Bucharest-derived strains of PRV because of the KpnI-I deletion.

(5) The glycoproteins from extracts of PRV(dlg92/dltk)-infected cells by Type B antisera (see: FIG. 7B, lane 13) and by Types D, E and F antisera, were similar to those precipitated from PRV(BUK-5)- and PRV(BUK-dl 3)-infected cells, but with the exception that the antisera failed to precipitate the 92,000 to 98,000 daltons glycoprotein, i.e., gIII. Further, Type B antisera did not precipitate the 92,000–98,000 daltons glycoprotein from mannose-labelled extracts of PRV(dltk):PRVTK/STU12-infected cells.

(6) The patterns of $^{3}$H-mannose-labeled proteins precipitated by Type A antisera, which was obtained from the tk− PRV(BUK-dl 3) vaccinated pigs, were generally similar to those observed with Type B, Type D, Type E and Type F antisera, expect that the labeling of the 116,000 to 130,000 molecular weight band was diminished in the immunoprecipitates from the tk+ PRV(Ill)-infected cells. This is the expected result since pigs vaccinated with PRV(BUK-dl 3) are deficient in the induction of antibodies to gI. It is also noteworthy that when extracts from PRV(Ill), which contain gI, were used for immunoprecipitation, the ratio of labelling of the gV (62,000) band relative to the gIIc (58,000) band was increased with all of the antisera (Compare FIG. 7A, lanes 1–3 with lanes 5–7 and FIG. 7B, lanes 9–11 with lanes 13–15). This is consistent with the observation that gI and gV are part of a noncovalent glycoprotein complex.

(7) Significantly, Type C antisera obtained from pigs vaccinated with the tk− PRV(dlg92/dltk) precipitated essentially none of the major 92,000 to 98,000 molecular weight glycoprotein (see: FIG. 7A, lanes 3 and 7 and FIG. 7B, lanes 11 and 15). However, Type D antisera obtained after challenge exposure of the previously vaccinated pigs with the tk+ PRV(Ind-F), did precipitate the major 92,000 to 98,000 molecular weight glycoprotein, as expected.

(8) Type G antisera precipitated only the major 92,000 to 98,000 molecular weight glycoprotein from extracts of PRV(Ill)-infected cells, but did not precipitate any glycoprotein from the extracts of PRV(dlg92/dltk)-infected cells.

The results clearly demonstrate that the tk− PRV(dlg92/dltk) was deficient in synthesizing the major 92,000 to 98,000 daltons glycoprotein which as demonstrated below, corresponds to gIII. Similarly, PRV(dltk):PRVTK/STU12 was deficient in synthesizing the major 92,000 to 98,000 daltons glycoprotein. Since these two strains were derived from the Bucharest strain of PRV, they were also deficient in synthesizing gI. Hence, pigs vaccinated with the tk− PRV(dlg92/dltk) failed to make antibodies against gIII and gI. Thus, antisera from pigs vaccinated with the tk− PRV(dlg92/dltk) can be distinguished from antisera of pigs infected with virulent tk+ PRV strains and from pigs vaccinated with those Bucharest, Bartha, and NIA-4 vaccine strains which express gIII.

(B) Immunoprecipitation of fractionated mannose-labeled glycoproteins

In order to isolate and study the individual glycoproteins (or glycoprotein complexes) made in PRV-infected cells, 9.6×10$^{6}$ RAB-9 cells were infected with about 30 PFU/cell of the tk+ PRV(Ill) strain and labelled from 5 to 24 hr after infection with $^{3}$H-mannose, as described above. Next, Nonidet P40 extracts were prepared as described above (total volume 1.6 ml). Then, 1.0 ml of extract was layered onto 10.2 ml of a continuous 5%–15% (w/v) sucrose gradient in PBS, and centrifuged at 4° C. for 20 hr at 32,000 rpm in a Beckman SW41 rotor of a Spinco ultracentrifuge. Twenty-nine fractions of about 0.4 ml each were collected from the bottom of the centrifuge tube. Twenty μl aliquots were spotted on 24 mm diameter Whatman GF/A disc filters, washed twice for 10 min each with 5% (w/v) trichloroacetic acid, once for 10 min with ethanol, dried at 80° C. for 30 min, and then counted in a liquid scintillation spectrometer to locate the $^{3}$H-mannose-labelled cellular and viral glycoproteins. A radioactive band skewed to the heavy side of the sucrose gradient was found in fractions 14 to 27. The peak of the radioactive band was located in fraction 23. It was anticipated that the noncovalent glycoprotein complex comprising gI, gIV, gV and p115, as well as the covalently bound complexes, comprising gIIa, gIIb and gIIc, would be found mainly in the heavier sucrose fractions of the radioactive peak, and that gIII would be found in the higher sucrose fractions of the labelled peak because the covalently bound and non-covalently bound complexes, i.e., gI+gIV+gV+p115 and gIIa+gIIb+gIIc are larger in aggregate than gIII (see: Hampl, H., Ben-Porat, T., Ehrlicher, L., Habermehl, K. O. and Kaplan, A. S., *J. Virol.* 52:583–590 (1984)). Cellular glycoproteins of many sizes may also be present in various parts of the peak. Immunoprecipitation experiments and SDS-polyacrylamide gel electrophoresis analyses were therefore carried out to investigate the location of the different PRV glycoproteins and to distinguish them from cellular glycoproteins.

Aliquots consisting of 120 μl of PRV(Ill) antigens from fractions 14 to 27 of the sucrose gradient were added to 60 μl of Type B antisera and the mixtures were incubated for 16 to 20 hr at 4° C. Aliquots were also added to 60 μl of Type C antisera and incubated for 16 to 20 hr at 4° C. Then, 270 μl of Pansorbin was added to absorb the antigen-antibody complexes and the suspensions were incubated at 4° C. for 45 min. The resulting mixture was centrifuged, washed and extracted with buffer D as described above. SDS-PAGE analyses were then carried out as described above. In the case of the antigens precipitated with Type B antisera, the SDS-polyacrylamide gel analyses demonstrated that sucrose gradient fractions 14 to 19 contained $^{3}$H-mannose-labelled bands of 116,000 to 130,000, 98,000, 74,000, 62,000 and 58,000 daltons, indicating that the noncovalent and the covalent glycoprotein complexes were present in these fractions. Fractions 21 to 27 exhibited a single major band of radioactivity with a molecular weight of about 92,000 to 98,000 daltons. Several faint bands of lower molecular weight were also noted. Thus, fractions 21 to 27 mainly comprised the noncomplexed glycoprotein, gIII.

When the antigens in the sucrose fractions were precipitated with Type C antisera, a rather different result was obtained. Fractions 14 to 19 exhibited $^{3}$H-mannose-labeled protein bands indicative of the presence of gIIa, gIIb, gIIc, gIV and gV, as expected. However, fractions 20 to 27 did not exhibit any $^{3}$H-mannose-labeled 92,000 to 98,000 molecular weight glycoprotein, representing gIII. The results clearly demonstrate that the g92 glycoprotein is absent from the tk− PRV(dlg92/dltk)-infected cells and that the g92 glycoprotein corresponds to the glycoprotein previously designated gIII or gB (see: Hample, H., Ben-Porat, T., Ehrlicher, L., Habermehl, K. O. and Kaplan, A. S., *J. Virol.* 52:583–590 (1984); Lukacs, N., Thiel, H. J., Mettenleiter, T. C. and Rziha, H. J., *J. Virol.* 53:166–173 (1985)).

While the invention has been described in detail and with reference to specific embodiments thereof, it will be apparent to one skilled in the art that various changes and modifications can be made therein without departing from the spirit and scope thereof.

We claim:

1. A pseudorabies virus which fails to produce any antigenic g92 polypeptides as a result of a deletion, an insertion or both a deletion and an insertion in the g92 gene.

2. The pseudorabies virus as claimed in claim 1, wherein said pseudorabies virus fails to produce any antigenic g92 polypeptides as a result of a deletion in the g92 gene.

3. The pseudorabies virus as claimed in claim 1, wherein said deletion is about 10 to 1500 bp in size.

4. The pseudorabies virus as claimed in claim 3, wherein said deletion is about 75 to 200 bp in size.

5. The pseudorabies virus as claimed in claim 1, wherein said insertion is about 8 to 5000 bp in size.

6. The pseudorabies virus as claimed in claim 1, wherein said pseudorabies virus also fails to produce any functional TK as a result of a mutation in the tk gene.

7. The pseudorabies virus as claimed in claim 6, wherein said mutation in the tk gene is a deletion mutation.

8. The pseudorabies virus as claimed in claim 1, wherein said pseudorabies virus also fails to produce any glycoprotein gI as a result of a mutation in the gI gene.

9. The pseudorabies virus as claimed in claim 1, wherein said pseudorabies virus is also temperature-resistant.

10. The pseudorabies virus as claimed in claim 1, wherein said virus has the identifying characteristics of PRV(dlg92/dltk) (ATCC No. VR-2116).

11. The pseudorabies virus as claimed in claim 1, wherein said pseudorabies virus is lyophilized.

12. A pseudorabies virus which fails to produce any antigenic g92 polypeptides as a result of an insertion in the g92 gene produced by the process comprising:

(1) Constructing a hybrid plasmid comprising a cloning vector and a DNA fragment of pseudorabies virus containing substantially all of the pseudorabies virus g92 gene and flanking sequence thereof;

(2) Inserting a DNA fragment which encodes a functional selectable gene into the pseudorabies virus g92 gene of the resulting hybrid plasmid of step (1) such that the functional selectable gene is flanked by DNA sequences of the pseudorabies virus g92 gene;

(3) Co-transfecting into pseudorabies virus host cells the hybrid plasmid of step (2) with infectious DNA from a pseudorabies virus which fails to produce the product of the selectable gene and selecting for pseudorabies virus recombinants which produce the product of the selectable gene so as to produce pseudorabies virus mutants which fail to produce any antigenic g92 polypeptides as a result of an insertion in the g92 gene.

13. The pseudorabies virus as claimed in claim 12, wherein said insertion is about 8 to 5000 bp in size.

14. The pseudorabies virus as claimed in claim 12, wherein the infectious DNA of step (3) is derived from a pseudorabies virus mutant which fails to produce any functional TK such that the resulting mutants of step (3) fail to produce any antigenic g92 polypeptides as a result of an insertion in the g92 gene and fail to produce any functional TK as a result of a mutation in the tk gene.

15. The pseudorabies virus as claimed in claim 14, wherein said pseudorabies virus mutant which fails to produce any functional TK, fails to produce such as a result of deletion in the tk gene.

16. The pseudorabies virus as claimed in claim 15, wherein said PRV mutant is pseudorabies virus (BUK-dl 3).

17. The pseudorabies virus as claimed in claim 12, wherein said pseudorabies virus mutant also fails to produce any gI glycoprotein as a result of a mutation in the gI gene.

18. The pseudorabies virus as claimed in claim 12, wherein the infectious DNA of step (3) is derived from temperature-resistant pseudorabies virus such that the resulting mutants of step (3) are temperature-resistant pseudorabies virus mutants which fail to produce any antigenic g92 polypeptides as a result of an insertion in the g92 gene.

19. The pseudorabies virus as claimed in claim 12, additionally comprising step (4):

(4) Propagating the resulting pseudorabies virus of step (3) at a non-permissive temperature for a temperature-sensitive virus so as to select for and produce temperature-resistant pseudorabies virus mutants which fail to produce any antigenic g92 polypeptides as a result of an insertion in the g92 gene.

20. The pseudorabies virus as claimed in claim 12, wherein said cloning vector is selected from the group consisting of pBR322, pBR325, pKH47, pBR328, pHC79, phage Charon 28, pKB11, pKSV-10 and pMAR420.

21. The pseudorabies virus as claimed in claim 20, wherein said cloning vector is pBR322.

22. The pseudorabies virus as claimed in claim 12, wherein the resulting hybrid plasmid of step (2) is pPRVTK/Stu12.

23. The pseudorabies virus as claimed in claim 12, wherein said selectable gene is selected from the group consisting of a tk gene, the transposon Tn5 gene and the *E. coli* lacZ gene.

24. The pseudorabies virus as claimed in claim 23, wherein said selectable gene is a tk gene.

25. The pseudorabies virus as claimed in claim 24, wherein said tk gene is selected from the group consisting of the HSV-1 tk gene, the HSV-2 tk gene, the marmoset herpesvirus tk gene, the chicken tk gene, the human tk gene and the pseudorabies virus tk gene.

26. The pseudorabies virus as claimed in claim 25, wherein said tk gene is the pseudorabies virus tk gene.

27. The pseudorabies virus as claimed in claim 12, wherein said pseudorabies virus is lyophilized.

28. A pseudorabies virus which fails to produce any antigenic g92 polypeptides as a result of a deletion in the g92 gene produced by the process comprising:

(1) Constructing a hybrid plasmid comprising a cloning vector and a DNA fragment of pseudorabies virus containing substantially all of the pseudorabies virus g92 gene and flanking sequences thereof;

(2) Inserting a DNA fragment which encodes a functional selectable gene into the pseudorabies virus g92 gene of the resulting hybrid plasmid of step (1) such that the functional selectable gene is flanked by DNA sequences of the pseudorabies virus g92 gene;

(3) Co-transfecting into pseudorabies virus host cells the hybrid plasmid of step (2) with infectious DNA from a pseudorabies virus which fails to produce the product of the selectable gene, and selecting for pseudorabies virus which produce the product of the selectable gene;

(4) Deleting DNA sequences from the hybrid plasmid of step (1) such that less than substantially all of the g92 gene is present, while retaining pseudorabies virus DNA sequences adjacent to each side of the deletion;

(5) Co-transfecting in pseudorabies virus host cells the resulting hybrid plasmid of step (4) with infectious DNA from the selected pseudorabies virus of step (3), and selecting for PRV which do not produce the product of the selectable gene so as to produce pseudorabies virus mutants which fail to produce any antigenic g92 polypeptides as a result of a deletion in the g92 gene.

29. The pseudorabies virus as claimed in claim 28, wherein the deletion is about 10 to 1500 bp in size.

30. The pseudorabies virus as claimed in claim 29, wherein the deletion is about 74 to 200 bp in size.

31. The pseudorabies virus as claimed in claim 28, wherein a foreign DNA sequence is inserted in place of the deleted g92 gene sequence in step (4) such that no antigenic g92 polypeptides are produced and such that pseudorabies virus DNA sequences adjacent to each side of the deleted g92 gene sequences are retained, so that the resulting pseudorabies virus mutants of step (5) fail to produce any antigenic g92 polypeptides as a result of a combined deletion and insertion in the g92 gene.

32. The pseudorabies virus as claimed in claim 31, wherein the foreign DNA sequence is about 8 to 5000 bp in size.

33. The pseudorabies virus as claimed in claim 28, wherein the infectious DNA of step (3) is derived from a pseudorabies virus mutant which fails to produce any functional TK such that the resulting pseudorabies virus mutants of step (5) fail to produce any antigenic g92 polypeptides as a result of a deletion in the g92 gene and fail to produce any functional TK as a result of a mutation in the tk gene.

34. The pseudorabies virus as claimed in claim 33, wherein said pseudorabies virus mutant which fails to produce any functional TK, fails to produce such as a result of deletion in the tk gene.

35. The pseudorabies virus as claimed in claim 34, wherein said PRV mutant is pseudorabies virus (BUK-dl 3).

36. The pseudorabies virus as claimed in claim 28, wherein said pseudorabies virus mutant also fails to produce any gI glycoprotein as a result of a mutation in the gI gene.

37. The pseudorabies virus as claimed in claim 28, wherein the infectious DNA of step (3) is derived from a temperature-resistant pseudorabies virus such that the resulting pseudorabies virus mutants of step (5) are temperature-resistant pseudorabies virus mutants which fail to produce any antigenic g92 polypeptides as a result of a deletion in the g92 gene.

38. The pseudorabies virus as claimed in claim 28, additionally comprising step (6):

(6) Propagating the resulting pseudorabies virus of step (5) at a non-permissive temperature for a temperature-sensitive virus so as to select for and produce a temperature-resistant pseudorabies virus which fails to produce any antigenic g92 polypeptides as a result of a deletion in the g92 gene.

39. The pseudorabies virus as claimed in claim 28, wherein said cloning vector is selected from the group consisting of pBR322, pBR325, pKH47, pBR328, pHC79, phage Charon 28, pKB11, pKSV-10 and pMAR420.

40. The pseudorabies virus as claimed in claim 39, wherein said cloning vector is pBR322.

41. The pseudorabies virus as claimed in claim 28, wherein the resulting hybrid plasmid of step (2) is pPRVTK/Stu12.

42. The pseudorabies virus as claimed in claim 28, wherein the resulting hybrid plasmid of step (4) is pBUK:gCdlSal.

43. The pseudorabies virus as claimed in claim 28, wherein said selectable gene is selected from the group consisting of a tk gene, the transposon Tn5 gene and the *E. coli* lacZ gene.

44. The pseudorabies virus as claimed in claim 43, wherein said selectable gene is a tk gene.

45. The pseudorabies virus as claimed in claim 44, wherein said tk gene is selected from the group consisting of the HSV-1 tk gene, the HSV-2 tk gene, the marmoset herpesvirus tk gene, the chicken tk gene, the human tk gene and the pseudorabies virus tk gene.

46. The pseudorabies virus as claimed in claim 45, wherein said tk gene is the pseudorabies virus tk gene.

47. The pseudorabies virus as claimed in claim 28, wherein said pseudorabies virus is lyophilized.

48. A pseudorabies virus which fails to produce any antigenic g92 polypeptides as a result of an insertion in the g92 gene produced by the process comprising:

(1) Constructing a hybrid plasmid comprising a cloning vector and a DNA fragment of pseudorabies virus containing substantially all of the pseudorabies virus g92 gene and flanking sequences thereof;

(2) Inserting a DNA fragment which encodes a functional selectable gene into the pseudorabies virus g92 gene of the resulting hybrid plasmid of step (1) such that the functional selectable gene is flanked by DNA sequences of the pseudorabies virus g92 gene;

(3) Co-transfecting into pseudorabies virus host cells the hybrid plasmid of step (2) with infectious DNA from a pseudorabies virus which fails to produce the product of the selectable gene, and selecting for pseudorabies virus which produce the product of the selectable gene;

(4) Inserting a foreign DNA sequence into the plasmid of step (1) such that no antigenic g92 polypeptides are produced and such that pseudorabies virus DNA sequences adjacent to each side of the insertion are retained;

(5) Co-transfecting in pseudorabies virus host cells the resulting hybrid plasmid of step (4) with infectious DNA from the selected pseudorabies virus of step (3), and selecting for pseudorabies virus which do not produce the product of the selectable gene so as to produce pseudorabies virus mutants which fail to produce any antigenic g92 polypeptides as a result of an insertion in the g92 gene.

49. The pseudorabies virus as claimed in claim 48, wherein said insertion is about 8 to 5000 bp in size.

50. The pseudorabies virus as claimed in claim 48, wherein the infectious DNA of step (3) is derived from a pseudorabies virus mutant which fails to produce any functional TK such that the resulting mutants of step (5) fail to produce any antigenic g92 polypeptides as a result of an insertion in the g92 gene and fail to produce any functional TK as a result of a mutation in the tk gene.

51. The pseudorabies virus as claimed in claim 50, wherein said pseudorabies virus mutant which fails to produce any functional TK, fails to produce such as a result of deletion in the tk gene.

52. The pseudorabies virus as claimed in claim 51, wherein said pseudorabies virus mutant is PRV(BUK-dl 3).

53. The pseudorabies virus as claimed in claim 48, wherein said pseudorabies virus mutant also fails to produce any gI as a result of a mutation in the gI gene.

54. The pseudorabies virus as claimed in claim 48, wherein the infectious DNA of step (3) is derived from temperature-resistant pseudorabies virus such that the resulting PRV mutants of step (5) are temperature-resistant pseudorabies virus mutants which fail to produce any antigenic g92 polypeptides as a result of an insertion mutation in the g92 gene.

55. The pseudorabies virus as claimed in claim 48, additionally comprising step (6):

(6) Propagating the resulting pseudorabies virus of step (5) at a non-permissive temperature for a temperature-sensitive virus so as to select for and produce a temperature-resistant pseudorabies virus which fails to produce any antigenic g92 polypeptides as a result of an insertion mutation in the g92 gene.

56. The pseudorabies virus as claimed in claim 48, wherein said cloning vector is selected from the group consisting of pBR322, pBR325, pKH47, pBR328, pHC79, phage Charon 28, pKB11, pKSV-10 and pMAR420.

57. The pseudorabies virus as claimed in claim 56, wherein said cloning vector is pBR322.

58. The pseudorabies virus as claimed in claim 48, wherein the resulting hybrid of step (2) plasmid is pPRVTK/Stu12.

59. The pseudorabies virus as claimed in claim 48, wherein said selectable gene is selected from the group consisting of a tk gene, the transposon Tn5 gene and the *E. coli* lacZ gene.

60. The pseudorabies virus as claimed in claim 59, wherein said selectable gene is a tk gene.

61. The pseudorabies virus as claimed in claim 60, wherein said tk gene is selected from the group consisting of the HSV-1 tk gene, the HSV-2 tk gene, the marmoset herpesvirus tk gene, the chicken tk gene, the human tk gene and the pseudorabies virus tk gene.

62. The pseudorabies virus as claimed in claim 61, wherein said tk gene is the pseudorabies virus tk gene.

63. The pseudorabies virus as claimed in claim 48, wherein said pseudorabies virus is lyophilized.

* * * * *

UNITED STATES PATENT AND TRADEMARK OFFICE

CERTIFICATE OF CORRECTION

PATENT NO. : 4,711,850

DATED : December 8, 1987

INVENTOR(S) : MALON KIT, SAUL KIT

It is certified that error appears in the above-indentified patent and that said Letters Patent is hereby corrected as shown below:

Column 1, line 6:

Between the Title and Field of Invention, insert

-- The invention described herein was developed during the tenure of a Research Career Award to Saul Kit from the United States Public Health Service of Department of Health and Human Services. The Government has certain rights. --

Signed and Sealed this

Eighteenth Day of April, 1995

Attest:

BRUCE LEHMAN

*Attesting Officer*

*Commissioner of Patents and Trademarks*